US012797452B2

(12) United States Patent
Yarar et al.

(10) Patent No.: US 12,797,452 B2
(45) Date of Patent: Nov. 17, 2026

(54) METHODS TO STIMULATE IMMUNE RESPONSES TO MUTANT RAS USING ANUCLEATE CELLS

(71) Applicant: STEMCELL TECHNOLOGIES CANADA INC., Vancouver (CA)

(72) Inventors: Defne Yarar, Watertown, MA (US); Howard Bernstein, Cambridge, MA (US); Katherine Seidl, Watertown, MA (US); Amritha Ramakrishnan, Watertown, MA (US); Carolyne Kelly Smith, Waltham, MA (US); Anita Venkitaraman, Watertown, MA (US); Scott Loughhead, Watertown, MA (US); Katarina Blagovic, Cambridge, MA (US)

(73) Assignee: STEMCELL TECHNOLOGIES CANADA INC., Vancouver (CA)

(*) Notice: Subject to any disclaimer, the term of this patent is extended or adjusted under 35 U.S.C. 154(b) by 771 days.

(21) Appl. No.: 18/007,290

(22) PCT Filed: Jul. 28, 2021

(86) PCT No.: PCT/US2021/043568
§ 371 (c)(1),
(2) Date: Jan. 27, 2023

(87) PCT Pub. No.: WO2022/026621
PCT Pub. Date: Feb. 3, 2022

(65) Prior Publication Data

US 2025/0269001 A1 Aug. 28, 2025

Related U.S. Application Data

(60) Provisional application No. 63/058,438, filed on Jul. 29, 2020.

(51) Int. Cl.
*A61K 39/00* (2006.01)

(52) U.S. Cl.
CPC ............................ *A61K 39/001164* (2018.08)

(58) Field of Classification Search
None
See application file for complete search history.

(56) References Cited

U.S. PATENT DOCUMENTS

2019/0054192 A1* 2/2019 Le ........................ C12N 15/907

FOREIGN PATENT DOCUMENTS

| | | | | |
|---|---|---|---|---|
| CN | 101873862 | A | 10/2010 | |
| CN | 108138118 | A | 6/2018 | |
| WO | 2009/019317 | A1 | 2/2009 | |
| WO | 2013040547 | A2 | 3/2013 | |
| WO | 2015169804 | A1 | 11/2015 | |
| WO | WO-2017008063 | A1 * | 1/2017 | ................ A61P 7/06 |
| WO | WO-2018145020 | A1 * | 8/2018 | ........... A61K 31/192 |
| WO | 2019246286 | A1 | 12/2019 | |
| WO | 2019178006 | A2 | 9/2021 | |

OTHER PUBLICATIONS

Pollet et al. Plasma Membrane Lipid Domains as Platforms for Vesicle Biogenesis and Shedding? Biomolecules 2018, 8, 94; doi: 10.3390/biom8030094. (Year: 2018).*

Iacobucci et al. Genomic subtyping and therapeutic targeting of acute erythroleukemia. Nature Genetics, vol. 51, Apr. 2019, 694-704. (Year: 2019).*

Glassman et al. Vascular Drug Delivery Using Carrier Red Blood Cells: Focus on RBC Surface Loading and Pharmacokinetics. Pharmaceutics 2020, 12, 440; doi: 10.3390/pharmaceutics12050440. (Year: 2020).*

First Word Pharma. Online publication, Top Story "Erytech's shares plunge on failure of eryaspase in pancreatic cancer trial", published Oct. 25, 2021. (Year: 2021).*

Liu P et al, "Targeting the untargetable KRAS in cancer therapy", Acta Pharmaceutica Sinica B,vol. {0} 9, No. {0} 5, Sep. 2019 (Sep. 2019), p. 871-879, XP055630330.

Toubaji A et al, "Pilot study of mutant ras peptide-based vaccine as an adjuvant treatment in pancreatic and colorectal cancers", Cancer Immunology, Immunotherapy,vol. {0} 57, No. {0} 9, Feb. 23, 2008 (Feb. 23, 2008), p. 1413-1420, XP019624400.

Ramakrishnan, Amritha et al., "Engineering Erythrocytes with the SQZ Cell Therapy Platform to Enhance Immunotolerance," Diabetes, vol. 68, Supplement 1, Abstract No. 1743-P, Jun. 1, 2019. DOI: 10.2337/db19-1743-P.

* cited by examiner

*Primary Examiner* — Gary B Nickol
*Assistant Examiner* — Amy M. Chattin
(74) *Attorney, Agent, or Firm* — Smart & Biggar LP; Micheline Gravelle

(57) ABSTRACT

The present application provides anucleate cells comprising a mutated Ras antigen (such as a mutated K-Ras antigen), methods of manufacturing such anucleate cells comprising the mutated Ras antigen, and methods of using such modified anucleate cells for stimulating an immune response, treating, and/or vaccinating an individual with a cancer associated with Ras mutation.

20 Claims, 27 Drawing Sheets

Specification includes a Sequence Listing.

FIG. 3B

Dose Composition

| | | | |
|---|---|---|---|
| **IFA/HBV/ G12V$^{7-16}$ (Dose: 300µL)** | **KRas G12V$^{7-16}$** | **HBV Core peptide** | **IFA** |
| | 100µg (0.11 µmol) | 100µg | 50% (equal volume IFA added to peptide volume) |
| **IFA/HBV/ G12V$^{1-16}$ (Dose: 300µL)** | **KRas G12V$^{1-16}$** | **HBV Core peptide** | **IFA** |
| | 100µg (0.11 µmol) | 100µg | 50% (equal volume IFA added to peptide volume) |
| **AC-Kras G12V$^{1-16}$ /Poly I:C (Dose: 250M ACs)** | **KRas G12V$^{1-16}$** | **Delivery Media** | **Invivogen low molecular weight poly I:C (added exogenously to ACs)** |
| | 200 µM | RPMI | 1 mg/mL (between 73-105µL added, depending on AC recovery) |

*In vitro* Expansion Workflow (6-Day)

SEQUENCE LISTING

<160> NUMBER OF SEQ ID NOS: 17

<210> SEQ ID NO 1
<211> LENGTH: 16
<212> TYPE: PRT
<213> ORGANISM: Artificial Sequence
<220> FEATURE:
<223> OTHER INFORMATION: Synthetic Construct

<400> SEQUENCE: 1

Met Thr Glu Tyr Lys Leu Val Val Val Gly Ala Asp Gly Val Gly Lys
1 5 10 15

<210> SEQ ID NO 2
<211> LENGTH: 18
<212> TYPE: PRT

<213> ORGANISM: Artificial Sequence
<220> FEATURE:
<223> OTHER INFORMATION: Synthetic Construct

<400> SEQUENCE: 2

Thr Glu Tyr Lys Leu Val Val Val Gly Ala Asp Gly Val Gly Lys Ser
1 5 10 15

Ala Leu

<210> SEQ ID NO 3
<211> LENGTH: 21
<212> TYPE: PRT
<213> ORGANISM: Artificial Sequence
<220> FEATURE:
<223> OTHER INFORMATION: Synthetic Construct

<400> SEQUENCE: 3

Thr Glu Tyr Lys Leu Val Val Val Gly Ala Asp Gly Val Gly Lys Ser
1 5 10 15

Ala Leu Thr Ile Gln
20

<210> SEQ ID NO 4
<211> LENGTH: 28
<212> TYPE: PRT
<213> ORGANISM: Artificial Sequence
<220> FEATURE:
<223> OTHER INFORMATION: Synthetic Construct

<400> SEQUENCE: 4

Thr Glu Tyr Lys Leu Val Val Val Gly Ala Asp Gly Val Gly Lys Ser
1 5 10 15

Ala Leu Thr Ile Gln Leu Ile Gln Asn His Phe Val
20 25

<210> SEQ ID NO 5
<211> LENGTH: 16
<212> TYPE: PRT
<213> ORGANISM: Artificial Sequence
<220> FEATURE:
<223> OTHER INFORMATION: Synthetic Construct

<400> SEQUENCE: 5

Met Thr Glu Tyr Lys Leu Val Val Val Gly Ala Val Gly Val Gly Lys
1 5 10 15

<210> SEQ ID NO 6
<211> LENGTH: 18
<212> TYPE: PRT
<213> ORGANISM: Artificial Sequence
<220> FEATURE:
<223> OTHER INFORMATION: Synthetic Construct

<400> SEQUENCE: 6

Thr Glu Tyr Lys Leu Val Val Val Gly Ala Val Gly Val Gly Lys Ser
1 5 10 15

Ala Leu

<210> SEQ ID NO 7
<211> LENGTH: 15
<212> TYPE: PRT
<213> ORGANISM: Artificial Sequence
<220> FEATURE:
<223> OTHER INFORMATION: Synthetic Construct

<400> SEQUENCE: 7

Glu Tyr Lys Leu Val Val Val Gly Ala Val Gly Val Gly Lys Ser
1 5 10 15

<210> SEQ ID NO 8
<211> LENGTH: 40
<212> TYPE: PRT
<213> ORGANISM: Artificial Sequence
<220> FEATURE:
<223> OTHER INFORMATION: Synthetic Construct

<400> SEQUENCE: 8

Glu Tyr Lys Leu Val Val Val Gly Ala Val Gly Val Gly Lys Ser Ala
1 5 10 15

Leu Thr Ile Gln Leu Ile Gln Asn His Phe Val Asp Glu Tyr Asp Pro
20 25 30

Thr Ile Glu Asp Ser Tyr Arg Lys
35 40

<210> SEQ ID NO 9
<211> LENGTH: 10
<212> TYPE: PRT
<213> ORGANISM: Artificial Sequence
<220> FEATURE:
<223> OTHER INFORMATION: Synthetic Construct

<400> SEQUENCE: 9

Val Val Val Gly Ala Asp Gly Val Gly Lys
1 5 10

<210> SEQ ID NO 10
<211> LENGTH: 10
<212> TYPE: PRT
<213> ORGANISM: Artificial Sequence
<220> FEATURE:
<223> OTHER INFORMATION: Synthetic Construct

<400> SEQUENCE: 10

Val Val Val Gly Ala Val Gly Val Gly Lys
1 5 10

<210> SEQ ID NO 11
<211> LENGTH: 10
<212> TYPE: PRT
<213> ORGANISM: Artificial Sequence
<220> FEATURE:
<223> OTHER INFORMATION: Synthetic Construct

<400> SEQUENCE: 11

Val Val Val Gly Ala Cys Gly Val Gly Lys
1 5 10

<210> SEQ ID NO 12
<211> LENGTH: 9
<212> TYPE: PRT
<213> ORGANISM: Artificial Sequence
<220> FEATURE:
<223> OTHER INFORMATION: Synthetic Construct

<400> SEQUENCE: 12

Val Val Gly Ala Asp Gly Val Gly Lys
1 5

<210> SEQ ID NO 13
<211> LENGTH: 9

-continued

```
<212> TYPE: PRT
<213> ORGANISM: Artificial Sequence
<220> FEATURE:
<223> OTHER INFORMATION: Synthetic Construct

<400> SEQUENCE: 13

Val Val Gly Ala Val Gly Val Gly Lys
1               5


<210> SEQ ID NO 14
<211> LENGTH: 10
<212> TYPE: PRT
<213> ORGANISM: Artificial Sequence
<220> FEATURE:
<223> OTHER INFORMATION: Synthetic Construct

<400> SEQUENCE: 14

Lys Leu Val Val Val Gly Ala Asp Gly Val
1               5                   10


<210> SEQ ID NO 15
<211> LENGTH: 10
<212> TYPE: PRT
<213> ORGANISM: Artificial Sequence
<220> FEATURE:
<223> OTHER INFORMATION: Synthetic Construct

<400> SEQUENCE: 15

Gly Ala Asp Gly Val Gly Lys Ser Ala Leu
1               5                   10


<210> SEQ ID NO 16
<211> LENGTH: 20
<212> TYPE: DNA
<213> ORGANISM: Artificial Sequence
<220> FEATURE:
<223> OTHER INFORMATION: Synthetic Construct

<400> SEQUENCE: 16

tccatgacgt tcctgacgtt                                                   20


<210> SEQ ID NO 17
<211> LENGTH: 24
<212> TYPE: DNA
<213> ORGANISM: Artificial Sequence
<220> FEATURE:
<223> OTHER INFORMATION: Synthetic Construct

<400> SEQUENCE: 17

tcgtcgtttt gtcgttttgt cgtt                                              24
```

METHODS TO STIMULATE IMMUNE RESPONSES TO MUTANT RAS USING ANUCLEATE CELLS

CROSS-REFERENCE TO RELATED APPLICATIONS

This application claims priority to U.S. Provisional Application Nos. 63/058,438 filed on Jul. 29, 2020, the contents of which are incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 750322002740SEQLIST.TXT, date recorded: Jul. 28, 2021, size: 5 KB).

FIELD OF THE INVENTION

The present disclosure relates generally to anucleate cell-derived vesicles comprising a mutated Ras antigen, methods of manufacturing such anucleate cell-derived vesicles, and methods of using such anucleate cell-derived vesicles for treating a cancer associated with mutated Ras protein.

BACKGROUND OF THE INVENTION

Ras is one of the most well-known proto-oncogenes. Its gain-of-function mutations occur in approximately 30% of all human cancers. As the most frequently mutated Ras isoform, K-Ras has been intensively studied in the past years. Despite its well-recognized importance in cancer malignancy, continuous efforts in the past three decades have failed to develop therapies for K-Ras mutant cancer, and to date, no therapy for such malignancy has been approved. K-Ras has thus long been considered undruggable.

Members of the Ras superfamily are divided into families and subfamilies based on their structure, sequence and function. K-Ras belongs to a group of small guanosine triphosphate (GTP) binding proteins known as the Ras superfamily or RAS-like GTPases. In humans, three RAS genes encode highly homologous RAS proteins, H-Ras, N-Ras and K-Ras. K-Ras is one of the front-line sensors that initiate the activation of an array of signaling molecules, allowing the transmission of transducing signals from the cell surface to the nucleus, and affecting a range of essential cellular processes such as cell differentiation, growth, chemotaxis and apoptosis. The K-Ras isoform is the isoform most frequently mutated, and constitutes 86% of RAS mutations. There are two known isoform splice variants within the K-Ras isoform: K-Ras4A and K-Ras4B. The K-Ras4B splice variant is the dominant isoform with mutations in human cancers, and it is present in approximately 90% of pancreatic cancers, 30% to 40% of colon cancers, and 15% to 20% of lung cancers, mostly non-small-cell lung cancer (NSCLC) (Liu, P. et al., *Acta Pharmaceutica Sinica B,* 2019, 9(5):871-879). It is also present in biliary tract malignancies, endometrial cancer, cervical cancer, bladder cancer, liver cancer, myeloid leukemia and breast cancer. Despite its prevalence, decades long efforts in the discovery of RAS targeted therapies have repeatedly failed to produce clinically approved drugs.

Immunotherapy can be divided into two main types of interventions, either passive or active. Passive protocols include administration of pre-activated and/or engineered cells (e.g., CAR T cells), disease-specific therapeutic antibodies, and/or cytokines. Active immunotherapy strategies are directed at stimulating immune system effector functions in vivo. Several current active protocols include vaccination strategies with disease-associated peptides, lysates, or allogeneic whole cells, infusion of autologous dendritic cell (DCs) as vehicles for tumor antigen delivery, and infusion of immune checkpoint modulators. See Papaioannou, Nikos E., et al. *Annals of translational medicine* 4.14 (2016). Adoptive immunotherapy can be employed to modulate the immune response, enhance antitumor activity, and achieve the goal of treating or preventing cancers associated with Ras mutations.

$CD8^+$ cytotoxic T lymphocytes (CTL) and $CD4^+$ helper T (Th) cells stimulated by disease-associated antigens have the potential to target and destroy diseased cells; however, current methods for inducing endogenous T cell responses have faced challenges. The methods described herein are used to generate nucleated cells comprising mutated Ras antigens efficiently in a high throughput manner, which can be utilized in inducing a robust T cell response to mutated Ras antigens.

All references cited herein, including patent applications and publications, are incorporated by reference in their entirety. The patent publications WO 2016070136, US 20180142198, WO 2017/008063, US 20180201889, WO 2019/178005, and WO 2019178006 and PCT/US2020/020194 are hereby expressly incorporated by reference in their entirety.

BRIEF SUMMARY OF THE INVENTION

In some aspects, the invention provides methods for stimulating an immune response to a mutated Ras protein in an individual, the method comprising administering an effective amount of a composition comprising anucleate cell-derived vesicles to an individual, wherein anucleate cell-derived vesicles comprise a mutated Ras antigen; wherein the mutated Ras antigen is delivered to the anucleate cell-derived vesicles intracellularly. In some aspects, the invention provides methods for reducing tumor growth in an individual, the method comprising administering an effective amount of a composition comprising anucleate cell-derived vesicles to an individual, wherein the anucleate cells comprise a mutated Ras antigen; wherein the mutated Ras antigen is delivered to the anucleate cell-derived vesicles intracellularly. In some aspects, the invention provides methods for vaccinating an individual in need thereof, the method comprising administering an effective amount of a composition comprising anucleate cell-derived vesicles to an individual, wherein the anucleate cell-derived vesicles comprise a mutated Ras antigen; wherein the mutated Ras antigen is delivered to the anucleate cell-derived vesicles intracellularly. In some embodiments, the individual has cancer. In some aspects, the invention provides methods comprising administering an effective amount of a composition comprising anucleate cell-derived vesicles to an individual, wherein the anucleate cell-derived vesicles comprise a mutated Ras antigen; wherein the mutated Ras antigen is delivered to the anucleate cell-derived vesicles intracellularly. In some embodiments, the cancer is a pancreatic cancer, a colon cancer, a small intestine cancer, a biliary tract cancer, an endometrial cancer, a lung cancer, a skin cancer, an ovarian cancer, a stomach cancer, an esophageal cancer, a cervical cancer or a urinary tract cancer.

In some embodiments of the methods described herein, the mutated Ras antigen is a mutated K-Ras antigen, a mutated H-Ras antigen, or a mutated N-Ras antigen. In some embodiments, the mutated Ras antigen is a mutated K-Ras4A antigen or a mutated K-Ras4B antigen. In some embodiments, the mutated Ras antigen is a single polypeptide that elicits a response against the same and or different mutated Ras antigens. In some embodiments, the mutated Ras antigen is a pool of multiple polypeptides that elicit a response against the same and or different mutated Ras antigens. In some embodiments, the mutated Ras antigen is a polypeptide comprising one or more antigenic mutated Ras epitopes and one or more heterologous peptide sequences. In some embodiments, the mutated Ras antigen complexes with other antigens or with an adjuvant. In some embodiments, the mutated Ras antigen comprises a G12D mutation, a G12V mutation, a G12C mutation or a G13D mutation. In some embodiments, mutated Ras antigen comprises an amino acid sequence with at least 90% similarity to any one of SEQ ID NOs:9-15. In some embodiments, the mutated Ras antigen comprises an amino acid sequence of SEQ ID NOs:9-15. In some embodiments, the mutated Ras antigen is one or more of a $G12D^{1-16}$, a $G12D^{2-19}$, a $G12D^{2-22}$, a $G12D^{2-29}$, a $G12V^{1-16}$, a $G12V^{2-19}$, a $G12V^{3-17}$, or a $G12V^{3-42}$ antigen. In some embodiments, the mutated Ras antigen comprises an amino acid sequence with at least 90% similarity to any one of SEQ ID NOs:1-8. In some embodiments, the mutated Ras antigen comprises an amino acid sequence of SEQ ID NOs:1-8. In some embodiments, the mutated Ras antigen is a polypeptide comprising one or more antigenic mutated Ras epitopes that is flanked on the N-terminus and/or the C-terminus by one or more heterologous peptide sequences. In some embodiments, the mutated Ras antigen is capable of being processed into an MHC class I-restricted peptide. In some embodiments, the mutated Ras antigen is capable of being processed into an MHC class II-restricted peptide.

In some embodiments of the methods described herein, the anucleate cell further comprises an adjuvant. In some embodiments, the composition is administered in conjunction with an adjuvant. In some embodiments, the adjuvant is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid, R837, R848, a TLR3 agonist, a TLR4 agonist or a TLR9 agonist. In some embodiments, the adjuvant is polyinosinic-polycytidylic acid.

In some embodiments of the methods described herein the anucleate cell-derived vesicles comprising the mutated Ras antigen or the mutated Ras antigen and an adjuvant are prepared by a) passing a cell suspension comprising input anucleate cells through a cell-deforming constriction, wherein a diameter of the constriction is a function of a diameter of the input anucleate cells in the suspension, thereby causing perturbations of the input anucleate cells large enough for the mutated Ras antigen or the mutated Ras antigen and an adjuvant to pass through to form a perturbed input anucleate cells; and b) incubating the perturbed input anucleate cells with the mutated Ras antigen or the mutated Ras antigen and an adjuvant for a sufficient time to allow the mutated Ras antigen or the mutated Ras antigen and an adjuvant to enter the perturbed input anucleate cells; thereby generating anucleate cell-derived vesicles comprising the mutated Ras antigen or the mutated Ras antigen and an adjuvant. In some embodiments, the anucleate cell-derived vesicles comprising the mutated Ras antigen are prepared by a) passing a cell suspension comprising input anucleate cells through a cell-deforming constriction, wherein a diameter of the constriction is a function of a diameter of the input anucleate cells in the suspension, thereby causing perturbations of the input anucleate cells large enough for a nucleic acid encoding the mutated Ras antigen to pass through to form a perturbed input anucleate cells; and b) incubating the perturbed input anucleate cells with the nucleic acid encoding the mutated Ras antigen for a sufficient time to allow the nucleic acid encoding the mutated Ras antigen to enter the perturbed input anucleate cells; wherein the nucleic acid encoding the mutated Ras antigen is expressed thereby generating anucleate cell-derived vesicles comprising the mutated Ras antigen. In some embodiments, the anucleate cell-derived vesicles comprising the mutated Ras antigen and an adjuvant are prepared by a) passing a cell suspension comprising input anucleate cells through a cell-deforming constriction, wherein a diameter of the constriction is a function of a diameter of the input anucleate cells in the suspension, thereby causing perturbations of the input anucleate cells large enough for a nucleic acid encoding the mutated Ras antigen and for an adjuvant to pass through to form a perturbed input anucleate cells; and b) incubating the perturbed input anucleate cells with the nucleic acid encoding the mutated Ras antigen and with the adjuvant for a sufficient time to allow the nucleic acid encoding the mutated Ras antigen and for the adjuvant to enter the perturbed input anucleate cells; wherein the nucleic acid encoding the mutated Ras antigen is expressed thereby generating anucleate cell-derived vesicles comprising the mutated Ras antigen and an adjuvant. In some embodiments, the width of the constriction is about 10% to about 99% of the mean diameter of the input anucleate cells. In some embodiments, the width of the constriction is about 1.6 μm to about 2.4 μm or about 1.8 μm to about 2.2 μm. In some embodiments, the cell suspension comprising the plurality of input anucleate cells are passed through multiple constrictions wherein the multiple constrictions are arranged in series and/or in parallel.

In some embodiments of the methods described herein the anucleate cell is a red blood cell or a platelet. In some embodiments, the anucleate cell is an erythrocyte or a reticulocyte. In some embodiments, the composition comprising the anucleate cell-derived vesicles is administered a plurality of times. In some embodiments, the composition is administered intravenously. In some embodiments, the individual is a human.

In some embodiments of the methods described herein, the composition is administered prior to, concurrently with, or following administration of another therapy. In some embodiments, another therapy is a chemotherapy, a radiation therapy, an antibody, a cytokine, an immune checkpoint inhibitor, or a bispecific polypeptide used in immune-oncology therapy.

In some aspects, the invention provides compositions comprising anucleate cell-derived vesicles, wherein the anucleate cell-derived vesicles comprise a mutated Ras antigen; wherein the mutated Ras antigen is delivered to the anucleate cell-derived vesicles intracellularly. In some embodiments, the composition further comprises an adjuvant. In some embodiments, the adjuvant is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid, R837, R848, a TLR3 agonist, a TLR4 agonist or a TLR9 agonist. In some embodiments, the adjuvant is polyinosinic-polycytidylic acid.

In some aspects, the invention provides compositions comprising anucleate cell-derived vesicles comprising a mutated Ras antigen or a mutated Ras antigen and an adjuvant, wherein the anucleate cell-derived vesicles comprising the mutated Ras antigen or the mutated Ras antigen and an adjuvant are prepared by a) passing a cell suspension comprising input anucleate cells through a cell-deforming constriction, wherein a diameter of the constriction is a function of a diameter of the input anucleate cells in the suspension, thereby causing perturbations of the input anucleate cells large enough for the mutated Ras antigen or the mutated Ras antigen and the adjuvant to pass through to form a perturbed input anucleate cells; and b) incubating the perturbed input anucleate cells with the mutated Ras antigen or the mutated Ras antigen and the adjuvant for a sufficient time to allow the mutated Ras antigen the mutated Ras antigen or the mutated Ras antigen and the adjuvant to enter the perturbed input anucleate cells; thereby generating anucleate cell-derived vesicles comprising the mutated Ras antigen or the mutated Ras antigen and the adjuvant. In some aspects, the invention provides compositions comprising anucleate cell-derived vesicles comprising a mutated Ras antigen, wherein the anucleate cell-derived vesicles comprising the mutated Ras antigen are prepared by a) passing a cell suspension comprising input anucleate cells through a cell-deforming constriction, wherein a diameter of the constriction is a function of a diameter of the input anucleate cells in the suspension, thereby causing perturbations of the input anucleate cells large enough for a nucleic acid encoding the mutated Ras antigen to pass through to form perturbed input anucleate cells; and b) incubating the perturbed input anucleate cells with the nucleic acid encoding the mutated Ras antigen for a sufficient time to allow the nucleic acid encoding the mutated Ras antigen to enter the perturbed input anucleate cells, wherein the nucleic acid expressed the mutated Ras antigen; thereby generating anucleate cell-derived vesicles comprising the mutated Ras antigen. In some aspects, the invention provides compositions comprising anucleate cell-derived vesicles comprising a mutated Ras antigen and an adjuvant, wherein the anucleate cells comprising the mutated Ras antigen and an adjuvant are prepared by a) passing a cell suspension comprising input anucleate cells through a cell-deforming constriction, wherein a diameter of the constriction is a function of a diameter of the input anucleate cells in the suspension, thereby causing perturbations of the input anucleate cells large enough for a nucleic acid encoding the mutated Ras antigen and for the adjuvant to pass through to form perturbed input anucleate cells; and b) incubating the perturbed input anucleate cells with the nucleic acid encoding the mutated Ras antigen and with the adjuvant for a sufficient time to allow the nucleic acid encoding the mutated Ras antigen and for the adjuvant to enter the perturbed input anucleate cells; wherein the nucleic acid encoding the mutated Ras antigen is expressed thereby generating anucleate cell-derived vesicles comprising the mutated Ras antigen and the adjuvant. In some embodiments, the width of the constriction is about 10% to about 99% of the mean diameter of the input anucleate cells. In some embodiments, the width of the constriction is about 1.6 μm to about 2.4 μm or about 1.8 μm to about 2.2 μm. In some embodiments, the cell suspension comprising the input anucleate cells are passed through multiple constrictions wherein the multiple constrictions are arranged in series and/or in parallel.

In some embodiments of the compositions described herein the input anucleate cell is a red blood cell or a platelet. In some embodiments, the input anucleate cell is an erythrocyte or a reticulocyte. In some embodiments, the anucleate cell-derived vesicle is a red blood cell-derived vesicle or a platelet-derived vesicle. In some embodiments, the anucleate cell-derived vesicle is a reticulocyte-derived vesicle or an erythryocte-derived vesicle.

In some embodiments of the compositions described herein, the mutated Ras antigen is a mutated K-Ras antigen, a mutated H-Ras antigen, or a mutated N-Ras antigen. In some embodiments, the mutated Ras antigen is a mutated K-Ras4A antigen or a mutated K-Ras4B antigen. In some embodiments, the mutated Ras antigen is a single polypeptide that elicits a response against the same and or different mutated Ras antigens. In some embodiments, the mutated Ras antigen is a pool of multiple polypeptides that elicit a response against the same and or different mutated Ras antigens. In some embodiments, the mutated Ras antigen complexes with other antigens or with an adjuvant. In some embodiments, the mutated Ras antigen comprises a G12D mutation, a G12V mutation, a G12C mutation, or a G13D mutation. In some embodiments, the mutated Ras antigen comprises an amino acid sequence with at least 90% similarity to any one of SEQ ID NOs:9-15. In some embodiments, the mutated Ras antigen comprises an amino acid sequence of SEQ ID NOs:9-15. In some embodiments, the mutated Ras antigen is one or more of a $G12D^{1-16}$, a $G12D^{2-19}$, a $G12D^{2-22}$, a $G12D^{2-29}$ antigen, a $G12V^{1-16}$, a $G12V^{2-19}$, a $G12V^{3-17}$, or a $G12V^{3-42}$ antigen. In some embodiments, the mutated Ras antigen comprises an amino acid sequence with at least 90% similarity to any one of SEQ ID NOs:1-8. In some embodiments, the mutated Ras antigen comprises an amino acid sequence of SEQ ID NOs:1-8. In some embodiments, the mutated Ras antigen is a polypeptide comprising one or more antigenic mutated Ras epitopes that is flanked on the N-terminus and/or the C-terminus by one or more heterologous peptide sequences. In some embodiments, the mutated Ras antigen is capable of being processed into an MHC class I-restricted peptide. In some embodiments, the mutated Ras antigen is capable of being processed into an MHC class II-restricted peptide.

In some embodiments of the compositions filed herein, the composition further comprises an adjuvant. In some embodiments, the adjuvant is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid, R837, R848, a TLR3 agonist, a TLR4 agonist or a TLR9 agonist. In some embodiments, the adjuvant is polyinosinic-polycytidylic acid.

In some aspects, the invention provides kits for use in any of the methods described herein. In some aspects, the invention provides kits comprising any one of the compositions described herein. In some embodiments, the kit further comprises one or more of buffers, diluents, filters, needles, syringes, or package inserts with instructions for administering the composition to an individual to stimulate an immune response to a mutated Ras, reduce tumor growth and/or treat cancer.

In some aspects, the invention provides methods for producing a composition of anucleate cell-derived vesicles comprising a mutated Ras antigen; the method comprising introducing the mutated Ras antigen to the anucleate cell-derived vesicles intracellularly. In some embodiments, the anucleate cell further comprises an adjuvant. In some embodiments, the adjuvant is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid, R837, R848, a TLR3 agonist, a TLR4 agonist or a TLR9 agonist. In some embodiments, the adjuvant is polyinosinic-polycytidylic acid. In some embodiments, introducing the mutated Ras antigen or the mutated Ras antigen and the adjuvant to anucleate cell-derived vesicles intracellularly comprises a) passing a cell suspension comprising input anucleate cells through a cell-deforming constriction, wherein a diameter of the constriction is a function of a diameter of the input anucleate cells in the suspension, thereby causing perturbations of the input anucleate cells large enough for the mutated Ras antigen or the mutated Ras antigen and the adjuvant to pass through to form perturbed input anucleate cells; and b) incubating the perturbed input anucleate cells with the mutated Ras antigen or the mutated Ras antigen and the adjuvant for a sufficient time to allow the mutated Ras antigen or the mutated Ras antigen and the adjuvant to enter the perturbed input anucleate cells; thereby generating anucleate cell-derived vesicles comprising the mutated Ras antigen or the mutated Ras antigen and the adjuvant. In some embodiments, introducing the mutated Ras antigen to the anucleate cell-derived vesicles intracellularly comprises a) passing a cell suspension comprising input anucleate cells through a cell-deforming constriction, wherein a diameter of the constriction is a function of a diameter of the input anucleate cells in the suspension, thereby causing perturbations of the input anucleate cells large enough for a nucleic acid encoding the mutated Ras antigen to pass through to form a perturbed input anucleate cells; and b) incubating the perturbed input anucleate cells with the nucleic acid encoding the mutated Ras antigen for a sufficient time to allow the nucleic acid encoding the mutated Ras antigen to enter the perturbed input anucleate cells, wherein the nucleic acid expressed the mutated Ras antigen; thereby generating anucleate cells comprising the mutated Ras antigen. In some embodiments, the anucleate cell-derived vesicles further comprises an adjuvant intracellularly, wherein introducing the mutated Ras antigen and the adjuvant to the anucleate cell intracellularly comprises a) passing a cell suspension comprising input anucleate cells through a cell-deforming constriction, wherein a diameter of the constriction is a function of a diameter of the input anucleate cells in the suspension, thereby causing perturbations of the input anucleate cells large enough for a nucleic acid encoding the mutated Ras antigen and for the adjuvant to pass through to form perturbed input anucleate cells; and b) incubating the perturbed input anucleate cells with the nucleic acid encoding the mutated Ras antigen and with the adjuvant for a sufficient time to allow the nucleic acid encoding the mutated Ras antigen and for the adjuvant to enter the perturbed input anucleate cells; wherein the nucleic acid encoding the mutated Ras antigen is expressed thereby generating anucleate cell-derived vesicles comprising the mutated Ras antigen and the adjuvant. In some embodiments, the width of the constriction is about 10% to about 99% of the mean diameter of the input anucleate cells. In some embodiments, the width of the constriction is about 1.6 μm to about 2.4 μm or about 1.8 μm to about 2.2 μm. In some embodiments, the cell suspension comprising the plurality of input anucleate cells are passed through multiple constrictions wherein the multiple constrictions are arranged in series and/or in parallel.

BRIEF DESCRIPTION OF THE DRAWINGS

FIG. 3B illustrates the dose compositions in administration of IFA/HBV/G12V$^{7-16}$ or AAC$^{G12V1-16}$/poly I:C.

5C shows the percentage of recovery of ACs and AACs subsequent to squeeze-processing of RBCs.

DETAILED DESCRIPTION OF THE INVENTION

Figure 1:
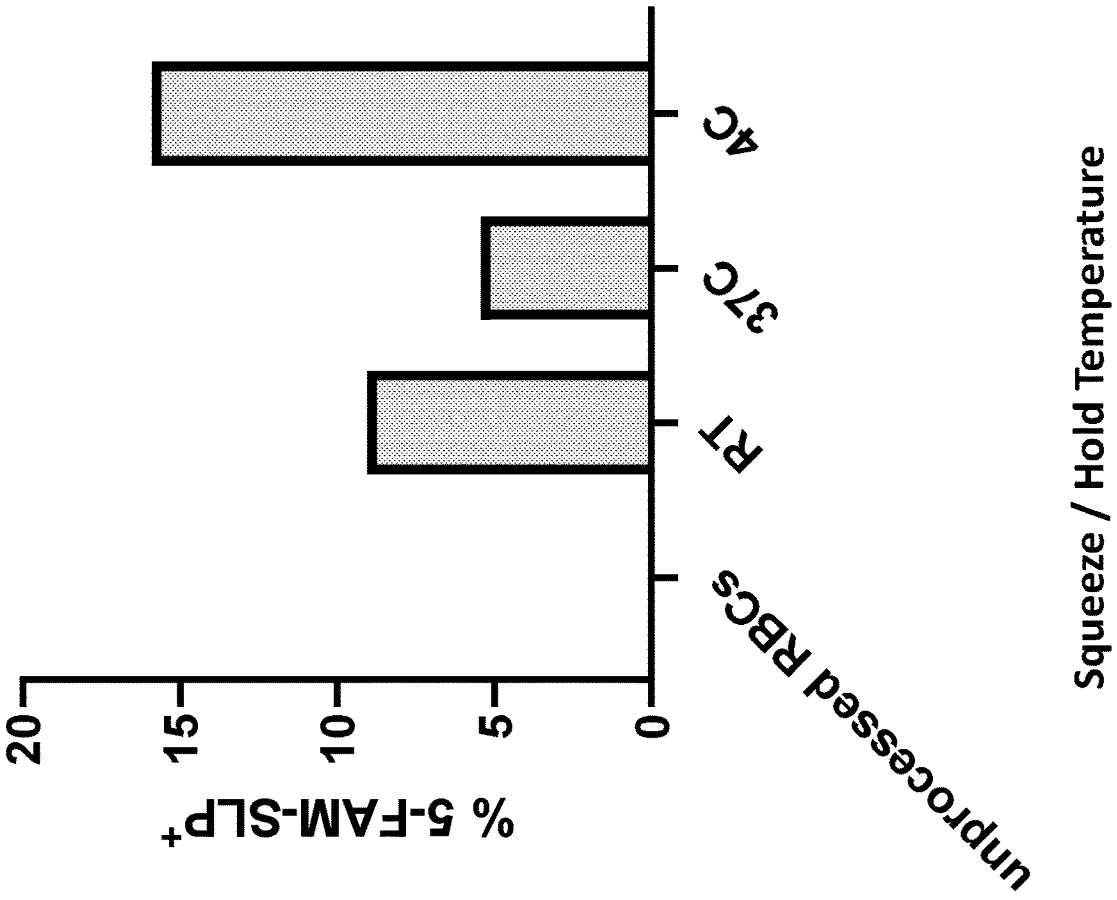
FIG. 1 shows the efficacy of intracellular delivery of a fluorescently labeled mutant Ras synthetic long peptide into RBCs by constriction-mediated delivery (squeeze) carried out at 25° C. (RT), at 37° C. and at 4° C.

In some aspects, the present invention provides methods for treating or preventing a cancer associated with a Ras mutation, and/or stimulating an immune response in an individual with a cancer associated with a Ras mutation, comprising administering to the individual a composition comprising anucleate cell-derived vesicles (e.g. RBC-derived vesicles) comprising a mutated Ras antigen. In some aspects, the present invention provides methods for treating a cancer associated with a Ras mutation, and/or stimulating an immune response in an individual with a cancer associated with a Ras mutation, the method comprising administering to the individual an effective amount of a composition comprising anucleate cell-derived vesicles comprising a mutated Ras antigen delivered intracellularly; wherein the anucleate cell-derived vesicles are prepared by first passing a cell suspension comprising input anucleate cells through a cell-deforming constriction, wherein a diameter of the constriction is a function of a diameter of the input anucleate cells in the suspension, thereby causing perturbations of the input anucleate cells large enough for the mutated Ras antigen to pass through to form perturbed input anucleate cells; and then incubating the perturbed input anucleate cells with the mutated Ras antigen for a sufficient time to allow the mutated Ras antigen to enter the perturbed input cell; thereby generating the anucleate cell-derived vesicles comprising the mutated Ras antigen. Certain aspects of the present disclosure relate to methods for generating a composition comprising anucleate cell-derived vesicles comprising a mutated Ras antigen delivered intracellularly, wherein an input anucleate cell is passed through a constriction, wherein the constriction deforms the cell thereby causing a perturbation of the cell such that an Ras antigen and/or an adjuvant enters the anucleate cell, thereby generating an anucleate cell-derived vesicles comprising the Ras antigen and/or adjuvant.

In some aspects, the present invention provides methods for treating or preventing a cancer associated with a Ras mutation (such as cancer associated with a K-Ras mutation), and/or modulating the immune response in an individual with an cancer associated with a Ras mutation comprising administering to the individual a composition comprising anucleate cell-derived vesicles wherein the anucleate cell-derived vesicles comprise intracellularly a mutated Ras antigen. In some aspects, the present invention provides methods for treating or preventing a cancer associated with a Ras mutation, and/or modulating the immune response in an individual with a cancer associated with a Ras mutation, the method comprising administering to the individual an effective amount of a composition comprising anucleate cell-derived vesicles, wherein the anucleate cell-derived vesicles comprise intracellularly a mutated Ras antigen, wherein the anucleate cell-derived vesicles are prepared by first passing a cell suspension comprising input anucleate cells through a cell-deforming constriction, wherein a diameter of the constriction is a function of a diameter of the input anucleate cells in the suspension, thereby causing perturbations of the input anucleate cells large enough for the mutated Ras antigen to pass through to form perturbed input anucleate cells; and then incubating the perturbed input anucleate cells with the mutated Ras antigen for a sufficient time to allow the mutated Ras antigen to enter the perturbed input anucleate cells; thereby generating the anucleate cell-derived vesicles comprising the mutated Ras antigen. Certain aspects of the present disclosure relate to methods for generating a composition comprising anucleate cell-derived vesicles, wherein input anucleate cell is passed through a constriction, wherein the constriction deforms the input anucleate cell thereby causing a perturbation of the input anucleate cell such that a mutated Ras antigen enters the perturbed input anucleate cells, thereby generating the anucleate cell-derived vesicles comprising the mutated Ras antigen. In some further embodiments, the method for treating a cancer associated with a Ras mutation, and/or stimulating the immune response to mutated Ras protein in an individual with a cancer associated with a Ras mutation further comprises administering an adjuvant to the individual.

General Techniques

The techniques and procedures described or referenced herein are generally well understood and commonly employed using conventional methodology by those skilled in the art, such as, for example, the widely utilized methodologies described in *Molecular Cloning: A Laboratory Manual* (Sambrook et al., $4^{th}$ ed., Cold Spring Harbor Laboratory Press, Cold Spring Harbor, N.Y., 2012); *Current Protocols in Molecular Biology* (F. M. Ausubel, et al. eds., 2003); the series *Methods in Enzymology* (Academic Press, Inc.); *PCR 2: A Practical Approach* (M. J. MacPherson, B. D. Hames and G. R. Taylor eds., 1995); *Antibodies, A Laboratory Manual* (Harlow and Lane, eds., 1988); *Culture of Animal Cells: A Manual of Basic Technique and Specialized Applications* (R. I. Freshney, $6^{th}$ ed., J. Wiley and Sons, 2010); *Oligonucleotide Synthesis* (M. J. Gait, ed., 1984); *Methods in Molecular Biology, Humana Press; Cell Biology: A Laboratory Notebook* (J. E. Cellis, ed., Academic Press, 1998); *Introduction to Cell and Tissue Culture* (J. P. Mather and P. E. Roberts, Plenum Press, 1998); *Cell and Tissue Culture: Laboratory Procedures* (A. Doyle, J. B. Griffiths, and D. G. Newell, eds., J. Wiley and Sons, 1993-8); *Handbook of Experimental Immunology* (D. M. Weir and C. C. Blackwell, eds., 1996); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Ausubel et al., eds., J. Wiley and Sons, 2002); *Immunobiology* (C. A. Janeway et al., 2004); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane, Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 2011)

Definitions

For purposes of interpreting this specification, the following definitions will apply and whenever appropriate, terms used in the singular will also include the plural and vice versa. In the event that any definition set forth below conflicts with any document incorporated herein by reference, the definition set forth shall control.

As used herein, the singular form "a", "an", and "the" includes plural references unless indicated otherwise.

The terms "comprising," "having," "containing," and "including," and other similar forms, and grammatical equivalents thereof, as used herein, are intended to be equivalent in meaning and to be open ended in that an item or items following any one of these words is not meant to be an exhaustive listing of such item or items, or meant to be limited to only the listed item or items. For example, an article "comprising" components A, B, and C can consist of (i.e., contain only) components A, B, and C, or can contain not only components A, B, and C but also one or more other components. As such, it is intended and understood that "comprises" and similar forms thereof, and grammatical equivalents thereof, include disclosure of embodiments of "consisting essentially of" or "consisting of."

Where a range of values is provided, it is understood that each intervening value, to the tenth of the unit of the lower limit, unless the context clearly dictates otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

As used herein, "anucleate cell" refers to a cell lacking a nucleus. Such cells can include, but are not limited to, platelets, red blood cells (RBCs) such as erythrocytes and reticulocytes. Reticulocytes are immature (e.g., not yet biconcave) red blood cells, typically comprising about 1% of the red blood cells in the human body. Reticulocytes are also anucleate. In certain embodiments, the systems and methods described herein are used the treatment and/or processing of enriched (e.g., comprising a greater percentage of the total cellular population than would be found in nature), purified, or isolated (e.g., from their natural environment, in substantially pure or homogeneous form) populations of anucleate cells (e.g., RBCs, reticulocytes, and/or platelets). In certain embodiments, the systems and methods described herein are used for the treatment and/or processing of whole blood containing RBCs (e.g., erythrocytes or reticulocytes), platelets as well as other blood cells. Purification or enrichment of these cell types is accomplished using known methods such as density gradient systems (e.g., Ficoll-Hypaque), fluorescence activated cell sorting (FACS), magnetic cell sorting, or in vitro differentiation of erythroblasts and erythroid precursors.

The term "vesicle" as used herein refers to a structure comprising liquid enclosed by a lipid bilayer. In some examples, the lipid bilayer is sourced from naturally existing lipid composition. In some examples, the lipid bilayer can be sourced from a cellular membrane. In some examples, vesicles can be derived from various kinds of entities, such as cells. In such examples, a vesicle can retain molecules (such as intracellular proteins or membrane components) from the originating entity. For example, a vesicle derived from a red blood cell may contain any number of intracellular proteins that were in the red blood cell and/or membrane components of the red blood cell. In some examples, a vesicle can contain any number of molecules intracellularly in addition to the desired payload.

As used herein "payload" refers to the material that is being delivered into, such as loaded in, the anucleate cell-derived vesicle (e.g., an RBC-derived vesicle). "Payload," "cargo," "delivery material," and "compound" are used interchangeably herein. In some embodiments, a payload may refer to a protein, a small molecule, a nucleic acid (e.g., RNA and/or DNA), a lipid, a carbohydrate, a macromolecule, a vitamin, a polymer, fluorescent dyes and fluorophores, carbon nanotubes, quantum dots, nanoparticles, and steroids. In some embodiments, the payload may refer to a protein or small molecule drug. In some embodiments, the payload may comprise one or more compounds.

The term "pore" as used herein refers to an opening, including without limitation, a hole, tear, cavity, aperture, break, gap, or perforation within a material. In some examples, (where indicated) the term refers to a pore within a surface of the present disclosure. In other examples, (where indicated) a pore can refer to a pore in a cell membrane.

The term "membrane" as used herein refers to a selective barrier or sheet containing pores. The term includes a pliable sheet-like structure that acts as a boundary or lining. In some examples, the term refers to a surface or filter containing pores. This term is distinct from the term "cell membrane".

The term "filter" as used herein refers to a porous article that allows selective passage through the pores. In some examples the term refers to a surface or membrane containing pores.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

The term "heterologous" as it relates to amino acid sequences such as peptide sequences and polypeptide sequences, denotes sequences that are not normally joined together, and/or are not normally associated with a particular cell. Thus, a "heterologous" region of a peptide sequence is a segment of amino acids within or attached to another amino acid molecule that is not found in association with the other molecule in nature. For example, a heterologous region of a peptide construct could include the amino acid sequence of the peptide flanked by sequences not found in association with the amino acid sequence of the peptide in nature. Another example of a heterologous peptide sequence is a construct where the peptide sequence itself is not found in nature (e.g., synthetic sequences having amino acids different as coded from the native gene). Similarly, a cell transformed with a vector that expresses an amino acid construct which is not normally present in the cell would be considered heterologous for purposes of this invention. Allelic variation or naturally occurring mutational events do not give rise to heterologous peptides, as used herein.

The term "exogenous" when used in reference to an agent, such as an antigen or an adjuvant, with relation to a cell or cell-derived vesicle refers to an agent outside of the cell or an agent delivered into the cell from outside the cell. The cell may or may not have the agent already present, and may or may not produce the agent after the exogenous agent has been delivered.

The term "homologous" as used herein refers to a molecule which is derived from the same organism. In some examples the term refers to a nucleic acid or protein which is normally found or expressed within the given organism.

As used herein, "treatment" or "treating" is an approach for obtaining beneficial or desired results, including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing or improving the quality of life, increasing weight gain, and/or prolonging survival. Also encompassed by "treatment" is a reduction of pathological consequence of cancer (such as, for example, tumor volume). The methods of the invention contemplate any one or more of these aspects of treatment.

As used herein, the term "prophylactic treatment" refers to treatment, wherein an individual is known or suspected to have or be at risk for having a disorder but has displayed no symptoms or minimal symptoms of the disorder. An individual undergoing prophylactic treatment may be treated prior to onset of symptoms. In some embodiments, an individual may be treated if they have a precancerous lesion, particularly a precancerous lesion with a Ras mutation.

As used herein, by "combination therapy" is meant that a first agent be administered in conjunction with another agent. "In conjunction with" refers to administration of one treatment modality in addition to another treatment modality, such as administration of a composition of nucleated cells as described herein in addition to administration of an immunoconjugate as described herein to the same individual. As such, "in conjunction with" refers to administration of one treatment modality before, during, or after delivery of the other treatment modality to the individual.

The term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition).

As used herein, the term "sequential administration" means that the first therapy and second therapy in a combination therapy are administered with a time separation of more than about 15 minutes, such as more than about any of 20, 30, 40, 50, 60, or more minutes. Either the first therapy or the second therapy may be administered first. The first and second therapies are contained in separate compositions, which may be contained in the same or different packages or kits.

As used herein, the term "concurrent administration" means that the administration of the first therapy and that of a second therapy in a combination therapy overlap with each other.

In the context of cancer, the term "treating" includes any or all of killing cancer cells, inhibiting growth of cancer cells, inhibiting replication of cancer cells, lessening of overall tumor burden and ameliorating one or more symptoms associated with the disease.

As used herein, the term "modulate" may refer to the act of changing, altering, varying, or otherwise modifying the presence, or an activity of, a particular target. For example, modulating an immune response may refer to any act leading to changing, altering, varying, or otherwise modifying an immune response. In some examples, "modulate" refers to enhancing the presence or activity of a particular target. In some examples, "modulate" refers to suppressing the presence or activity of a particular target. In other examples, modulating the expression of a nucleic acid may include, but not limited to a change in the transcription of a nucleic acid, a change in mRNA abundance (e.g., increasing mRNA transcription), a corresponding change in degradation of mRNA, a change in mRNA translation, and so forth.

As used herein, the term "inhibit" may refer to the act of blocking, reducing, eliminating, or otherwise antagonizing the presence, or an activity of, a particular target. Inhibition may refer to partial inhibition or complete inhibition. For example, inhibiting an immune response may refer to any act leading to a blockade, reduction, elimination, or any other antagonism of an immune response. In other examples, inhibition of the expression of a nucleic acid may include, but not limited to reduction in the transcription of a nucleic acid, reduction of mRNA abundance (e.g., silencing mRNA transcription), degradation of mRNA, inhibition of mRNA translation, gene editing and so forth. In other examples, inhibition of the expression of a protein may include, but not be limited to, reduction in the transcription of a nucleic acid encoding the protein, reduction in the stability of mRNA encoding the protein, inhibition of translation of the protein, reduction in stability of the protein, and so forth. In another example, inhibit may refer to the act of slowing or stopping growth; for example, retarding or preventing the growth of a tumor cell.

As used herein, the term "suppress" may refer to the act of decreasing, reducing, prohibiting, limiting, lessening, or otherwise diminishing the presence, or an activity of, a particular target. Suppression may refer to partial suppression or complete suppression. For example, suppressing an immune response may refer to any act leading to decreasing, reducing, prohibiting, limiting, lessening, or otherwise diminishing an immune response. In other examples, suppression of the expression of a nucleic acid may include, but not limited to reduction in the transcription of a nucleic acid, reduction of mRNA abundance (e.g., silencing mRNA transcription), degradation of mRNA, inhibition of mRNA translation, and so forth. In other examples, suppression of the expression of a protein may include, but not be limited to, reduction in the transcription of a nucleic acid encoding the protein, reduction in the stability of mRNA encoding the protein, inhibition of translation of the protein, reduction in stability of the protein, and so forth.

As used herein, the term "enhance" may refer to the act of improving, boosting, heightening, or otherwise increasing the presence, or an activity of, a particular target. For example, enhancing an immune response may refer to any act leading to improving, boosting, heightening, or otherwise increasing an immune response. In one exemplary example, enhancing an immune response may refer to employing an antigen and/or adjuvant to improve, boost, heighten, or otherwise increase an immune response. In other examples, enhancing the expression of a nucleic acid may include, but not limited to increase in the transcription of a nucleic acid, increase in mRNA abundance (e.g., increasing mRNA transcription), decrease in degradation of mRNA, increase in mRNA translation, and so forth. In other examples, enhancing the expression of a protein may include, but not be limited to, increase in the transcription of a nucleic acid encoding the protein, increase in the stability of mRNA encoding the protein, increase in translation of the protein, increase in the stability of the protein, and so forth.

As used herein, the term "induce" may refer to the act of initiating, prompting, stimulating, establishing, or otherwise producing a result. For example, inducing an immune response may refer to any act leading to initiating, prompting, stimulating, establishing, or otherwise producing a desired immune response. In other examples, inducing the expression of a nucleic acid may include, but not limited to initiation of the transcription of a nucleic acid, initiation of mRNA translation, and so forth. In other examples, inducing the expression of a protein may include, but not be limited to, increase in the transcription of a nucleic acid encoding the protein, increase in the stability of mRNA encoding the protein, increase in translation of the protein, increase in the stability of the protein, and so forth.

The term "polynucleotide" or "nucleic acid" as used herein refers to a polymeric form of nucleotides of any length, including ribonucleotides and deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. The backbone of the polynucleotide can comprise repeating units, such as N-(2-aminoethyl)-glycine, linked by peptide bonds (i.e., peptide nucleic acid). Alternatively, the backbone of the polynucleotide can comprise a polymer of synthetic subunits such as phosphoramidates and phorphorthioates and thus can be an oligodeoxynucleoside phosphoramidate (P-NH2) or a mixed phosphorothioate-phosphorodiester oligomer or a mixed phosphoramidate-phosphodiester oligomer. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

As used herein, the term "adjuvant" refers to a substance which modulates and/or engenders an immune response. Generally, the adjuvant is administered in conjunction with an antigen to effect enhancement of an immune response to the antigen as compared to antigen alone. Various adjuvants are described herein.

The terms "CpG oligodeoxynucleotide" and "CpG ODN" herein refer to DNA molecules of 10 to 30 nucleotides in length containing a dinucleotide of cytosine and guanine separated by a phosphate (also referred to herein as a "CpG" dinucleotide, or "CpG"). The CpG ODNs of the present disclosure contain at least one unmethylated CpG dinucleotide. That is, the cytosine in the CpG dinucleotide is not methylated (i.e., is not 5-methylcytosine). CpG ODNs may have a partial or complete phosphorothioate (PS) backbone.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug Administration.

For any of the structural and functional characteristics described herein, methods of determining these characteristics are known in the art.

As used herein, "microfluidic systems" refers to systems in which low volumes (e.g., m\L, nL, pL, fL) of fluids are processed to achieve the discrete treatment of small volumes of liquids. Certain implementations described herein include multiplexing, automation, and high throughput screening. The fluids (e.g., a buffer, a solution, a payload-containing solution, or a cell suspension) can be moved, mixed, separated, or otherwise processed. In certain embodiments described herein, microfluidic systems are used to apply mechanical constriction to a cell suspended in a buffer, inducing perturbations in the cell (e.g., holes) that allow a payload or compound to enter the cytosol of the cell.

As used herein, a "constriction" may refer to a portion of a microfluidic channel defined by an entrance portion, a centerpoint, and an exit portion, wherein the centerpoint is defined by a width, a length, and a depth. In other examples, a constriction may refer to a pore or may be a portion of a pore. The pore may be contained on a surface (e.g., a filter and/or membrane).

The term "Ras", as used herein refers to any member of the to a group of the small guanosine triphosphate (GTP) binding proteins known as Ras superfamily or Tas-like GTPases, and includes all homologues including those in mammals such as primates (e.g. humans), non-human primates (e.g. cynomolgus monkeys), and rodents (e.g. mice and rats), unless otherwise indicated. The term encompasses "full-length," unprocessed Ras as well as any form of Ras which results from processing in the cell. The term also encompasses wild-type occurring isoform variants of Ras, e.g., splice variants or allelic variants. In humans, three Ras genes encode highly homologous Ras proteins, H-Ras, N-Ras and K-Ras. K-RAS includes two forms: K-RasA and K-RasB. The amino acid sequence of human K-Ras is shown in UniProt (world wide web.uniprot.org) accession no. P01116 (version 241). Specifically, the amino acid sequence of human K-Ras isoform a (known as K-Ras4A) is shown in UniProt (world wide web.uniprot.org) accession no. P01116-1 (version 241) and NCBI (world wide web.ncbi.nlm.nih.gov/) RefSeq NP_203524.1. The amino acid sequence of human K-Ras isoform b (known as K-Ras4B) is shown in UniProt (world wide web.uniprot.org) accession no. P01116-2 (version 241) and NCBI (world wide web.ncbi.nlm.nih.gov/) RefSeq NP_004976.2. The N-terminal domain of human K-Ras extends from amino acid position 1 to 86.

For any of the structural and functional characteristics described herein, methods of determining these characteristics are known in the art.

Methods of Treatment of Diseases Associated with Ras Mutation

In some aspects, provided are methods for stimulating an immune response to a mutated Ras protein in an individual, the method comprising administering an effective amount of a composition comprising anucleate cell-derived vesicles (e.g. RBC-derived vesicles) to an individual, wherein the anucleate cell-derived vesicles comprise a mutated Ras antigen; wherein the mutated Ras antigen is delivered to the anucleate cell-derived vesicle intracellularly (i.e, intravesicularly). In some embodiments, the anucleate cell-derived vesicles further comprise an adjuvant. In some embodiments, the method comprises administering an effective amount of any of the compositions described herein. In some embodiments, the individual has cancer.

In some aspects, provided are methods for reducing tumor growth in an individual, the method comprising administering an effective amount of a composition comprising anucleate cell-derived vesicles (e.g. RBC-derived vesicles) to an individual, wherein the anucleate cell-derived vesicles comprise a mutated Ras antigen; wherein the mutated Ras antigen is delivered to the anucleate cell-derived vesicles intracellularly. In some embodiments, the anucleate cell-derived vesicles further comprise an adjuvant. In some embodiments, the method comprises administering an effective amount of any of the compositions described herein. In some embodiments, the individual has cancer.

In some aspects, provided are methods for vaccinating an individual in need thereof, the method comprising administering an effective amount of a composition comprising anucleate cell-derived vesicles (e.g. RBC-derived vesicles) to an individual, wherein the anucleate cell-derived vesicles comprise a mutated Ras antigen; wherein the mutated Ras antigen is delivered to the anucleate cell-derived vesicles intracellularly. In some embodiments, the anucleate cell-derived vesicles further comprises an adjuvant. In some embodiments, the method comprises administering an effective amount of any of the compositions described herein. In some embodiments, the individual has cancer.

In some aspects, provided are methods for treating cancer in an individual, the method comprising administering an effective amount of a composition comprising anucleate cell-derived vesicles (e.g. RBC-derived vesicles) to an individual, wherein the anucleate cell-derived vesicles comprise a mutated Ras antigen; wherein the mutated Ras antigen is delivered to the anucleate cell-derived vesicles intracellularly. In some embodiments, the anucleate cell-derived vesicles further comprises an adjuvant. In some embodiments, the method comprises administering an effective amount of any of the compositions described herein.

In some aspects, there is provided a method for stimulating an immune response to a mutated Ras protein in an individual, comprising: a) passing a cell suspension comprising input anucleate cells through a cell-deforming constriction, wherein a diameter of the constriction is a function of a diameter of the input anucleate cells in the suspension, thereby causing perturbations of the input anucleate cells large enough for a mutated Ras antigen or the mutated Ras antigen and an adjuvant to pass through to form perturbed input anucleate cells; b) incubating the perturbed input anucleate cells with the mutated Ras antigen or the mutated Ras antigen and the adjuvant for a sufficient time to allow the mutated Ras antigen or the mutated Ras antigen and the adjuvant to enter the perturbed input anucleate cells; thereby generating anucleate cell-derived vesicles comprising the mutated Ras antigen or the mutated Ras antigen and the adjuvant; and c) administering an effective amount of the anucleate cell-derived vesicles comprising the mutated Ras antigen or the mutated Ras antigen and the adjuvant to the individual.

In some aspects, there is provided a method for reducing tumor growth in an individual, comprising: a) passing a cell suspension comprising input anucleate cells through a cell-deforming constriction, wherein a diameter of the constriction is a function of a diameter of the input anucleate cells in the suspension, thereby causing perturbations of the input anucleate cells large enough for a mutated Ras antigen or the mutated Ras antigen and an adjuvant to pass through to form perturbed input anucleate cells; b) incubating the perturbed input anucleate cells with the mutated Ras antigen or the mutated Ras antigen and the adjuvant for a sufficient time to allow the mutated Ras antigen or the mutated Ras antigen and the adjuvant to enter the perturbed input anucleate cells; thereby generating anucleate cell-derived vesicles comprising the mutated Ras antigen or the mutated Ras antigen and the adjuvant; and c) administering an effective amount of the anucleate cell-derived vesicles comprising the mutated Ras antigen or the mutated Ras antigen and the adjuvant to the individual.

In some aspects, there is provided a method for vaccinating an individual in need thereof, comprising: a) passing a cell suspension comprising input anucleate cells through a cell-deforming constriction, wherein a diameter of the constriction is a function of a diameter of the input anucleate cells in the suspension, thereby causing perturbations of the input anucleate cells large enough for a mutated Ras antigen or the mutated Ras antigen and an adjuvant to pass through to form perturbed input anucleate cells; b) incubating the perturbed input anucleate cells with the mutated Ras antigen or the mutated Ras antigen and the adjuvant for a sufficient time to allow the mutated Ras antigen or the mutated Ras antigen and the adjuvant to enter the perturbed input anucleate cells; thereby generating anucleate cell-derived vesicles comprising the mutated Ras antigen or the mutated Ras antigen and an adjuvant; and c) administering an effective amount of the anucleate cell-derived vesicles comprising the mutated Ras antigen or the mutated Ras antigen and the adjuvant to the individual.

In some aspects, there is provided a method for treating cancer in an individual, comprising: a) passing a cell suspension comprising input anucleate cells through a cell-deforming constriction, wherein a diameter of the constriction is a function of a diameter of the input anucleate cells in the suspension, thereby causing perturbations of the input anucleate cells large enough for a mutated Ras antigen or the mutated Ras antigen and an adjuvant to pass through to form perturbed input anucleate cells; b) incubating the perturbed input anucleate cells with the mutated Ras antigen or the mutated Ras antigen and the adjuvant for a sufficient time to allow the mutated Ras antigen or the mutated Ras antigen and the adjuvant to enter the perturbed input anucleate cells; thereby generating anucleate cell-derived vesicles comprising the mutated Ras antigen or the mutated Ras antigen and the adjuvant; and c) administering an effective amount of the anucleate cell-derived vesicles comprising the mutated Ras antigen or the mutated Ras antigen and an adjuvant to the individual.

In some embodiments according to any of the methods, uses or compositions described herein, the methods comprises: a) passing a cell suspension comprising input anucleate cells through a cell-deforming constriction, wherein a diameter of the constriction is a function of a diameter of the input anucleate cells in the suspension, thereby causing perturbations of the input anucleate cells large enough for a mutated Ras antigen to pass through to form perturbed input anucleate cells; b) incubating the perturbed input anucleate cells with the mutated Ras antigen for a sufficient time to allow the mutated Ras antigen to enter the perturbed input anucleate cells; thereby generating anucleate cell-derived vesicles comprising the mutated Ras antigen; and c) administering an effective amount of the anucleate cell-derived vesicles comprising the mutated Ras antigen to the individual.

In some embodiments according to any of the methods, uses or compositions described herein, the methods comprises: a) passing a cell suspension comprising input anucleate cells through a cell-deforming constriction, wherein a diameter of the constriction is a function of a diameter of the input anucleate cells in the suspension, thereby causing perturbations of the input anucleate cells large enough for a nucleic acid encoding the mutated Ras antigen to pass through to form perturbed input anucleate cells; and b) incubating the perturbed input anucleate cells with the nucleic acid encoding the mutated Ras antigen for a sufficient time to allow the nucleic acid encoding the mutated Ras antigen to enter the perturbed input anucleate cells, wherein the nucleic acid expressed the mutated Ras antigen; thereby generating anucleate cell-derived vesicles comprising the mutated Ras antigen.

In some embodiments according to any of the methods, uses or compositions described herein, the methods comprises: a) passing a cell suspension comprising input anucleate cells through a cell-deforming constriction, wherein a diameter of the constriction is a function of a diameter of the input anucleate cells in the suspension, thereby causing perturbations of the input anucleate cells large enough for a nucleic acid encoding the mutated Ras antigen and for an adjuvant to pass through to form perturbed input anucleate cells; and b) incubating the perturbed input anucleate cells with the nucleic acid encoding the mutated Ras antigen and with the adjuvant for a sufficient time to allow the nucleic acid encoding the mutated Ras antigen and for the adjuvant to enter the perturbed input anucleate cells; wherein the nucleic acid encoding the mutated Ras antigen is expressed thereby generating anucleate cell-derived vesicles comprising the mutated Ras antigen and the adjuvant.

In some embodiments, there is provided a composition for stimulating an immune response to mutated Ras protein in an individual, wherein the composition comprises an effective amount of any one of the compositions comprising anucleate cell-derived vesicles comprising a mutated Ras antigen as described herein. In some embodiments, there is provided a composition for reducing tumor growth, wherein the composition comprises an effective amount of any one of the compositions comprising anucleate cell-derived vesicles comprising a mutated Ras antigen described herein. In some embodiments, the individual has cancer. In some embodiments, there is provided a composition for treating cancer in an individual, wherein the composition comprises an effective amount of any one of the compositions comprising anucleate cell-derived vesicles comprising a mutated Ras antigen described herein. In some embodiments, the cancer is a pancreatic cancer, a colon cancer, a small intestine cancer, a biliary tract cancer, an endometrial cancer, a lung cancer, a skin cancer, an ovarian cancer, a stomach cancer, an esophageal cancer, a cervical cancer or a urinary tract cancer.

In some embodiments, there is provided a composition for stimulating an immune response to mutated Ras protein in an individual, wherein the composition comprises an effective amount of any one of the compositions comprising anucleate cell-derived vesicles comprising a mutated Ras antigen and an adjuvant as described herein. In some embodiments, there is provided a composition for reducing tumor growth, wherein the composition comprises an effective amount of any one of the compositions comprising anucleate cell-derived vesicles comprising a mutated Ras antigen and an adjuvant described herein. In some embodiments, the individual has cancer. In some embodiments, there is provided a composition for treating cancer in an individual, wherein the composition comprises an effective amount of any one of the compositions comprising anucleate cell-derived vesicles comprising a mutated Ras antigen and an adjuvant described herein. In some embodiments, the cancer is a pancreatic cancer, a colon cancer, a small intestine cancer, a biliary tract cancer, an endometrial cancer, a lung cancer, a skin cancer, an ovarian cancer, a stomach cancer, an esophageal cancer, a cervical cancer or a urinary tract cancer.

In some embodiments, there is provided the use of a composition comprising an effective amount of anucleate cell-derived vesicles in the manufacture of a medicament for stimulating an immune response to mutated Ras protein, wherein the composition comprises an effective amount of any one of the compositions anucleate cell-derived vesicles comprising a mutated Ras antigen described herein. In some embodiments, there is provided the use of a composition comprising an effective amount of anucleate cell-derived vesicles in the manufacture of a medicament for reducing tumor growth in an individual, wherein the composition comprises an effective amount of any one of the compositions comprising anucleate cell-derived vesicles comprising a mutated Ras antigen described herein. In some embodiments, the individual has cancer. In some embodiments, there is provided the use of a composition comprising an effective amount of anucleate cell-derived vesicles in the manufacture of a medicament for treating cancer in an individual, wherein the composition comprises an effective amount any one of the compositions comprising anucleate cell-derived vesicles comprising a mutated Ras antigen described herein.

In some embodiments, there is provided the use of a composition comprising an effective amount of anucleate cell-derived vesicles in the manufacture of a medicament for stimulating an immune response to mutated Ras protein, wherein the composition comprises an effective amount of any one of the compositions anucleate cell-derived vesicles comprising a mutated Ras antigen and an adjuvant described herein. In some embodiments, there is provided the use of a composition comprising an effective amount of anucleate cell-derived vesicles in the manufacture of a medicament for reducing tumor growth in an individual, wherein the composition comprises an effective amount of any one of the compositions comprising anucleate cell-derived vesicles comprising a mutated Ras antigen and an adjuvant described herein. In some embodiments, the individual has cancer. In some embodiments, there is provided the use of a composition comprising an effective amount of anucleate cell-derived vesicles in the manufacture of a medicament for treating cancer in an individual, wherein the composition comprises an effective amount any one of the compositions comprising anucleate cell-derived vesicles comprising a mutated Ras antigen and an adjuvant described herein.

In some embodiments according to the methods, uses or compositions described herein, the individual has cancer. In some embodiments, the cancer is pancreatic cancer, colon cancer, lung cancer (including but not limited to non-small-cell lung cancer), biliary tract cancer, bladder cancer, liver cancer, myeloid leukemia and breast cancer. In some embodiments, the cancer is a pancreatic cancer, a colon cancer, a small intestine cancer, a biliary tract cancer, an endometrial cancer, a lung cancer, a skin cancer, an ovarian cancer, a stomach cancer, an esophageal cancer, a cervical cancer or a urinary tract cancer. In some embodiments, the cancer is a solid cancer. In some embodiments, the cancer is a liquid cancer. In some embodiments, the cancer is a hematologic cancer. In some embodiments, the cancer is a cancer associated with Ras mutation. In some embodiments, the mutated Ras antigen is a cancer antigen found in a cancer associated with Ras mutation. In some embodiments, the cancer is a localized cancer. In some embodiments, the cancer is a metastatic cancer.

In some embodiments, the width of the constriction is about 10% to about 99% of the mean diameter of the input anucleate cells. In some embodiments, the width of the constriction is any one of about 10% to about 90%, about 10% to about 80%, about 10% to about 70%, about 20% to about 60%, about 40% to about 60%, about 30% to about 45%, about 50% to about 99%, about 50% to about 90%, about 50% to about 80%, about 50% to about 70%, about 60% to about 90%, about 60% to about 80%, or about 60% to about 70% of the mean diameter of the input anucleate cells. In some embodiments, the width of the constriction about 0.25 μm to about 4 μm, about 1 μm to about 4 μm, about 1.2 μm to about 3 μm, about 1.4 μm to about 2.6 μm, about 1.6 μm to about 2.4 μm, or about 1.8 μm to about 2.2. In some embodiments, the width of the constriction is about 2.0 μm. In some embodiments, the width of the constriction is about 2.5 μm. In some embodiments, the width of the constriction is about 3.0 μm. In some embodiments, the width of the constriction is about or less than any one of 0.25 μm, 0.5 μm, 1.0 μm, 1.2 μm, 1.4 μm, 1.6 μm, 1.8 μm, 2.0 μm, 2.2 μm, 2.4 μm, 2.6 μm, 2.8 μm, 3.0 μm, 3.2 μm, 3.4 μm, 3.6 μm, 3.8 μm, 4.0 μm, 4.2 μm, 4.4 μm, 4.6 μm, 4.8 μm, 5.0 μm, 5.2 μm, 5.4 μm, 5.6 μm, 5.8 μm, 6.0 μm. In some embodiments, the cell suspension comprising the input anucleate cells are passed through multiple constrictions wherein the multiple constrictions are arranged in series and/or in parallel.

In some embodiments, the anucleate cell is an RBC or a platelet. In some embodiments, the anucleate cell is an erythrocyte or a reticulocyte. In some embodiments, the anucleate cell-derived vesicle is a RBC-derived vesicle or a platelet-derived vesicle. In some embodiments, the anucleate cell-derived vesicle is an erythrocyte-derived vesicle or a reticulocyte-derived vesicle.

In some embodiments, wherein the anucleate cell-derived vesicle comprises an adjuvant, the adjuvant used for conditioning is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid (poly I:C), R837, R848, a TLR3 agonist, a TLR4 agonist or a TLR9 agonist. In some embodiments, the adjuvant is polyinosinic-polycytidylic acid (poly I:C).

In some embodiments, the mutated Ras antigen is a pool of multiple polypeptides that elicit a response against the same and or different mutated Ras antigens. In some embodiments, the mutated Ras antigen is a polypeptide comprising one or more antigenic mutated Ras epitope and one or more heterologous peptide sequences. In some embodiments, the mutated Ras antigen complexes with other antigens or with an adjuvant. In some embodiments, the mutated Ras antigen comprises a G12D mutation, a G12V mutation, a G12C mutation or a G13D mutation. In some embodiments, the mutated Ras antigen is a polypeptide comprising one or more antigenic mutated Ras epitopes that is flanked on the N-terminus and/or the C-terminus by one or more heterologous peptide sequences. In some embodiments, the mutated Ras antigen is a polypeptide comprising one or more antigenic mutated Ras epitopes that is not flanked on the N-terminus and/or the C-terminus by one or more heterologous peptide sequences. In some embodiments, the mutated Ras antigen is one or more of a $G12D^{1-16}$, a $G12D^{2-19}$, a $G12D^{2-22}$, a $G12D^{2-29}$ a $G12V^{1-16}$, a $G12V^{2-19}$, a $G12V^{3-17}$, or a $G12V^{3-42}$ antigen. In some embodiments, the mutated Ras antigen comprises an amino acid sequence with at least 90% similarity to any one of SEQ ID NOs:1-8. In some embodiments, the mutated Ras antigen comprises an amino acid sequence with at least any one of: 80%, 85%, 90%, or 95% similarity to any one of SEQ ID NOs:1-8. In some embodiments, the mutated Ras antigen comprises an amino acid sequence of SEQ ID NOs:1-8. In some embodiments, the mutated Ras antigen comprises an amino acid sequence with at least 90% similarity to any one of SEQ ID NOs:9-15. In some embodiments, the mutated Ras antigen comprises an amino acid sequence of SEQ ID NOs:9-15. In some embodiments, the mutated Ras antigen is capable of being processed into an MHC class I-restricted peptide. In some embodiments, the mutated Ras antigen is capable of being processed into an MHC class II-restricted peptide.

In some embodiments, the method comprises multiple administrations of the anucleate cell-derived vesicles comprising the mutated Ras antigen. In some embodiments, the method comprises about 3 to about 9 administrations of the anucleate cell-derived vesicles comprising the mutated Ras antigen. In some embodiments, the method comprises about any one of 1, 2, 3, 4, 5, 6, 7, 8, 9, 10, 11, 12, 13, 14 or 15 administrations of the anucleate cell-derived vesicles comprising the mutated Ras antigen. In some embodiments, the method comprises continuous administrations of the anucleate cell-derived vesicles comprising the mutated Ras antigen as needed. In some embodiments, the time interval between two successive administrations of the anucleate cell-derived vesicles comprising the mutated Ras antigen is between about 1 day and about 30 days. In some embodiments, the time interval between two successive administrations of anucleate cell-derived vesicles comprising the mutated Ras antigen is about 21 days. In some embodiments, the time the time interval between two successive administrations of the anucleate cell-derived vesicles comprising the mutated Ras antigen is about any one of 1, 2, 3, 4, 5, 6, 7, 8, 10, 12, 14, 16, 20, 25, 30, 35, 40, 45, 50, 55, 60, 65, 70, 75, 80, 85, 90, 95, 100, or 150 days. In some embodiments, the time interval between the first two successive administrations of the anucleate cell-derived vesicles comprising the mutated Ras antigen is 1 day or 2 days. In some embodiments, the time interval between the first two successive administrations of the anucleate cell-derived vesicles comprising the mutated Ras antigen is 1 day or 2 days, wherein the method comprises more than 2 administration of the anucleate cell-derived vesicles comprising the mutated Ras antigen (such as but not limited to 3, 4, 5, 6, 7, 8, 9, 10, 11, 12, 13, 14, 15 or more administrations). In some embodiments, the anucleate cell-derived vesicles comprising the mutated Ras antigen are administered intravenously, intratumorally and/or subcutaneously. In some embodiments, the anucleate cell-derived vesicles comprising the mutated Ras antigen are administered intravenously.

In some embodiments, the composition further comprises an adjuvant. In some embodiments, the adjuvant is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid, R837, R848, a TLR3 agonist, a TLR4 agonist or a TLR9 agonist. In some embodiments, the adjuvant is a CpG oligodeoxynucleotide. In some embodiments, the adjuvant is poly I:C.

In some embodiments, the composition comprising the anucleate cell-derived vesicles comprising the mutated Ras antigen and the adjuvant are administered simultaneously. In some embodiments, the composition comprising anucleate cell-derived vesicles comprising the mutated Ras antigen and the adjuvant are administered sequentially. In some embodiments, the adjuvant and/or the anucleate cell-derived vesicles comprising the mutated Ras antigen are administered intravenously, intratumorally and/or subcutaneously. In some embodiments, the adjuvant and/or the anucleate cell-derived vesicles comprising the mutated Ras antigen are administered intravenously.

In some embodiments, the composition comprising anucleate cell-derived vesicles comprising the mutated Ras antigen is administered prior to administering the adjuvant. For example, the composition comprising the anucleate cell-derived vesicles comprising the mutated Ras antigen is administered from about 1 hour to about 1 week prior to administration of the adjuvant. For example, in some embodiments, the composition comprising the anucleate cell-derived vesicles comprising the mutated Ras antigen is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days prior to administration of the adjuvant. In some embodiments, the composition comprising the anucleate cell-derived vesicles comprising the mutated Ras antigen is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days prior to administration of the adjuvant.

In some embodiments, the composition comprising the anucleate cell-derived vesicles comprising the mutated Ras antigen is administered following administration of the adjuvant. For example, the composition comprising the anucleate cell-derived vesicles comprising the mutated Ras antigen is administered from about 1 hour to about 1 week following administration of the adjuvant. For example, in some embodiments, the composition comprising the anucleate cell-derived vesicles comprising the mutated Ras antigen is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days following administration of the adjuvant. In some embodiments, the composition comprising the anucleate cell-derived vesicles comprising the mutated Ras antigen is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days following administration of the adjuvant.

In some embodiments, the individual is positive for expression of HLA-A*02, HLA-A*01, HLA-A*03, HLA-A*24, HLA-A*11, HLA-A*26, HLA-A*32, HLA-A*31, HLA-A*68, HLA-A*29, HLA-A*23, HLA-B*07, HLA-B*44, HLA-B*08, HLA-B*35, HLA-B*15, HLA-B*40, HLA-B*27, HLA-B*18, HLA-B*51, HLA-B*14, HLA-B*13, HLA-B*57, HLA-B*38, HLA-C*07, HLA-C*04, HLA-C*03, HLA-C*06, HLA-C*05, HLA-C*12, HLA-C*02, HLA-C*01, HLA-C*08, or HLA-C*16.

In some embodiments according to any one of the methods, uses or compositions described herein, the anucleate cell-derived vesicles comprising the mutated Ras antigen are administered prior to, concurrently with, or following administration of a therapeutic agent. In some embodiments, the therapeutic agent comprises one or more of an immune checkpoint inhibitor, a chemotherapy, or a radiotherapy. In some embodiments, the therapeutic agent comprises one or more cytokines. In some embodiments, the therapeutic agent comprises one or more antibodies. In some embodiments, the therapeutic agent comprises one or more bispecific polypeptides used in immuno-oncology (e.g., an immunoconjugate).

Immune checkpoints are regulators of the immune system and keep immune responses in check. Immune checkpoint inhibitors can be employed to facilitate the enhancement of immune response. In some embodiments, the composition comprising the anucleate cell-derived vesicles comprising the mutated Ras antigen is administered in combination with administration of an immune checkpoint inhibitor. In some embodiments, the composition comprising the anucleate cell-derived vesicles comprising the mutated Ras antigen and the immune checkpoint inhibitor are administered simultaneously. In some embodiments, the composition comprising the anucleate cell-derived vesicles comprising the mutated Ras antigen and the immune checkpoint inhibitor are administered sequentially. In some embodiments, the immune checkpoint inhibitor and/or the anucleate cell-derived vesicles comprising the mutated Ras antigen are administered intravenously, intratumorally and/or subcutaneously. In some embodiments, the immune checkpoint inhibitor and/or the anucleate cell-derived vesicles comprising the mutated Ras antigen are administered intravenously.

In some embodiments, the composition comprising the anucleate cell-derived vesicles comprising the mutated Ras antigen is administered prior to administration of the immune checkpoint inhibitor. In some embodiments, the composition comprising the anucleate cell-derived vesicles comprising the mutated Ras antigen is administered following administration of the immune checkpoint inhibitor. For example, the composition comprising the anucleate cell-derived vesicles comprising the mutated Ras antigen is administered from about 1 hour to about 1 week prior to administration of the immune checkpoint inhibitor. For example, in some embodiments, the composition comprising the anucleate cell-derived vesicles comprising the mutated Ras antigen is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days prior to administration of the immune checkpoint inhibitor. In some embodiments, the composition comprising the anucleate cell-derived vesicles comprising the mutated Ras antigen is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days prior to administration of the immune checkpoint inhibitor.

In some embodiments, the composition comprising the anucleate cell-derived vesicles comprising the mutated Ras antigen is administered about 7 days, about 10 days, about 14 days, about 18 days, about 21 days, about 24 days, about 28 days, about 30 days, about 35 days, about 40 days, about 45 days, or about 50 days prior to administration of the immune checkpoint inhibitor. In some embodiments, the composition comprising the anucleate cell-derived vesicles comprising the mutated Ras antigen is administered from between about 7 days to about 10 days, from between about 10 days and about 14 days, from between about 14 days and about 18 days, from between about 18 days and about 21 days, from between about 21 days and about 24 days, from between about 24 days and about 28 days, from between about 28 days and about 30 days, from between about 30 days and about 35 days, from between about 35 days and about 40 days, from between about 40 days and about 45 days, or from between about 45 days and about 50 days prior to administration of the immune checkpoint inhibitor.

In some embodiments, the composition comprising the anucleate cell-derived vesicles comprising the mutated Ras antigen is administered following administration of the immune checkpoint inhibitor. For example, the composition comprising the anucleate cell-derived vesicles comprising the mutated Ras antigen is administered from about 1 hour to about 1 week following administration of the immune checkpoint inhibitor. For example, in some embodiments, the composition comprising the anucleate cell-derived vesicles comprising the mutated Ras antigen is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days following administration of the immune checkpoint inhibitor. In some embodiments, the composition comprising the anucleate cell-derived vesicles comprising the mutated Ras antigen is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days following administration of the immune checkpoint inhibitor.

In some embodiments, the composition comprising the anucleate cell-derived vesicles comprising the mutated Ras antigen is administered about 7 days, about 10 days, about 14 days, about 18 days, about 21 days, about 24 days, about 28 days, about 30 days, about 35 days, about 40 days, about 45 days, or about 50 days following administration of the immune checkpoint inhibitor. In some embodiments, the composition comprising the anucleate cell-derived vesicles comprising the mutated Ras antigen is administered from between about 7 days to about 10 days, from between about 10 days and about 14 days, from between about 14 days and about 18 days, from between about 18 days and about 21 days, from between about 21 days and about 24 days, from between about 24 days and about 28 days, from between about 28 days and about 30 days, from between about 30 days and about 35 days, from between about 35 days and about 40 days, from between about 40 days and about 45 days, or from between about 45 days and about 50 days following administration of the immune checkpoint inhibitor.

In some embodiments, the method comprises multiple administration of the composition comprising the anucleate cell-derived vesicles comprising the mutated Ras antigen and/or multiple administration of the immune checkpoint inhibitor. For example, in some embodiments, the method comprises two administrations, three administrations, four administrations, five administrations, six administrations, seven administrations, eight administrations, nine administrations, ten administrations, eleven administrations, twelve administrations, thirteen administrations, fourteen administrations, or fifteen administrations of the composition comprising the anucleate cell-derived vesicles comprising the mutated Ras antigen and/or the immune checkpoint inhibitor. For example, in some embodiments, the method comprises less than five administrations, less than ten administrations, less than fifteen administrations, less than twenty administrations, less than twenty-five administrations, less than thirty administrations, less than fifty administrations, less than seventy-five administrations, less than one hundred, or less than two hundred administrations of the composition comprising the anucleate cell-derived vesicles comprising the mutated Ras antigen and/or the immune checkpoint inhibitor.

Exemplary immune checkpoint inhibitor is targeted to, without limitation, PD-1, PD-L1, CTLA-4, LAG3, TIM-3, TIGIT, VISTA, TIM1, B7-H4 (VTCN1) or BTLA. In some embodiments, the immune checkpoint inhibitor is targeted to one or more of PD-1, PD-L1, CTLA-4, LAG3, TIM-3, TIGIT, VISTA, TIM1, B7-H4 (VTCN1) or BTLA. In some embodiments, the immune checkpoint inhibitor is one or more of: an antibody that binds to PD-1, an antibody that binds PD-L1, an antibody that binds CTLA-4, an antibody that binds LAG3, or an antibody that binds TIM-3, an antibody that binds TIGIT, an antibody that binds VISTA, an antibody that binds TIM-1, an antibody that binds B7-H4, or an antibody that binds BTLA. In further embodiments, the antibody can be a full length antibody or any variants, for example but not limited to, an antibody fragment, a single chain variable fragment (ScFv), or a fragment antigen-binding (Fab). In further embodiments, the antibody can be bispecific, trispecific or multispecific. In some embodiments, the immune checkpoint inhibitor is one or more chemical compounds that binds to and/or inhibits one or more of PD-1, PD-L1, CTLA-4, LAG3, TIM-3, TIGIT, VISTA, TIM1, B7-H4 (VTCN1) or BTLA. In some embodiments, the immune checkpoint inhibitor is one or more peptides that binds to and/or inhibits one or more of PD-1, PD-L1, CTLA-4, LAG3, TIM-3, TIGIT, VISTA, TIM1, B7-H4 (VTCN1) or BTLA. In some embodiments, the immune checkpoint inhibitor is targeted to PD-1. In some embodiments, the immune checkpoint inhibitor is targeted to PD-L1.

Cytokines can be used in combination with any one of the compositions of anucleate cell-derived vesicles comprising the mutated Ras antigen described herein to achieve additive or synergistic effects against cancers, for example, mutated Ras-associated cancers. In some embodiments, the composition comprising the anucleate cell-derived vesicles comprising the mutated Ras antigen is administered in combination with administration of one or more cytokines. In some embodiments, the composition comprising the anucleate cell-derived vesicles comprising the mutated Ras antigen and the cytokine are administered simultaneously. In some embodiments, the composition comprising the anucleate cell-derived vesicles comprising the mutated Ras antigen and the cytokine are administered sequentially.

In some embodiments, the composition comprising the anucleate cell-derived vesicles comprising the mutated Ras antigen is administered prior to administration of the cytokine. In some embodiments, the composition comprising the anucleate cell-derived vesicles comprising the mutated Ras antigen is administered following administration of the cytokine. For example, the composition comprising the anucleate cell-derived vesicles comprising the mutated Ras antigen is administered from about 1 hour to about 1 week prior to administration of the cytokine. For example, in some embodiments, the composition comprising the anucleate cell-derived vesicles comprising the mutated Ras antigen is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days prior to administration of the cytokine. In some embodiments, the composition comprising the anucleate cell-derived vesicles comprising the mutated Ras antigen is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days prior to administration of the cytokine.

In some embodiments, the composition comprising the anucleate cell-derived vesicles comprising the mutated Ras antigen is administered about 7 days, about 10 days, about 14 days, about 18 days, about 21 days, about 24 days, about 28 days, about 30 days, about 35 days, about 40 days, about 45 days, or about 50 days prior to administration of the cytokine. In some embodiments, the composition comprising the anucleate cell-derived vesicles comprising the mutated Ras antigen is administered from between about 7 days to about 10 days, from between about 10 days and about 14 days, from between about 14 days and about 18 days, from between about 18 days and about 21 days, from between about 21 days and about 24 days, from between about 24 days and about 28 days, from between about 28 days and about 30 days, from between about 30 days and about 35 days, from between about 35 days and about 40 days, from between about 40 days and about 45 days, or from between about 45 days and about 50 days prior to administration of the cytokine.

In some embodiments, the composition comprising the anucleate cell-derived vesicles comprising the mutated Ras antigen is administered following administration of the cytokine. For example, the composition comprising the anucleate cell-derived vesicles comprising the mutated Ras antigen is administered from about 1 hour to about 1 week following administration of the cytokine. For example, in some embodiments, the composition comprising the anucleate cell-derived vesicles comprising the mutated Ras antigen is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days following administration of the cytokine. In some embodiments, the composition comprising the anucleate cell-derived vesicles comprising the mutated Ras antigen is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days following administration of the cytokine.

Exemplary cytokines include but are not limited to chemokines, interferons, interleukins, lymphokines, and tumor necrosis factors, or functional derivatives thereof. In some embodiments, the cytokine enhances cellular immune responses. In some embodiments, the cytokine enhances antibody responses. In some embodiments, the cytokine is a type I cytokine. In some embodiments, the cytokine is a type 2 cytokine. In some embodiments, the cytokine comprises one or more of: IL-2, IL-15, IL-10, IL-12, IFN-α, or IL-21. In some embodiments, the cytokine comprises IL-15.

In some embodiments, the composition comprising the nucleated cells comprising the mutated Ras antigen is administered prior to administration of a bispecific polypeptide comprising a cytokine moiety. In some embodiments, the composition comprising the nucleated cells comprising the mutated Ras antigen is administered prior to administration of a bispecific polypeptide comprising a cytokine moiety and an immune checkpoint inhibitor moiety. In some embodiments, the bispecific polypeptide comprises a CD3 targeting moiety and a tumor antigen targeting moiety. In some embodiments, the bispecific polypeptide comprises moieties that target two immune checkpoints. In some embodiments, the bispecific polypeptide comprises a moiety that targets antigens found in stroma or expressed on cancer-associated fibroblasts. In some embodiments, the bispecific polypeptide comprises a moiety that targets antigens found in stroma or expressed on cancer-associated fibroblasts and a cytokine moiety.

Chemotherapy can be used in combination with any one of the compositions of anucleate cell-derived vesicles comprising the mutated Ras antigen described herein to achieve additive or synergistic effects against cancers, for example, Ras-associated cancers. In some embodiments, the composition comprising the anucleate cell-derived vesicles comprising the mutated Ras antigen is administered in combination with administration of a chemotherapy. In some embodiments, the composition comprising the anucleate cell-derived vesicles comprising the mutated Ras antigen and the chemotherapy are administered simultaneously. In some embodiments, the composition comprising the anucleate cell-derived vesicles comprising the mutated Ras antigen and the chemotherapy are administered sequentially.

In some embodiments, the composition comprising the anucleate cell-derived vesicles comprising the mutated Ras antigen is administered prior to administration of the chemotherapy. In some embodiments, the composition comprising the anucleate cell-derived vesicles comprising the mutated Ras antigen is administered following administration of the chemotherapy. For example, the composition comprising the anucleate cell-derived vesicles comprising the mutated Ras antigen is administered from about 1 hour to about 1 week prior to administration of the chemotherapy. For example, in some embodiments, the composition comprising the anucleate cell-derived vesicles comprising the mutated Ras antigen is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days prior to administration of the chemotherapy. In some embodiments, the composition comprising the anucleate cell-derived vesicles comprising the mutated Ras antigen is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days prior to administration of the chemotherapy.

In some embodiments, the composition comprising the anucleate cell-derived vesicles comprising the mutated Ras antigen is administered following administration of the chemotherapy. For example, the composition comprising the anucleate cell-derived vesicles comprising the mutated Ras antigen is administered from about 1 hour to about 1 week following administration of the chemotherapy. For example, in some embodiments, the composition comprising the anucleate cell-derived vesicles comprising the mutated Ras antigen is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days following administration of the chemotherapy. In some embodiments, the composition comprising the anucleate cell-derived vesicles comprising the mutated Ras antigen is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days following administration of the chemotherapy.

In some embodiments, the composition comprising the anucleate cell-derived vesicles comprising the mutated Ras antigen is administered about 7 days, about 10 days, about 14 days, about 18 days, about 21 days, about 24 days, about 28 days, about 30 days, about 35 days, about 40 days, about 45 days, or about 50 days following administration of the chemotherapy. In some embodiments, the composition comprising the anucleate cell-derived vesicles comprising the mutated Ras antigen is administered from between about 7 days to about 10 days, from between about 10 days and about 14 days, from between about 14 days and about 18 days, from between about 18 days and about 21 days, from between about 21 days and about 24 days, from between about 24 days and about 28 days, from between about 28 days and about 30 days, from between about 30 days and about 35 days, from between about 35 days and about 40 days, from between about 40 days and about 45 days, or from between about 45 days and about 50 days following administration of the chemotherapy.

In some embodiments, the method comprises multiple administration of the composition comprising the anucleate cell-derived vesicles comprising the mutated Ras antigen and/or multiple administration of the chemotherapy. For example, in some embodiments, the method comprises two administrations, three administrations, four administrations, five administrations, six administrations, seven administrations, eight administrations, nine administrations, ten administrations, eleven administrations, twelve administrations, thirteen administrations, fourteen administrations, or fifteen administrations of the composition comprising the anucleate cell-derived vesicles comprising the mutated Ras antigen and/or the chemotherapy. For example, in some embodiments, the method comprises less than five administrations, less than ten administrations, less than fifteen administrations, less than twenty administrations, less than twenty-five administrations, less than thirty administrations, less than fifty administrations, less than seventy-five administrations, less than one hundred, or less than two hundred administrations of the composition comprising the anucleate cell-derived vesicles comprising the mutated Ras antigen and/or the chemotherapy.

Exemplary chemotherapy can be cell cycle dependent or cell cycle independent. In some embodiments, the chemotherapy comprises one or more chemotherapeutic agents. In some embodiments, a chemotherapeutic agent can target one or more of cell division, DNA, or metabolism in cancer. In some embodiments, the chemotherapeutic agent is a platinum-based agent, such as but not limited to cisplatin, oxaliplatin or carboplatin. In some embodiments, the chemotherapeutic agent is a taxane (such as docetaxel or paclitaxel). In some embodiments, the chemotherapeutic agent is 5-fluorouracil, doxorubicin, or irinotecan. In some embodiments, the chemotherapeutic agent is one or more of: an alkylating agent, an antimetabolite, an antitumor antibiotic, a topoisomerase inhibitor or a mitotic inhibitor. In some embodiments, the chemotherapy comprises cisplatin.

Radiotherapy can be used in combination with any one of the compositions of anucleate cell-derived vesicles comprising the mutated Ras antigen described herein to achieve additive or synergistic effects against cancers, for example, Ras-associated cancers. In some embodiments, the composition comprising the anucleate cell-derived vesicles comprising the mutated Ras antigen is administered in combination with administration of a radiotherapy. In some embodiments, the composition comprising the anucleate cell-derived vesicles comprising the mutated Ras antigen and the radiotherapy are administered simultaneously. In some embodiments, the composition comprising the anucleate cell-derived vesicles comprising the mutated Ras antigen and the radiotherapy are administered sequentially. In some embodiments, the composition comprising the anucleate cell-derived vesicles comprising the mutated Ras antigen is administered in combination with administration of a radiotherapy, in combination with a chemotherapy, and/or in combination with an immune checkpoint inhibitor.

In some embodiments, the composition comprising the anucleate cell-derived vesicles comprising the mutated Ras antigen is administered prior to administration of the radiotherapy. In some embodiments, the composition comprising the anucleate cell-derived vesicles comprising the mutated Ras antigen is administered following administration of the radiotherapy. For example, the composition comprising the anucleate cell-derived vesicles comprising the mutated Ras antigen is administered from about 1 hour to about 1 week prior to administration of the radiotherapy. For example, in some embodiments, the composition comprising the anucleate cell-derived vesicles comprising the mutated Ras antigen is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days prior to administration of the radiotherapy. In some embodiments, the composition comprising the anucleate cell-derived vesicles comprising the mutated Ras antigen is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days prior to administration of the radiotherapy.

In some embodiments, the composition comprising the anucleate cell-derived vesicles comprising the mutated Ras antigen is administered following administration of the radiotherapy. For example, the composition comprising the anucleate cell-derived vesicles comprising the mutated Ras antigen is administered from about 1 hour to about 1 week following administration of the radiotherapy. For example, in some embodiments, the composition comprising the anucleate cell-derived vesicles comprising the mutated Ras antigen is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days following administration of the radiotherapy. In some embodiments, the composition comprising the anucleate cell-derived vesicles comprising the mutated Ras antigen is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days following administration of the radiotherapy.

In some embodiments, the composition comprising the anucleate cell-derived vesicles comprising the mutated Ras antigen is administered about 7 days, about 10 days, about 14 days, about 18 days, about 21 days, about 24 days, about 28 days, about 30 days, about 35 days, about 40 days, about 45 days, or about 50 days following administration of the radiotherapy. In some embodiments, the composition comprising the anucleate cell-derived vesicles comprising the mutated Ras antigen is administered from between about 7 days to about 10 days, from between about 10 days and about 14 days, from between about 14 days and about 18 days, from between about 18 days and about 21 days, from between about 21 days and about 24 days, from between about 24 days and about 28 days, from between about 28 days and about 30 days, from between about 30 days and about 35 days, from between about 35 days and about 40 days, from between about 40 days and about 45 days, or from between about 45 days and about 50 days following administration of the radiotherapy.

In some embodiments, the method comprises multiple administration of the composition comprising the anucleate cell-derived vesicles comprising the mutated Ras antigen and/or multiple administration of the radiotherapy. For example, in some embodiments, the method comprises two administrations, three administrations, four administrations, five administrations, six administrations, seven administrations, eight administrations, nine administrations, ten administrations, eleven administrations, twelve administrations, thirteen administrations, fourteen administrations, or fifteen administrations of the composition comprising the anucleate cell-derived vesicles comprising the mutated Ras antigen and/or the radiotherapy. For example, in some embodiments, the method comprises less than five administrations, less than ten administrations, less than fifteen administrations, less than twenty administrations, less than twenty-five administrations, less than thirty administrations, less than fifty administrations, less than seventy-five administrations, less than one hundred, or less than two hundred administrations of the composition comprising the anucleate cell-derived vesicles comprising the mutated Ras antigen and/or the radiotherapy.

In some embodiments, there is provided a plurality of anucleate cell-derived vesicles (e.g. RBC-derived vesicles) comprising a mutated Ras antigen for use in a method of stimulating an immune response in an individual according to any one of the methods described herein.

Ras Antigens

In some embodiments, provided are methods for stimulating an immune response in an individual to a mutated Ras protein, the method comprising a) administering an effective amount of a composition comprising anucleate cell-derived vesicles (e.g. RBC-derived vesicles) to an individual, wherein the anucleate cell-derived vesicles comprise a constriction-delivered mutated Ras antigen intracellularly.

In some embodiments, the mutated Ras antigen comprise one or more mutations compared to the corresponding wild type Ras protein. In some embodiments, the mutated Ras antigen is a mutated K-Ras antigen (e.g, mutated K-Ras4A or mutated K-Ras4B), a mutated H-Ras antigen, or a mutated N-Ras antigen. In some embodiments, the mutated Ras antigen is a disease-associated antigen (such as cancer-associated antigen). In some embodiments, the mutated Ras antigen is derived from peptides or mRNA isolated from a diseased cell (such as cancer cells). In some embodiments, the mutated Ras antigen is a non-self antigen. In some embodiments, the mutated Ras antigen is derived from a lysate, such as a lysate of disease cells. In some embodiments, the mutated Ras antigen is derived from a tumor lysate. In some embodiments, the mutated Ras antigen is a tumor antigen or a tumor associated antigen. In some embodiments, the mutated Ras antigen is associated with a cancer. In some embodiments, the cancer is a pancreatic cancer, a colon cancer, a small intestine cancer, a biliary tract cancer, an endometrial cancer, a lung cancer, a skin cancer, an ovarian cancer, a stomach cancer, an esophageal cancer, a cervical cancer or a urinary tract cancer. In some embodiments, the mutated Ras antigen is a pancreatic cancer antigen, a colon cancer antigen, a small intestine cancer antigen, a biliary tract cancer antigen, an endometrial cancer antigen, a lung cancer antigen, a skin cancer antigen, an ovarian cancer antigen, a stomach cancer antigen, an esophageal cancer antigen, a cervical cancer antigen or a urinary tract cancer antigen. In some embodiments, the cancer is a solid cancer. In some embodiments, the cancer is a liquid cancer.

In some embodiments, the cancer is a hematologic cancer. In some embodiments, the cancer is a virus-associated cancer. In some embodiments, the mutated Ras antigen is a cancer antigen found in a Ras-associated cancer. In some embodiments, the cancer is a localized cancer. In some embodiments, the cancer is a metastatic cancer.

In some embodiments according to the methods described herein, the mutated Ras antigen comprises one or more proteins. In some embodiments, the mutated Ras antigen is encoded by one or more nucleic acids and enters the anucleate cells in the form of one or more nucleic acids, such as but not limited to DNAs, cDNAs, mRNAs, and plasmids. In some embodiments, the mutated Ras antigen is encoded by one or more mRNAs and enters the anucleate cells in the form of one or more mRNAs.

K-Ras belongs to a group of small guanosine triphosphate (GTP) binding proteins, known as RAS superfamily or RAS-like GTPases. Members of RAS superfamily are divided into families and subfamilies based on their structure, sequence and function. In humans, three RAS genes encode highly homologous RAS proteins, H-Ras, N-Ras and K-Ras. Ras is one of the most frequently mutated oncogenes in human cancer, and K-Ras is the isoform most frequently mutated, which constitutes 86% of RAS mutations. The K-Ras-4B splice variant is the dominant isoform with mutations in human cancers, and it is present in approximately 90% of pancreatic cancers, 30% to 40% of colon cancers, and 15% to 20% of lung cancers, mostly non-small-cell lung cancer (NSCLC). It is also present in biliary tract malignancies, endometrial cancer, cervical cancer, bladder cancer, liver cancer, myeloid leukemia and breast cancer. The mutations found most frequently in the K-Ras gene are primarily at codons 12, 13, or 61. K-Ras mutations also occur in codons 63, 117, 119, and 146 but with less frequency. In details, mutation of glycine 12 (G12) causes RAS activation by interfering with GAP binding and GAP-stimulated GTP hydrolysis. Mutations at residue 13 sterically clash with the arginine and decrease GAP binding and hydrolysis. Mutations at residues 12, 13 and 61 were reported to decrease the affinity for the RAS-binding domain (RBD) of RAF as well but with different extent. In some embodiments, the mutated Ras antigen is a mutated K-Ras antigen, a mutated H-Ras antigen, and/or a mutated N-Ras antigen. In some embodiments, the mutated K-Ras antigen is a mutated K-Ras-4A antigen, and/or a K-Ras-4B antigen.

In some embodiments, the mutated Ras antigen is a pool of multiple polypeptides that elicit a response against the same and or different mutated Ras antigens. In some embodiments, an antigen in the pool of multiple antigens does not decrease the immune response directed toward other antigens in the pool of multiple antigens. In some embodiments, the mutated Ras antigen is a polypeptide comprising an antigenic mutant Ras epitope and one or more heterologous peptide sequences. In some embodiments, the mutated Ras antigen complexes with itself, with other antigens, or with the adjuvant. In some embodiments, the mutated Ras antigen is comprised of an HLA-A2-specific epitope. In some embodiments, the mutated Ras antigen is comprised of an HLA-A11-specific epitope. In some embodiments, the mutated Ras antigen is comprised of an HLA-B7-specific epitope. In some embodiments, the mutated Ras antigen is comprised of an HLA-C8-specific epitope. In some embodiments, the mutated Ras antigen is a mutated Ras antigen comprising an mutation in its N-terminus. In some embodiments, the mutated Ras antigen is a mutated Ras antigen comprising one or more of a G12D mutation, a G12V mutation, a G12C mutation, or a G13D mutation. In some embodiments, the mutated Ras antigen comprises part or all of the N-terminal domain of a full-length mutated Ras protein. As used herein, a mutant Ras protein (such as mutant K-Ras) having its 12th residue in the N-terminal domain mutated from Glycine (G) to Aspartic Acid (D) is referred to as Ras-G12D. As used herein, a mutant K-Ras protein having its 12th residue in the N-terminal domain mutated from Glycine (G) to Aspartic Acid (D) is referred to as K-Ras-G12D. As used herein, a mutant Ras protein (such as mutant K-Ras) having its 12th residue in the N-terminal domain mutated from (G) to Valine (V) is referred to as Ras-G12V. As used herein, a mutant K-Ras protein having its 12th residue in the N-terminal domain mutated from Glycine (G) to Valine (V) is referred to as K-Ras-G12V. As used herein, a mutant Ras protein (such as mutant K-Ras) having its 12th residue in the N-terminal domain mutated from (G) to Cysteine (C) is referred to as Ras-G12C. As used herein, a mutant K-Ras protein having its 12th residue in the N-terminal domain mutated from Glycine (G) to Cysteine (C) is referred to as K-Ras-G12C. As used herein, a mutant Ras protein (such as mutant K-Ras) having its 13th residue in the N-terminal domain mutated from Glycine (G) to Aspartic Acid (D) is referred to as Ras-G13D. As used herein, a mutant K-Ras protein having its 13th residue in the N-terminal domain mutated from Glycine (G) to Aspartic Acid (D) is referred to as K-Ras-G13D.

In some embodiments, the sequence of an antigen or an antigenic epitope comprising residue X to residue Y of the N-terminal domain of a mutant Ras-G12D protein is referred to as $G12D^{X-Y}$ or Ras-$G12D^{X-Y}$. As a non-limiting example, the sequence of an antigen or an antigen epitope comprising residue 1 to residue 16 of the N-terminal domain of a mutant K-Ras-G12D protein is referred to as $G12D^{1-16}$ or K-Ras-$G12D^{1-16}$. In some embodiments, the sequence of an antigen or an antigenic epitope comprising residue X to residue Y of the N-terminal domain of a mutant Ras-G12V protein is referred to as $G12V^{X-Y}$ or Ras-$G12V^{X-Y}$. As a non-limiting example, the sequence of an antigen or an antigenic epitope comprising residue 2 to residue 22 of the N-terminal domain of a mutant K-Ras-G12V protein is referred to as $G12V^{2-22}$ or K-Ras-$G12V^{2-22}$. The same principal applies to any disclosure of $G12C^{X-Y}$ or Ras-$G12D^{X-Y}$, or wild-type $Ras^{X-Y}$ described herein.

In some embodiments, the mutated Ras antigen comprises one or more of: a peptide derived from K-Ras comprising of a G12D mutation (K-Ras-G12D), a peptide from K-Ras comprising a G12V mutation (K-Ras-G12V), a peptide from K-Ras comprising a G12C mutation (K-Ras-G12C), or a peptide from K-Ras comprising a G13D mutation (K-Ras-G13D). In some embodiments, the antigen comprises an HLA-A2-restricted peptide derived from K-Ras-G12D, an HLA-A2-restricted peptide derived from K-Ras-G12V, an HLA-A2-restricted peptide derived from K-Ras-G12C, and/or an HLA-A2-restricted peptide derived from K-Ras-G13D. In some embodiments, the antigen comprises a $G12D^{1-16}$, a $G12D^{2-19}$, a $G12D^{2-22}$, a $G12D^{2-29}$ $G12V^{1-16}$, a $G12V^{2-19}$, a $G12V^{3-17}$, or a $G12V^{3-42}$ sequence. In some embodiments, the HLA-A2-restricted peptide comprises the amino acid sequence of any one of SEQ ID NOs:1-8. In some embodiments, the mutated Ras antigen comprises an amino acid sequence with at least 90% similarity to any one of SEQ ID NOs:1-8. In some embodiments, the mutated Ras antigen comprises an amino acid sequence from the N-terminal domain of the corresponding mutated K-Ras protein (e.g. K-Ras-G12D, K-Ras-G12V, K-Ras-G12C, or K-Ras-G13D). In some embodiments, the mutated Ras antigen is one or more of a $G12D^{1-16}$, a $G12D^{2-19}$, a $G12D^{2-22}$, or a $G12D^{2-29}$, a $G12V^{1-16}$, a $G12V^{2-19}$, a $G12V^{3-17}$, or a $G12V^{3-42}$ antigen. In some embodiments, the N-terminal domain is identical in the three Ras isoforms of K-Ras, N-Ras and H-Ras. In some embodiments, wherein the mutated Ras antigen is a mutated K-Ras antigen, the mutated K-Ras antigen comprises an amino acid sequence from the N-terminal domain of the corresponding mutated K-Ras protein (e.g. K-Ras-G12D, K-Ras-G12V, K-Ras-G12C, or K-Ras-G13D), which is the same as the amino acid sequence from the N-terminal domain of the corresponding mutated H-Ras protein (e.g. H-Ras-G12D or H-Ras-G12V) or mutated N-Ras protein (e.g. N-Ras-G12D, K-Ras-G12V, K-Ras-G12C, or K-Ras-G13D). In some embodiments, the mutated Ras antigen comprises an amino acid sequence with at least 90% similarity to SEQ ID NO: 1-8. In some embodiments, the mutated Ras antigen comprises an amino acid sequence with at least any one of: 80%, 85%, 90%, or 95%, similarity to any one of SEQ ID NOs:1-8. In some embodiments, the mutated Ras antigen comprises an amino acid sequence with at least 90% similarity to SEQ ID NO:1. In some embodiments, the mutated Ras antigen comprises the amino acid sequence of SEQ ID NO:2. In a some embodiment, the mutated Ras antigen comprises the amino acid sequence of SEQ ID NO:3. In some embodiments, the mutated Ras antigen comprises the amino acid sequence of SEQ ID NO:4. In a some embodiments, the mutated Ras antigen comprises the amino acid sequence of SEQ ID NO:5. In a some embodiments, the mutated Ras antigen comprises the amino acid sequence of SEQ ID NO:6. In a some embodiments, the mutated Ras antigen consists of the amino acid sequence of SEQ ID NO:7. In a some embodiments, the mutated Ras antigen consists of the amino acid sequence of SEQ ID NO:8. In some embodiments, the mutated Ras antigen comprises the amino acid sequence of any one of SEQ ID NOs:9-15. In some embodiments, the mutated Ras antigen is a plurality of mutated Ras epitopes. In some embodiments, the mutated Ras antigen is a plurality of mutated Ras epitopes comprising at least one of the amino acid sequences of any one of SEQ ID NOs:9-15. In some embodiments, the mutated Ras antigen comprises a plurality of Ras epitopes wherein the mutated Ras antigen comprises about 9 to about 200 amino acids. In some embodiments, the mutated Ras antigen is a plurality of antigens comprising at least one of the amino acid sequences of any one of SEQ ID NOs:1-8. In some embodiments, the mutated Ras antigen comprises about 9 to about 200 amino acids. In some embodiments, the mutated Ras antigen is a plurality of antigens comprising 2, 3, 4, 5, 6, 7 or 8 of the amino acid sequences of any one of SEQ ID Nos:1-8. In some embodiments, the plurality of antigens is contained within a pool of non-covalently linked peptides. In some embodiments, the plurality of antigens is contained within a pool of non-covalently linked peptides, wherein each peptide comprises no more than one antigen.

In some embodiments according to any one of the methods described herein, the anucleate cell-derived vesicles (e.g., RBC-derived vesicles) comprise a plurality of Ras antigens that comprise a plurality of immunogenic epitopes. In further embodiments, following administration to an individual of the anucleate cell-derived vesicles comprising the plurality of antigens that comprise the plurality of immunogenic epitopes, none of the plurality of immunogenic epitopes decreases an immune response in the individual to any of the other immunogenic epitopes. In some embodiments, the Ras antigen is a polypeptide and the immunogenic epitope is an immunogenic peptide epitope. In some embodiments, the immunogenic peptide epitope is fused to an N-terminal flanking polypeptide and/or a C-terminal flanking polypeptide. In some embodiments, the mutant Ras antigen is a polypeptide comprising an immunogenic peptide epitope and one or more heterologous peptide sequences. In some embodiments, the mutant Ras antigen is a polypeptide comprising an immunogenic peptide epitope that is flanked on the N-terminus and/or the C-terminus by heterologous peptide sequences. In some embodiments, the flanking heterologous peptide sequences are derived from disease-associated immunogenic peptides. In some embodiments, the flanking heterologous peptide sequences are non-naturally occurring sequence. In some embodiments, the flanking heterologous peptide sequences are derived from an immunogenic synthetic long peptide (SLP). In some embodiments, the mutated Ras antigen is capable of being processed into an MHC class I-restricted peptide and/or an MHC class II-restricted peptide.

Methods of Generating Compositions of Anucleate Cell-Derived Vesicles Comprising Mutated Ras Antigen In some aspects, provided are methods for generating a composition of anucleate cell-derived vesicles comprising a mutated Ras antigen, wherein the mutated Ras antigen is delivered to the anucleate cell-derived vesicles intracellularly. In some embodiments, there is provided a method for generating a composition of anucleate cell-derived vesicles comprising a mutated Ras-G12D antigen, wherein the mutated Ras-G12D antigen is delivered to the anucleate cell-derived vesicles intracellularly. In some embodiments, there is provided a method for generating a composition of anucleate cell-derived vesicles comprising a mutated Ras-G12V antigen, wherein the mutated Ras-G12V antigen is delivered to the anucleate cell-derived vesicles intracellularly. In some embodiments, there is provided a method for generating a composition of anucleate cell-derived vesicles comprising a mutated Ras-G12C antigen, wherein the mutated Ras-G12C antigen is delivered to the anucleate cell-derived vesicles intracellularly. In some embodiments, there is provided a method for generating a composition of anucleate cell-derived vesicles comprising a mutated Ras-G13D antigen, wherein the mutated Ras-G13D antigen is delivered to the anucleate cell-derived vesicles intracellularly. In some embodiments, there is provided a method for generating a composition of anucleate cell-derived vesicles comprising a mutated Ras antigen, wherein the mutated Ras antigen is delivered to the anucleate cell-derived vesicles intracellularly, wherein the Ras antigen comprises the amino acid sequence of any one of SEQ ID Nos:1-15.

In some aspects, there is provided a method for generating a composition of anucleate cell-derived vesicles comprising a mutated Ras antigen, comprising: a) passing a cell suspension comprising input anucleate cells through a cell-deforming constriction, wherein a diameter of the constriction is a function of a diameter of the input anucleate cells in the suspension, thereby causing perturbations of the input anucleate cells large enough for the mutated Ras antigen to pass through to form perturbed input anucleate cells; and b) incubating the perturbed input anucleate cells with the mutated Ras antigen for a sufficient time to allow the mutated Ras antigen to enter the perturbed input anucleate cells; thereby generating anucleate cell-derived vesicles comprising the mutated Ras antigen. In some embodiments, the mutated Ras antigen is a mutated K-Ras antigen. In some embodiments, the mutated Ras antigen comprises the amino acid sequence of any one of SEQ ID Nos:1-15 In some embodiments, the mutated Ras antigen comprises an amino acid sequence with at least 90% identity to any one of SEQ ID Nos:1-15.

In some aspects, there is provided a method for generating a composition of anucleate cell-derived vesicles comprising a mutated Ras antigen, or a mutated Ras antigen and an adjuvant, comprising: a) passing a cell suspension comprising input anucleate cells through a cell-deforming constriction, wherein a diameter of the constriction is a function of a diameter of the input anucleate cells in the suspension, thereby causing perturbations of the input anucleate cells large enough for the mutated Ras antigen or the mutated Ras antigen and an adjuvant to pass through to form perturbed input anucleate cells; and b) incubating the perturbed input anucleate cells with the mutated Ras antigen or the mutated Ras antigen and the adjuvant for a sufficient time to allow the mutated Ras antigen or the mutated Ras antigen and the adjuvant to enter the perturbed input anucleate cells; thereby generating anucleate cell-derived vesicles comprising the mutated Ras antigen or the mutated Ras antigen and the adjuvant. In some embodiments, the mutated Ras antigen is a mutated K-Ras antigen. In some embodiments, the mutated Ras antigen comprises the amino acid sequence of any one of SEQ ID Nos:9-15. In some embodiments, the mutated Ras antigen comprises an amino acid sequence with at least 90% identity to any one of SEQ ID Nos:9-15. In some embodiments, the mutated Ras antigen comprises the amino acid sequence of any one of SEQ ID Nos:1-8. In some embodiments, the mutated Ras antigen comprises an amino acid sequence with at least 90% identity to any one of SEQ ID Nos:1-8.

In some aspects, there is provided a method for generating a composition of anucleate cell-derived vesicles comprising a mutated Ras antigen, comprising: a) passing a cell suspension comprising input anucleate cells through a cell-deforming constriction, wherein a diameter of the constriction is a function of a diameter of the input anucleate cells in the suspension, thereby causing perturbations of the input anucleate cells large enough for a nucleic acid encoding the mutated Ras antigen to pass through to form perturbed input anucleate cells; and b) incubating the perturbed input anucleate cells with the nucleic acid encoding the mutated Ras antigen for a sufficient time to allow the nucleic acid encoding the mutated Ras antigen to enter the perturbed input anucleate cells; wherein the nucleic acid encoding the mutated Ras antigen is expressed thereby generating anucleate cell-derived vesicles comprising the mutated Ras antigen. In some aspects, there is provided a method for generating a composition of anucleate cell-derived vesicles comprising a mutated Ras antigen and an adjuvant, comprising: a) passing a cell suspension comprising input anucleate cells through a cell-deforming constriction, wherein a diameter of the constriction is a function of a diameter of the input anucleate cells in the suspension, thereby causing perturbations of the input anucleate cells large enough for a nucleic acid encoding the mutated Ras antigen and for an adjuvant to pass through to form perturbed input anucleate cells; and b) incubating the perturbed input anucleate cells with the nucleic acid encoding the mutated Ras antigen and with the adjuvant for a sufficient time to allow the nucleic acid encoding the mutated Ras antigen and for the adjuvant to enter the perturbed input anucleate cells; wherein the nucleic acid encoding the mutated Ras antigen is expressed thereby generating anucleate cell-derived vesicles comprising the mutated Ras antigen and the adjuvant. In some embodiments, the mutated Ras antigen is a mutated K-Ras antigen. In some embodiments, the mutated Ras antigen comprises the amino acid sequence of any one of SEQ ID Nos:9-15. In some embodiments, the mutated Ras antigen comprises an amino acid sequence with at least 90% identity to any one of SEQ ID Nos:9-15. In some embodiments, the mutated Ras antigen comprises the amino acid sequence of any one of SEQ ID Nos:1-8. In some embodiments, the mutated Ras antigen comprises an amino acid sequence with at least 90% identity to any one of SEQ ID Nos:1-8.

In some embodiments, the anucleate cell is an RBC or a platelet. In some embodiments, the anucleate cell is an erythrocyte or a reticulocyte. In some embodiments, the anucleate cell-derived vesicle is a RBC-derived vesicle or a platelet-derived vesicle. In some embodiments, the anucleate cell-derived vesicle is an erythrocyte-derived vesicle or a reticulocyte-derived vesicle.

In some embodiments, the width of the constriction is about 10% to about 99% of the mean diameter of the input anucleate cells. In some embodiments, the width of the constriction is any one of about 10% to about 90%, about 10% to about 80%, about 10% to about 70%, about 20% to about 60%, about 40% to about 60%, about 30% to about 45%, about 50% to about 99%, about 50% to about 90%, about 50% to about 80%, about 50% to about 70%, about 60% to about 90%, about 60% to about 80%, or about 60% to about 70% of the mean diameter of the input anucleate cells. In some embodiments, the width of the constriction about 0.25 μm to about 4 μm, about 1 μm to about 4 μm, about 1.2 μm to about 3 μm, about 1.4 μm to about 2.6 μm, about 1.6 μm to about 2.4 μm, or about 1.8 μm to about 2.2 μm. In some embodiments, the width of the constriction is about 2.0 μm. In some embodiments, the width of the constriction is about 2.5 μm. In some embodiments, the width of the constriction is about 3.0 μm. In some embodiments, the width of the constriction is about or less than any one of 0.25 μm, 0.5 μm, 1.0 μm, 1.2 μm, 1.4 μm, 1.6 μm, 1.8 μm, 2.0 μm, 2.2 μm, 2.4 μm, 2.6 μm, 2.8 μm, 3.0 μm, 3.2 μm, 3.4 μm, 3.6 μm, 3.8 μm, 4.0 μm, 4.2 μm, 4.4 μm, 4.6 μm, 4.8 μm, 5.0 μm, 5.2 μm, 5.4 μm, 5.6 μm, 5.8 μm, 6.0 μm. In some embodiments, the cell suspension comprising the input anucleate cells are passed through multiple constrictions wherein the multiple constrictions are arranged in series and/or in parallel.

In some embodiments, the mutated Ras antigen is a pool of multiple polypeptides that elicit a response against the same and or different mutated Ras antigens. In some embodiments, the mutated Ras antigen is a polypeptide comprising one or more antigenic mutated Ras epitope and one or more heterologous peptide sequences. In some embodiments, the mutated Ras antigen is delivered with other antigens or with an adjuvant. In some embodiments, the mutated Ras antigen comprises one or more of: a G12D mutation, a G12V mutation, a G12C mutation or a G13D mutation. In some embodiments, the mutated Ras antigen is a polypeptide comprising one or more antigenic mutated Ras epitopes that is flanked on the N-terminus and/or the C-terminus by one or more heterologous peptide sequences. In some embodiments, the mutated Ras antigen is one or more of a $G12D^{1-16}$, a $G12D^{2-19}$, a $G12D^{2-22}$, a $G12D^{2-29}$, a $G12V^{1-16}$, a $G12V^{2-19}$, a $G12V^{3-17}$, or a $G12V^{3-42}$. In some embodiments, the mutated Ras antigen comprises an amino acid sequence with at least 90% similarity to any one of SEQ ID NOs1-8. In some embodiments, the mutated Ras antigen comprises an amino acid sequence with at least any one of: 80%, 85%, 90%, or 95% similarity to any one of SEQ ID NOs1-8. In some embodiments, the mutated Ras antigen comprises an amino acid sequence of SEQ ID NOs:1-8. In some embodiments, the mutated Ras antigen comprises an amino acid sequence with at least 90% similarity to any one of SEQ ID NOs:9-15. In some embodiments, the mutated Ras antigen comprises an amino acid sequence with at least any one of: 90 similarity to any one of SEQ ID NOs:9-15. In some embodiments, the mutated Ras antigen comprises an amino acid sequence of SEQ ID NOs:9-15. In some embodiments, the mutated Ras antigen is capable of being processed into an MHC class I-restricted peptide. In some embodiments, the mutated Ras antigen is capable of being processed into an MHC class II-restricted peptide.

In some embodiments, the composition further comprises an adjuvant. In some embodiments, the adjuvant is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid (poly I:C), R837, R848, a TLR3 agonist, a TLR4 agonist or a TLR9 agonist. In some embodiments, the adjuvant is polyinosinic-polycytidylic acid (poly I:C).

Compositions of Anucleate Cell-Derived Vesicles Comprising Mutated Ras Antigen

In some aspects, provided are compositions of anucleate cell-derived vesicles comprising a mutated Ras antigen, wherein the mutated Ras antigen is delivered to the anucleate cell-derived vesicles intracellularly. In some embodiments, there is provided a composition of anucleate cell-derived vesicles comprising a mutated Ras-G12D antigen, wherein the mutated Ras-G12D antigen is delivered to the anucleate cell-derived vesicle intracellularly. In some embodiments, there is provided a composition of anucleate cell-derived vesicles comprising a mutated Ras-G12V antigen, wherein the mutated Ras-G12V antigen is delivered to the anucleate cell-derived vesicle intracellularly. In some embodiments, there is provided a composition of anucleate cell-derived vesicles comprising a mutated Ras-G12C antigen, wherein the mutated Ras-G12C antigen is delivered to the anucleate cell-derived vesicle intracellularly. In some embodiments, there is provided a composition of anucleate cell-derived vesicles comprising a mutated Ras-G13D antigen, wherein the mutated Ras-G13D antigen is delivered to the anucleate cell-derived vesicle intracellularly. In some embodiments, there is provided a composition of anucleate cell-derived vesicles comprising a mutated Ras antigen, wherein the mutated Ras antigen is delivered to the anucleate cell-derived vesicle intracellularly, wherein the Ras antigen comprises the amino acid sequence of any one of SEQ ID Nos:1-8.

In some aspects, there is provided a composition of anucleate cell-derived vesicles comprising a mutated Ras antigen, wherein the anucleate cell-derived vesicles comprising the mutated Ras antigen are prepared by: a) passing a cell suspension comprising input anucleate cells through a cell-deforming constriction, wherein a diameter of the constriction is a function of a diameter of the input anucleate cells in the suspension, thereby causing perturbations of the input anucleate cells large enough for the mutated Ras antigen to pass through to form perturbed input anucleate cells; and b) incubating the perturbed input anucleate cells with the mutated Ras antigen for a sufficient time to allow the mutated Ras antigen to enter the perturbed input anucleate cells; thereby generating anucleate cell-derived vesicles comprising the mutated Ras antigen. In some embodiments, the mutated Ras antigen is a mutated Ras antigen. In some embodiments, the mutated Ras antigen comprises the amino acid sequence of any one of SEQ ID Nos:9-15. In some embodiments, the mutated Ras antigen comprises an amino acid sequence with at least 90% identity to any one of SEQ ID Nos:9-15. In some embodiments, the mutated Ras antigen comprises the amino acid sequence of any one of SEQ ID Nos:1-8 In some embodiments, the mutated Ras antigen comprises an amino acid sequence with at least 90% identity to any one of SEQ ID Nos:1-8.

In some aspects, there is provided a composition of anucleate cell-derived vesicles comprising a mutated Ras antigen, or a mutated Ras antigen and an adjuvant, wherein the anucleate cell-derived vesicles comprising the mutated Ras antigen, or the mutated Ras antigen and the adjuvant are prepared by: a) passing a cell suspension comprising input anucleate cells through a cell-deforming constriction, wherein a diameter of the constriction is a function of a diameter of the input anucleate cells in the suspension, thereby causing perturbations of the input anucleate cells large enough for the mutated Ras antigen or the mutated Ras antigen and an adjuvant to pass through to form perturbed input anucleate cells; and b) incubating the perturbed input anucleate cells with the mutated Ras antigen or the mutated Ras antigen and an adjuvant for a sufficient time to allow the mutated Ras antigen to enter the perturbed input anucleate cells; thereby generating anucleate cell-derived vesicles comprising the mutated Ras antigen or the mutated Ras antigen and an adjuvant. In some embodiments, the mutated Ras antigen is a mutated Ras antigen. In some embodiments, the mutated Ras antigen comprises the amino acid sequence of any one of SEQ ID Nos:9-15. In some embodiments, the mutated Ras antigen comprises an amino acid sequence with at least 90% identity to any one of SEQ ID Nos:9-15. In some embodiments, the mutated Ras antigen comprises the amino acid sequence of any one of SEQ ID Nos:1-8 In some embodiments, the mutated Ras antigen comprises an amino acid sequence with at least 90% identity to any one of SEQ ID Nos:1-8.

In some aspects, there is provided a composition of anucleate cell-derived vesicles comprising a mutated Ras antigen, wherein the anucleate cell-derived vesicles comprising the mutated Ras antigen are prepared by: a) a) passing a cell suspension comprising input anucleate cells through a cell-deforming constriction, wherein a diameter of the constriction is a function of a diameter of the input anucleate cells in the suspension, thereby causing perturbations of the input anucleate cells large enough for a nucleic acid encoding the mutated Ras antigen and for an adjuvant to pass through to form perturbed input anucleate cells; and b) incubating the perturbed input anucleate cells with the nucleic acid encoding the mutated Ras antigen and with the adjuvant for a sufficient time to allow the nucleic acid encoding the mutated Ras antigen and for the adjuvant to enter the perturbed input anucleate cells; wherein the nucleic acid encoding the mutated Ras antigen is expressed thereby generating anucleate cell-derived vesicles comprising the mutated Ras antigen and an adjuvant. In some embodiments, the mutated Ras antigen is a mutated Ras antigen. In some embodiments, the mutated Ras antigen comprises the amino acid sequence of any one of SEQ ID Nos:9-15. In some embodiments, the mutated Ras antigen comprises an amino acid sequence with at least 90% identity to any one of SEQ ID Nos:9-15. In some embodiments, the mutated Ras antigen comprises the amino acid sequence of any one of SEQ ID Nos:1-8 In some embodiments, the mutated Ras antigen comprises an amino acid sequence with at least 90% identity to any one of SEQ ID Nos:1-8.

In some embodiments, the anucleate cell is an RBC or a platelet. In some embodiments, the anucleate cell is an erythrocyte or a reticulocyte. In some embodiments, the anucleate cell-derived vesicle is an RBC-derived vesicle or a platelet-derived vesicle. In some embodiments, the anucleate cell-derived vesicle is an erythrocyte-derived vesicle or a reticulocyte-derived vesicle.

In some embodiments, the width of the constriction is about 10% to about 99% of the mean diameter of the input anucleate cells. In some embodiments, the width of the constriction is any one of about 10% to about 90%, about 10% to about 80%, about 10% to about 70%, about 20% to about 60%, about 40% to about 60%, about 30% to about 45%, about 50% to about 99%, about 50% to about 90%, about 50% to about 80%, about 50% to about 70%, about 60% to about 90%, about 60% to about 80%, or about 60% to about 70% of the mean diameter of the input anucleate cells. In some embodiments, the width of the constriction about 0.25 μm to about 4 μm, about 1 μm to about 4 μm, about 1.2 μm to about 3 μm, about 1.4 μm to about 2.6 μm, about 1.6 μm to about 2.4 μm, or about 1.8 μm to about 2.2 μm. In some embodiments, the width of the constriction is about 2.0 μm. In some embodiments, the width of the constriction is about 2.5 μm. In some embodiments, the width of the constriction is about 3.0 μm. In some embodiments, the width of the constriction is about or less than any one of 0.25 μm, 0.5 μm, 1.0 μm, 1.2 μm, 1.4 μm, 1.6 μm, 1.8 μm, 2.0 μm, 2.2 μm, 2.4 μm, 2.6 μm, 2.8 μm, 3.0 μm, 3.2 μm, 3.4 μm, 3.6 μm, 3.8 μm, 4.0 μm, 4.2 μm, 4.4 μm, 4.6 μm, 4.8 μm, 5.0 μm, 5.2 μm, 5.4 μm, 5.6 μm, 5.8 μm, 6.0 μm. In some embodiments, the cell suspension comprising the input anucleate cells are passed through multiple constrictions wherein the multiple constrictions are arranged in series and/or in parallel.

In some embodiments, the mutated Ras antigen is a pool of multiple polypeptides that elicit a response against the same and or different mutated Ras antigens. In some embodiments, the mutated Ras antigen is a polypeptide comprising one or more antigenic mutated Ras epitope and one or more heterologous peptide sequences. In some embodiments, the mutated Ras antigen complexes with other antigens or with an adjuvant. In some embodiments, the mutated Ras antigen comprises one or more of: a G12D mutation, a G12V mutation, a G12C mutation or a G13D mutation. In some embodiments, the mutated Ras antigen is a polypeptide comprising one or more antigenic mutated Ras epitopes that is flanked on the N-terminus and/or the C-terminus by one or more heterologous peptide sequences. In some embodiments, the mutated Ras antigen is one or more of a $G12D^{1-16}$, a $G12D^{2-19}$, a $G12D^{2-22}$, a $G12D^{2-29}$, a $G12V^{1-16}$, a $G12V^{2-19}$, a $G12V^{3-17}$, or a $G12V^{3-42}$. In some embodiments, the mutated Ras antigen comprises an amino acid sequence with at least 90% similarity to any one of SEQ ID NOs:1-8. In some embodiments, the mutated Ras antigen comprises an amino acid sequence with at least any one of: 80%, 85%, 90%, or 95% similarity to any one of SEQ ID NOs:1-8. In some embodiments, the mutated Ras antigen comprises an amino acid sequence of SEQ ID NOs:1-8. In some embodiments, the mutated Ras antigen comprises an amino acid sequence with at least 90% similarity to any one of SEQ ID NOs:1-8. In some embodiments, the mutated Ras antigen comprises an amino acid sequence with at least 90% similarity to any one of SEQ ID NOs:9-15. In some embodiments, the mutated Ras antigen comprises an amino acid sequence of SEQ ID NOs:9-15. In some embodiments, the mutated Ras antigen is capable of being processed into an MHC class I-restricted peptide. In some embodiments, the mutated Ras antigen is capable of being processed into an MHC class II-restricted peptide.

In some embodiments, the composition further comprises an adjuvant. In some embodiments, the adjuvant is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid (poly I:C), R837, R848, a TLR3 agonist, a TLR4 agonist or a TLR9 agonist. In some embodiments, the adjuvant is polyinosinic-polycytidylic acid (poly I:C).

Further Modifications of Anucleate Cell-Derived Vesicles Comprising Mutated Ras Antigen In some embodiments according to any one of the methods described herein, the composition of anucleate-derived vesicles (e.g., RBC-derived vesicles) further comprises an agent that enhances the viability and/or function of the anucleate-derived vesicles as compared to a corresponding composition of anucleate-derived vesicles that does not comprise the agent. In some embodiments, the composition of anucleate-derived vesicles further comprises an agent that enhances the viability and/or function of the anucleate-derived vesicles upon freeze-thaw cycle as compared to a corresponding composition of anucleate-derived vesicles that does not comprise the agent. In some embodiments, the agent is a cryopreservation agent and/or a hypothermic preservation agent. In some embodiments, the cryopreservation agent nor the hypothermic preservation agent cause not more than 10% or 20% of cell death in a composition of anucleate-derived vesicles comprising the agent compared to a corresponding composition of anucleate-derived vesicles that does not comprise the agent before any freeze-thaw cycles. In some embodiments, at least about 70%, about 80%, or about 90% of the anucleate-derived vesicles are viable after up to 1, 2, 3, 4, 5 freeze-thaw cycles. In some embodiments, the agent is a compound that enhances endocytosis, a stabilizing agent or a co-factor. In some embodiments, the agent is albumin. In some embodiments, the albumin is mouse, bovine, or human albumin. In some embodiments, the agent is human albumin. In some embodiments, the agent is one or more of: a divalent metal cation, glucose, ATP, potassium, glycerol, trehalose, D-sucrose, PEG1500, L-arginine, L-glutamine, or EDTA. In some embodiments, the divalent metal cation is one more of $Mg^{2+}$, $Zn^{2+}$ or $Ca^{2+}$. In some embodiments, the agent is one or more of: sodium pyruvate, adenine, trehalose, dextrose, mannose, sucrose, human serum albumin (HSA), DMSO, HEPES, glycerol, glutathione, inosine, dibasic sodium phosphate, monobasic sodium phosphate, sodium metal ions, potassium metal ions, magnesium metal ions, chloride, acetate, gluoconate, sucrose, potassium hydroxide, or sodium hydroxide. In some embodiments, the agent is one or more of: Sodium pyruvate, adenine, Rejuvesol®, trehalose, dextrose, mannose, sucrose, human serum albumin (HSA), PlasmaLyte®, DMSO, Cryostor® CS2, Cryostor® CS5, Cryostor® CS10, Cryostor® CS15, HEPES, glycerol, glutathione, HypoThermosol®.

In some embodiments according to any one of the methods described herein, the process further comprises a step of incubating the composition of anucleate cells with an agent that enhances the viability and/or function of the anucleate cells compared to corresponding anucleate cells prepared without the further incubation step.

Adjuvants

As used herein, the term "adjuvant" can refer to a substance which either directly or indirectly modulates and/or engenders an immune response. In some embodiments of the invention, an adjuvant is delivered intracellularly to a population of anucleate cells or anucleate-derived vesicles such as a population of RBCs or RBC-derived vesicles (i.e, incubation of cells or vesicles with an adjuvant before, during and/or after constriction processing, but prior to administration to an individual) to form anucleate cell-derived vesicles comprising the adjuvant. In some instances, the adjuvant is administered in conjunction with a mutated Ras antigen to effect enhancement of an immune response to the mutated Ras antigen as compared to mutated Ras antigen alone. Therefore, adjuvants can be used to boost elicitation of an immune cell response (e.g. T cell response) to a mutated Ras antigen. Exemplary adjuvants include, without limitation, stimulator of interferon genes (STING) agonists, retinoic acid-inducible gene I (RIG-I) agonists, and agonists for TLR3, TLR4, TLR7, TLR8 and/or TLR9. Exemplary adjuvants include, without limitation, CpG ODN, interferon-α (IFN-α), polyinosinic:polycytidylic acid (polyI:C), imiquimod (R837), resiquimod (R848), or lipopolysaccharide (LPS). In some embodiments, the adjuvant is CpG ODN, LPS, IFN-α, IFN-β, IFN-γ, alpha-Galactosyl Ceramide, STING agonists, cyclic dinucleotides (CDN), RIG-I agonists, polyinosinic:polycytidylic acid (polyI:C), R837, R848, a TLR3 agonist, a TLR4 agonist or a TLR9 agonist. In particular embodiments, the adjuvant is a CpG ODN. In some embodiments, the adjuvant is a CpG ODN. In some embodiments, the CpG ODN is a Class A CpG ODN, a Class B CpG ODN, or a Class C CpG ODN. In some embodiments, the CpG ODN adjuvant comprise of a selection from the group of CpG ODN 1018, CpG ODN 1585, CpG ODN 2216, CpG ODN 2336, CpG ODN 1668, CpG ODN 1826, CPG ODN 2006, CpG ODN 2007, CpG ODN BW006, CpG ODN D-SL01, CpG ODN 2395, CpG ODN M362, CpG ODN D-SL03. In some embodiments, the CpG ODN adjuvant is CpG ODN 1826 (TCCATGACGTTCCTGACGTT (SEQ ID NO:16)) or CpG ODN 2006 (also known as CpG 7909) (TCGTCGTTTTGTCGTTTTGTCGTT (SEQ ID NO:17)) oligonucleotide. In some embodiments, the adjuvant is CpG 7909. In some embodiments, the RIG-I agonist comprises polyinosinic:polycytidylic acid (polyI:C). Multiple adjuvants can also be used in conjunction with mutated Ras antigens to enhance the elicitation of immune response. In some embodiments, the anucleate cell-derived vesicles comprising the mutated Ras antigen further comprise more than one adjuvant. Multiple adjuvants can also be used in conjunction with mutated Ras antigens to enhance the elicitation of immune response. In some embodiments, the anucleate cell-derived vesicles comprising the mutated Ras antigen further comprise more than one adjuvant. In some embodiments, the anucleate cell-derived vesicles comprising the mutated Ras antigen further comprise any combination of the adjuvants CpG ODN, LPS, IFN-α, IFN-β, IFN-γ, alpha-Galactosyl Ceramide, STING agonists, cyclic dinucleotides (CDN), RIG-I agonists, polyinosinic:polycytidylic acid (polyI:C), R837, R848, a TLR3 agonist, a TLR4 agonist or a TLR9 agonist.

Constrictions Used in Generating Compositions of Anucleate Cell-Derived Vesicles Comprising Mutated Ras Antigen In some embodiments, the invention provides compositions of anucleate cell-derived vesicles comprising a mutated Ras antigen for stimulating an immune response. In some embodiments, the anucleate cell is an RBC or a platelet. In some embodiments, the anucleate cell is an erythrocyte or a reticulocyte. In some embodiments, the mutated Ras antigen is delivered to the anucleate cells intracellularly. Methods of introducing payloads to anucleate cells are known in the art.

In some embodiments, the mutated Ras antigen is introduced into the anucleate cells by passing the cell through a constriction such that transient pores are introduced to the membrane of the cell thereby allowing the mutated Ras antigen to enter the cell. Examples of constriction-based delivery of compounds into a cell are provided by WO 2013/059343, WO 2015/023982, WO 2016/070136, WO2017041050, WO2017008063, WO 2017/192785, WO 2017/192786, WO 2019/178005, WO 2019/178006, WO 2020/072833, PCT/US2020/15098, and PCT/US2020/020194.

In some embodiments, the mutated Ras antigen is delivered into the anucleate cells to produce the anucleate cell-derived vesicles of the invention by passing a cell suspension comprising the anucleate cells (e.g., RBCs) through a constriction, wherein the constriction deforms the cells thereby causing a perturbation of the cells such that a mutated Ras antigen enters the cells. In some embodiments, the constriction is contained within a microfluidic channel. In some embodiments, multiple constrictions can be placed in parallel and/or in series within the microfluidic channel.

In some embodiments, the constriction within the microfluidic channel includes an entrance portion, a center point, and an exit portion. In some embodiments, the length, depth, and width of the constriction within the microfluidic channel can vary. In some embodiments, the width of the constriction within the microfluidic channel is a function of the diameter of the anucleate cells. Methods to determine the diameter of anucleate cells are known in the art; for example, high-content imaging, cell counters or flow cytometry.

In some embodiments of the constriction-based delivery of a mutated Ras antigen to anucleate cell-derived vesicles, the width of the constriction is about 0.5 μm to about 10 μm. In some embodiments, the width of the constriction is about 1 μm to about 4 μm. In some embodiments, the width of the constriction is about 1 μm to about 3 μm. In some embodiments, the width of the constriction is about 1.5 μm to about 2.5 μm. In some embodiments, the width of the constriction is about 1.2 μm to about 2.8 μm. In some embodiments, the width of the constriction is about 0.5 μm to about 5 μm. In some embodiments, the width of the constriction is about 2 μm to about 2.5 μm. In some embodiments, the width of the constriction is about 1.5 μm to about 2 μm. In some embodiments, the width of the constriction is about 0.5 μm to about 3.5 μm. In some embodiments, the width of the constriction is about 3.2 μm to about 3.8 μm. In some embodiments, the width of the constriction is about 3.8 μm to about 4.3 μm. In some embodiments, the width of the constriction is about or less than any one of 0.25 μm, 0.5 μm, 1.0 μm, 1.2 μm, 1.4 μm, 1.6 μm, 1.8 μm, 2.0 μm, 2.2 μm, 2.4 μm, 2.6 μm, 2.8 μm, 3.0 μm, 3.2 μm, 3.4 μm, 3.6 μm, 3.8 μm, 4.0 μm, 4.2 μm, 4.4 μm, 4.6 μm, 4.8 μm, 5.0 μm, 5.2 μm, 5.4 μm, 5.6 μm, 5.8 μm, 6.0 μm. In some embodiments, the width of the constriction is about 2 μm. In some embodiments, the width of the constriction is about 2.5 μm. In some embodiments, the width of the constriction is about 3 μm.

Examples of parameters that may influence the delivery of the compound into the anucleate-derived vesicles include, but are not limited to, the dimensions of the constriction, the entrance angle of the constriction, the surface properties of the constrictions (e.g., roughness, chemical modification, hydrophilic, hydrophobic, etc.), the operating flow speeds (e.g., cell transit time through the constriction), the cell concentration, the concentration of the compound in the cell suspension, buffer in the cell suspension, and the amount of time that the anucleate-derived vesicles recover or incubate after passing through the constrictions can affect the passage of the delivered compound into the anucleate-derived vesicles. Additional parameters influencing the delivery of the compound into the anucleate-derived vesicles can include the velocity of the input anucleate cells in the constriction, the shear rate in the constriction, the viscosity of the cell suspension, the velocity component that is perpendicular to flow velocity, and time in the constriction. In addition, multiple chips comprising channels in series and/or in parallel may impact delivery to anucleate-derived vesicles. Multiple chips in parallel may be useful to enhance throughput. Such parameters can be designed to control delivery of the compound. In some embodiments, the cell concentration ranges from about 10 to at least about $10^{12}$ cells/mL or any concentration or range of concentrations therebetween. In some embodiments, delivery compound concentrations can range from about 10 ng/mL to about 1 g/mL or any concentration or range of concentrations therebetween. In some embodiments, delivery compound concentrations can range from about 1 pM to at least about 2 M or any concentration or range of concentrations therebetween.

In some embodiments, the concentration of mutated Ras antigen incubated with the anucleate cells or anucleate-cell derived vesicles is between about 0.01 μM and about 10 mM. For example, in some embodiments, the concentration of mutated Ras antigen incubated with the anucleate cells or anucleate cell-derived vesicles is any of less than about 0.01 μM, about 0.1 μM, about 1 μM, about 10 μM, about 100 μM, about 1 mM or about 10 mM. In some embodiments, the concentration of mutated Ras antigen incubated with the anucleate cells or anucleate cell-derived vesicles is greater than about 10 mM. In some embodiments, the concentration of mutated Ras antigen incubated with the anucleate cells or anucleate cell-derived vesicles is any of between about 0.01 μM and about 0.1 μM, between about 0.1 μM and about 1 μM, between about 1 μM and about 10 μM, between about 10 μM and about 100 μM, between about 100 μM and about 1 mM, or between 1 mM and about 10 mM. In some embodiments, the concentration of mutated Ras antigen incubated with the anucleate cells or anucleate cell-derived vesicles is between about 0.1 μM and about 1 mM. In some embodiments, the concentration of mutated Ras antigen incubated with the anucleate cells or anucleate cell-derived vesicles is between about 0.1 μM and about 10 μM. In some embodiments, the concentration of mutated Ras antigen incubated with the anucleate cells or anucleate cell-derived vesicles is 1 μM.

In some embodiments, the anucleate cells or anucleate cell-derived vesicles comprise the nucleic acid encoding the mutated Ras antigen at a concentration between about 1 nM and about 1 mM. In some embodiments, the anucleate cells or anucleate cell-derived vesicles comprises the nucleic acid encoding the mutated Ras antigen at a concentration of any of less than about 0.1 nM, about 1 nM, about 0.01 μM, about 0.1 μM, about 1 μM, about 10 μM, about 100 PM, about 1 mM or about 10 mM. In some embodiments, the anucleate cells or anucleate cell-derived vesicles comprise the nucleic acid encoding the mutated Ras antigen at a concentration of greater than about 10 mM. In some embodiments, the anucleate cells or anucleate cell-derived vesicles comprise the nucleic acid encoding the mutated Ras antigen at a concentration of any of between about 0.1 nM to about 1 nM, about 1 nM to about 10 nM, about 10 nM to about 100 nM, about 0.1 μM and about 1 μM, between about 1 μM and about 10 μM, between about 10 μM and about 100 μM, between about 100 μM and about 1 mM, or between 1 mM and about 10 mM. In some embodiments, the anucleate cells or anucleate cell-derived vesicles comprise the nucleic acid encoding the mutated Ras antigen at a concentration between about 10 nM and about 100 nM. In some embodiments, the anucleate cells or anucleate cell-derived vesicles comprise the nucleic acid encoding the mutated Ras antigen at a concentration between about 1 nM and about 10 nM. In some embodiments, the anucleate cells or anucleate cell-derived vesicles comprise the mutated Ras antigen at a concentration of about 50 nM. In some embodiments, the nucleic acid is an mRNA.

Characteristics of Anucleate Cell-Derived Vesicles and Internalization by Antigen Presenting Cells In embodiments according to any one of the methods, uses or compositions described herein, the method comprises: a) passing a cell suspension comprising input anucleate cells through a cell-deforming constriction, wherein a diameter of the constriction is a function of a diameter of the input anucleate cells in the suspension, thereby causing perturbations of the input anucleate cells large enough for the mutated Ras antigen or the mutated Ras antigen and an adjuvant to pass through to form perturbed input anucleate cells; b) incubating the perturbed input anucleate cells with the mutated Ras antigen or the mutated Ras antigen and an adjuvant for a sufficient time to allow the mutated Ras antigen or the mutated Ras antigen and an adjuvant to enter the perturbed input anucleate cells; thereby generating anucleate cell-derived vesicles comprising the mutated Ras antigen or the mutated Ras antigen and an adjuvant. In some embodiments, the anucleate cell-derived vesicle comprising the payload (such as the mutated Ras antigen or the mutated Ras antigen and an adjuvant) displays different characteristics compared to an input anucleate cell. In some embodiments, the anucleate cell-derived vesicle comprising the payload (such as the mutated Ras antigen or the mutated Ras antigen and an adjuvant) displays different characteristics compared to an anucleate cell comprising a payload introduced by other delivery methods (such as hemolytic loading or electroporation). In some embodiments, the anucleate cell-derived vesicle comprising the payload (such as the mutated Ras antigen or the mutated Ras antigen and an adjuvant) is an anucleate cell-derived vesicle comprising the payload. In some embodiments, the anucleate cell-derived vesicle comprising an antigen (such as mutated Ras antigen) is referred to as an antigen carrier (AC). In some embodiments, the anucleate cell-derived vesicle comprising an antigen (such as mutated Ras antigen) and an adjuvant is referred to as an activating antigen carrier (AAC). Anucleate cell-derived vesicles are disclosed in PCT/US2020/15098, the contents of which are hereby incorporated in entirety by reference.

In some embodiments, the half-life of the anucleate cell-derived vesicle following administration to a mammal is decreased compared to a half-life of the input anucleate cell following administration to the mammal. In some embodiments, the hemoglobin content of the anucleate cell-derived vesicle is decreased compared to the hemoglobin content of the input anucleate cell. In some embodiments, ATP production of the anucleate cell-derived vesicle is decreased compared to ATP production of the input anucleate cell. In some embodiments, the anucleate cell-derived vesicle exhibits a spherical morphology. In some embodiments, the input anucleate cell is an erythrocyte and wherein the anucleate cell-derived vesicle has a reduced biconcave shape compared to the input anucleate cell. In some embodiments, the anucleate cell-derived vesicle is a red blood cell ghost. In some embodiments, the anucleate cell-derived vesicles prepared by the process have greater than about 1.5 fold more phosphatidylserine on its surface compared to the input anucleate cell. In some embodiments, a population profile of anucleate cell-derived vesicles prepared by the process exhibits higher average phosphatidylserine levels on the surface compared to the input anucleate cells. In some embodiments, at least 50% of the population profile of anucleate cell-derived vesicles prepared by the process exhibits higher phosphatidylserine levels on the surface compared to the input anucleate cells. In some embodiments, the anucleate cell-derived vesicle exhibits preferential uptake in a tissue or cell compared to the input anucleate cell. In some embodiments, the anucleate cell-derived vesicle exhibits preferential uptake in phagocytic cells and/or antigen presenting cells compared to the input anucleate cell. In some embodiments, the anucleate cell-derived vesicle is modified to enhance uptake in a tissue or cell compared to the input anucleate cell. In some embodiments, the anucleate cell-derived vesicle is modified to enhance uptake in phagocytic cells and/or antigen presenting cells compared to an unmodified anucleate cell-derived vesicle. In some embodiments, the phagocytic cells and/or antigen presenting cells comprise one or more of a dendritic cell or macrophage. In some embodiments, the tissue or cell comprises one or more of liver or spleen. In some embodiments, the anucleate cell-derived vesicle comprises CD47 on its surface.

In some embodiments of the above method for generating an anucleate cell-derived vesicle, the constriction is contained within a microfluidic channel. In some embodiments, the microfluidic channel comprises a plurality of constrictions. In some embodiments, the plurality of constrictions is arranged in series and/or in parallel. In some embodiments, the constriction is between a plurality of micropillars; between a plurality of micropillars configured in an array; or between one or more movable plates. In some embodiments, the constriction is a pore or contained within a pore. In some embodiments, the pore is contained in a surface. In some embodiments, the surface is a filter. In some embodiments, the surface is a membrane. In some embodiments, the constriction size is a function of the diameter of the input anucleate cell in suspension. In some embodiments, the constriction size is about 10%, about 20%, about 30%, about 40%, about 50%, about 60%, or about 70% of the diameter of the input anucleate cell in suspension. In some embodiments, the constriction has a width of about 0.25 μm to about 4 μm. In some embodiments, the constriction has a width of about 4 μm, 3.5 μm, about 3 μm, about 2.5 μm, about 2 μm, about 1.5 μm, about 1 μm, about 0.5 μm, or about 0.25 μm. In some embodiments, the constriction has a width of about 2.2 μm. In some embodiments, the input anucleate cells are passed through the constriction under a pressure ranging from about 10 psi to about 90 psi. In some embodiments, said cell suspension is contacted with the antigen before, concurrently, or after passing through the constriction.

In some embodiments, wherein a anucleate cell-derived vesicle comprising the payload (e.g. mutated Ras antigen, or mutated Ras antigen and an adjuvant) is prepared from an input anucleate cell, the anucleate cell-derived vesicle having one or more of the following properties: (a) a circulating half-life in a mammal is decreased compared to the input anucleate cell, (b) decreased hemoglobin levels compared to the input anucleate cell, (c) spherical morphology, (d) increased surface phosphatidylserine levels compared to the input anucleate cell, or (e) reduced ATP production compared to the input anucleate cell.

In some embodiments, the input anucleate cell is a mammalian cell. In some embodiments, the input anucleate cell is human cell. In some embodiments, the input anucleate cell is a red blood cell or a platelet. In some embodiments, the red blood cell is an erythrocyte or a reticulocyte.

In some embodiments, the circulating half-life of the anucleate cell-derived vesicle in a mammal is decreased compared to the input anucleate cell. In some embodiments, the circulating half-life in the mammal is decreased by more than about 50%, about 60%, about 70%, about 80%, about 90%, about 95%, about 96%, about 97%, about 98%, or about 99% compared to the input anucleate cell.

In some embodiments, the input anucleate cell is a human cell and wherein the circulating half-life of the anucleate cell-derived vesicle is less than about 1 minute, about 2 minutes, about 5 minutes, about 10 minutes, about 15 minutes, about 30 minutes, about 1 hour, about 6 hours, about 12 hours, about 1 day, about 2 days, about 3 days, about 4 days, about 5 days, about 10 days, about 25 days, about 50 days, about 75 days, about 100 days, about 120 days.

In some embodiments, the input anucleate cell is a red blood cell, wherein the hemoglobin levels in the anucleate cell-derived vesicle are decreased compared to the input anucleate cell. In some embodiments, the hemoglobin levels in the anucleate cell-derived vesicle are decreased by at least about 10%, about 20%, about 30%, about 40%, about 50%, about 60%, about 70%, about 80%, about 90%, about 99% or about 100% compared to the input anucleate cell. In some embodiments, the hemoglobin levels in the anucleate cell-derived vesicle are about 1%, about 5%, about 10%, about 20%, about 30%, about 40%, or about 50% the level of hemoglobin in the input anucleate cell.

In some embodiments, the input anucleate cell is an erythrocyte and wherein the anucleate cell-derived vesicle is spherical in morphology. In some embodiments, the input anucleate cell is an erythrocyte and wherein the anucleate cell-derived vesicle has a reduced biconcave shape compared to the input anucleate cell.

In some embodiments, the input anucleate cell is a red blood cell or an erythrocyte and wherein the anucleate cell-derived vesicle is a red blood cell ghost (RBC ghost).

In some embodiments, the anucleate cell-derived vesicle comprises CD47 on its surface.

In some embodiments, the anucleate cell-derived vesicle has increased surface phosphatidylserine levels compared to the input anucleate cell. In some embodiments, the anucleate cell-derived vesicles prepared by the process has greater than about 1.5 fold more phosphatidylserine on its surface compared to the input anucleate cell. In some embodiments, the anucleate cell-derived vesicle has about 10%, about 20%, about 30%, about 40%, about 50%, about 60%, about 70%, about 80%, about 90%, about 99%, about 100% or more than about 100% more phosphatidylserine on its surface compared to the input anucleate cell.

In some embodiments, the anucleate cell-derived vesicle has reduced ATP production compared to the input anucleate cell. In some embodiments, the anucleate cell-derived vesicle produces ATP at less than about 1%, about 5%, about 10%, about 20%, about 30%, about 40%, or about 50% the level of ATP produced by the input anucleate cell. In some embodiments, the anucleate cell-derived vesicle does not produce ATP.

In some embodiments, the anucleate cell-derived vesicle exhibits enhanced uptake in a tissue or cell compared to the input anucleate cell. In some embodiments, the anucleate cell-derived vesicle exhibits preferential uptake in liver or spleen or by a phagocytic cell or an antigen-presenting cell compared to the uptake of the input anucleate cell.

In some embodiments, the anucleate cell-derived vesicle is further modified to enhance uptake in a tissue or cell compared to the input anucleate cell. In some embodiments, the anucleate cell-derived vesicle is further modified to enhance uptake in liver or spleen or by a phagocytic cell or an antigen-presenting cell compared to the uptake of the input anucleate cell.

In some embodiments, wherein the anucleate cell-derived vesicle exhibits enhanced uptake in liver or spleen or by a phagocytic cell and/or an antigen-presenting cell, internalization of the anucleate cell-derived vesicle results in increased expression of maturation markers of the phagocytic cell or the antigen-presenting cell. In some embodiments, the phagocytic cell and/or the antigen-presenting cell is a monocyte-derived dendritic cell (MODC). In some embodiments, the maturation marker is one or more of CD80, CD86, CD83, and MHC-II. In some embodiments, the expression of one or more of CD80, CD86, CD83, and MHC-II is increased in the phagocytic cell and/or the antigen-presenting cell contacted with a anucleate cell-derived vesicle comprising a mutated Ras antigen by at least about any one of: 10%, 20%, 50%, 80%, 100%, 2-fold, 5-fold, 10-fold, 20-fold, 50-fold, 100-fold, 1000-fold, 10000-fold or more compared to a phagocytic cell and/or a antigen-presenting cell not contacted with a anucleate cell-derived vesicle comprising a mutated Ras antigen. In some embodiments, the expression of one or more of CD80, CD86, CD83, and MHC-II is increased in the phagocytic cell and/or the antigen-presenting cell contacted with a anucleate cell-derived vesicle comprising a mutated Ras antigen by at least about any one of: 10%, 20%, 50%, 80%, 100%, 2-fold, 5-fold, 10-fold, 20-fold, 50-fold, 100-fold, 1000-fold, 10000-fold or more compared to a phagocytic cell and/or a antigen-presenting cell contacted with the input anucleate cell.

In some embodiments, wherein the anucleate cell-derived vesicle comprising an mutated Ras antigen, or a mutated Ras antigen and adjuvant exhibits enhanced uptake in liver or spleen or by a phagocytic cell and/or an antigen-presenting cell, internalization of the anucleate cell-derived vesicle results in increased presentation of the mutated Ras antigen comprised within the anucleate cell-derived vesicle. In some embodiments, the presentation of the mutated Ras antigen is increased in the phagocytic cell and/or the antigen-presenting cell contacted with a anucleate cell-derived vesicle comprising a mutated Ras antigen by at least about any one of: 10%, 20%, 50%, 80%, 100%, 2-fold, 5-fold, 10-fold, 20-fold, 50-fold, 100-fold, 1000-fold, 10000-fold or more compared to a phagocytic cell and/or a antigen-presenting cell contacted with corresponding anucleate cells comprising the same mutated Ras antigen introduced by other delivery methods (such as but not limited to hemolytic loading).

In some embodiments, wherein the anucleate cell-derived vesicle comprising an mutated Ras antigen, or a mutated Ras antigen and adjuvant exhibits enhanced uptake in liver or spleen or by a phagocytic cell and/or an antigen-presenting cell, internalization of the anucleate cell-derived vesicle results in increased ability of the phagocytic cell and/or the antigen-presenting cell to induce an antigen-specific immune response. In some embodiments, the antigen-specific immune response mediated by the phagocytic cell and/or the antigen-presenting cell contacted with a anucleate cell-derived vesicle comprising the mutated Ras antigen or the mutated Ras antigen and adjuvant is increased by at least about any one of: 10%, 20%, 50%, 80%, 100%, 2-fold, 5-fold, 10-fold, 20-fold, 50-fold, 100-fold, 1000-fold, 10000-fold or more compared to a phagocytic cell and/or a antigen-presenting cell contacted with the input anucleate cells. In some embodiments, the antigen-specific immune response mediated by the phagocytic cell and/or the antigen-presenting cell contacted with a anucleate cell-derived vesicle comprising the mutated Ras antigen or the mutated Ras antigen and adjuvant is increased by at least about any one of: 10%, 20%, 50%, 80%, 100%, 2-fold, 5-fold, 10-fold, 20-fold, 50-fold, 100-fold, 1000-fold, 10000-fold or more compared to a phagocytic cell and/or a antigen-presenting cell contacted with the anucleate cells comprising the same mutated Ras antigen introduced by other delivery methods (such as but not limited to hemolytic loading). In some embodiments, the antigen-specific immune response is an antigen-specific CD4+ T cell response. In some embodiments, the antigen-specific immune response is an antigen-specific CD8+ T cell response.

In some embodiments according to any one of the methods, compositions, or uses described herein, the phagocytes are human cells with a haplotype of of HLA-A*02, HLA-A*01, HLA-A*03, HLA-A*24, HLA-A*11, HLA-A*26, HLA-A*32, HLA-A*31, HLA-A*68, HLA-A*29, HLA-A*23, HLA-B*07, HLA-B*44, HLA-B*08, HLA-B*35, HLA-B*15, HLA-B*40, HLA-B*27, HLA-B*18, HLA-B*51, HLA-B*14, HLA-B*13, HLA-B*57, HLA-B*38, HLA-C*07, HLA-C*04, HLA-C*03, HLA-C*06, HLA-C*05, HLA-C*12, HLA-C*02, HLA-C*01, HLA-C*08, or HLA-C*16. In some embodiments, the antigen presenting cells are human cells with a haplotype of HLA-A*02, HLA-A*11, HLA-B*07, or HLA-C*08. In some embodiments, mutated Ras antigens presented by the phagocytes and/or antigen presenting cells described herein are comprised of an HLA-A2-specific epitope. In some embodiments, mutated Ras antigens presented by the phagocytes and/or antigen presenting cells described herein are comprised of an HLA-A11-specific epitope. In some embodiments, mutated Ras antigens presented by the phagocytes and/or antigen presenting cells described herein are comprised of an HLA-B7-specific epitope. In some embodiments, mutated Ras antigens presented by the phagocytes and/or antigen presenting cells described herein are comprised of an HLA-C8-specific epitope.

In some embodiments, the input anucleate cell was not (a) heat processed, (b) chemically treated, and/or (c) subjected to hypotonic or hypertonic conditions during the preparation of the anucleate cell-derived vesicles. In some embodiments, osmolarity was maintained during preparation of the anucleate cell-derived vesicle from the input anucleate cell. In some embodiments, the osmolarity was maintained between about 200 mOsm and about 600 mOsm. In some embodiments, the osmolarity was maintained between about 200 mOsm and about 400 mOsm.

Systems and Kits

In some aspects, the invention provides a system comprising one or more of the constriction, an anucleate cell suspension, mutated Ras antigens or adjuvants for use in the methods disclosed herein. The system can include any embodiment described for the methods disclosed above, including microfluidic channels or a surface having pores to provide cell-deforming constrictions, cell suspensions, cell perturbations, delivery parameters, compounds, and/or applications etc. In some embodiment, the cell-deforming constrictions are sized for delivery to anucleate cells. In some embodiments, the delivery parameters, such as operating flow speeds, cell and compound concentration, velocity of the cell in the constriction, and the composition of the cell suspension (e.g., osmolarity, salt concentration, serum content, cell concentration, pH, etc.) are optimized for maximum response of a compound for suppressing an immune response or inducing tolerance.

Also provided are kits or articles of manufacture for use in treating individuals with a cancer associated with a Ras mutation. In some embodiments, the kit comprises an anucleate cell-derived vesicle comprising intracellularly a mutated antigen and intracellularly an adjuvant. In some embodiments, the kit comprises one or more of the constriction, an anucleate cell suspension, mutated Ras antigens or adjuvants for use in generating anucleate cell-derived vesicles for use in treating an individual with a cancer associated with a Ras mutation, such as cancer. In some embodiments, the kits comprise the compositions described herein (e.g. a microfluidic channel or surface containing pores, cell suspensions, and/or compounds) in suitable packaging. Suitable packaging materials are known in the art, and include, for example, vials (such as sealed vials), vessels, ampules, bottles, jars, flexible packaging (e.g., sealed Mylar or plastic bags), and the like. These articles of manufacture may further be sterilized and/or sealed.

The invention also provides kits comprising components of the methods described herein and may further comprise instructions for performing said methods treat an individual with a cancer associated with a Ras mutation and/or instructions for introducing a mutated Ras antigen and an adjuvant into an anucleate cell. The kits described herein may further include other materials, including other buffers, diluents, filters, needles, syringes, and package inserts with instructions for performing any methods described herein; e.g., instructions for treating an individual with a cancer associated with a Ras mutation or instructions for generating anucleate cell-derived vesicles to contain intracellularly a mutated Ras antigen and intracellularly an adjuvant.

EXEMPLARY EMBODIMENTS

Embodiment 1. A method for stimulating an immune response to a mutated Ras protein in an individual, the method comprising administering an effective amount of a composition comprising anucleate cell-derived vesicles to an individual, wherein anucleate cell-derived vesicles comprise a mutated Ras antigen; wherein the mutated Ras antigen is delivered to the anucleate cell-derived vesicles intracellularly.

Embodiment 2. A method for reducing tumor growth in an individual, the method comprising administering an effective amount of a composition comprising anucleate cell-derived vesicles to an individual, wherein the anucleate cells comprise a mutated Ras antigen; wherein the mutated Ras antigen is delivered to the anucleate cell-derived vesicles intracellularly.

Embodiment 3. A method for vaccinating an individual in need thereof, the method comprising administering an effective amount of a composition comprising anucleate cell-derived vesicles to an individual, wherein the anucleate cell-derived vesicles comprise a mutated Ras antigen; wherein the mutated Ras antigen is delivered to the anucleate cell-derived vesicles intracellularly.

Embodiment 4. The method of any one of embodiments 1-3, wherein the individual has cancer.

Embodiment 5. A method for treating cancer in an individual, the method comprising administering an effective amount of a composition comprising anucleate cell-derived vesicles to an individual, wherein the anucleate cell-derived vesicles comprise a mutated Ras antigen; wherein the mutated Ras antigen is delivered to the anucleate cell-derived vesicles intracellularly.

Embodiment 6. The method of embodiment 4 or 5, wherein the cancer is a pancreatic cancer, a colon cancer, a small intestine cancer, a biliary tract cancer, an endometrial cancer, a lung cancer, a skin cancer, an ovarian cancer, a stomach cancer, an esophageal cancer, a cervical cancer or a urinary tract cancer.

Embodiment 7. The method of any one of embodiments 1-6, wherein the mutated Ras antigen is a mutated K-Ras antigen, a mutated H-Ras antigen, or a mutated N-Ras antigen.

Embodiment 8. The method of any one of embodiments 1-7, wherein the mutated Ras antigen is a mutated K-Ras4A antigen or a mutated K-Ras4B antigen.

Embodiment 9. The method of any one of embodiments 1-8, wherein the mutated Ras antigen is a single polypeptide that elicits a response against the same and or different mutated Ras antigens.

Embodiment 10. The method of any one embodiments 1-8, wherein the mutated Ras antigen is a pool of multiple polypeptides that elicit a response against the same and or different mutated Ras antigens.

Embodiment 11. The method of any one of embodiments 1-8, wherein the mutated Ras antigen is a polypeptide comprising one or more antigenic mutated Ras epitopes and one or more heterologous peptide sequences.

Embodiment 12. The method of any one of embodiments 1-11, wherein the mutated Ras antigen complexes with other antigens or with an adjuvant.

Embodiment 13. The method of any one of embodiments 1-12, wherein the mutated Ras antigen comprises a G12D mutation, a G12V mutation, a G12C mutation or a G13D mutation.

Embodiment 14. The method of any one of embodiments 1-13, wherein the mutated Ras antigen comprises an amino acid sequence with at least 90% similarity to any one of SEQ ID NOs:9-15.

Embodiment 15. The method of any one of embodiments 1-14, wherein the mutated Ras antigen comprises an amino acid sequence of SEQ ID NOs:9-15.

Embodiment 16. The method of any one of embodiments 1-15, wherein the mutated Ras antigen is one or more of a $G12D^{1-16}$, a $G12D^{2-19}$, a $G12D^{2-22}$, a $G12D^{2-29}$, a $G12V^{1-16}$, a $G12V^{2-19}$, a $G12V^{3-17}$, or a $G12V^{3-42}$ antigen.

Embodiment 17. The method of any one of embodiments 1-16, wherein the mutated Ras antigen comprises an amino acid sequence with at least 90% similarity to any one of SEQ ID NOs:1-8.

Embodiment 18. The method of any one of embodiments 1-17, wherein the mutated Ras antigen comprises an amino acid sequence of SEQ ID NOs:1-8.

Embodiment 19. The method of any one of embodiments 1-18, wherein the mutated Ras antigen is a polypeptide comprising one or more antigenic mutated Ras epitopes that is flanked on the N-terminus and/or the C-terminus by one or more heterologous peptide sequences.

Embodiment 20. The method of any one of embodiments 1-19, wherein the mutated Ras antigen is capable of being processed into an MHC class I-restricted peptide.

Embodiment 21. The method of any one of embodiments 1-20, wherein the mutated Ras antigen is capable of being processed into an MHC class II-restricted peptide.

Embodiment 22. The method of any one of embodiments 1-21, wherein the anucleate cell further comprises an adjuvant.

Embodiment 23. The method of any one of embodiments 1-22, wherein the composition is administered in conjunction with an adjuvant.

Embodiment 24. The method of embodiment 22 or 23, wherein the adjuvant is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid, R837, R848, a TLR3 agonist, a TLR4 agonist or a TLR9 agonist.

Embodiment 25. The method of any one of embodiments 22-24, wherein the adjuvant is polyinosinic-polycytidylic acid.

Embodiment 26. The method of any one of embodiments 1-25, wherein the anucleate cell-derived vesicles comprising the mutated Ras antigen or the mutated Ras antigen and an adjuvant are prepared by a) passing a cell suspension comprising input anucleate cells through a cell-deforming constriction, wherein a diameter of the constriction is a function of a diameter of the input anucleate cells in the suspension, thereby causing perturbations of the input anucleate cells large enough for the mutated Ras antigen or the mutated Ras antigen and an adjuvant to pass through to form a perturbed input anucleate cells; and b) incubating the perturbed input anucleate cells with the mutated Ras antigen or the mutated Ras antigen and an adjuvant for a sufficient time to allow the mutated Ras antigen or the mutated Ras antigen and an adjuvant to enter the perturbed input anucleate cells; thereby generating anucleate cell-derived vesicles comprising the mutated Ras antigen or the mutated Ras antigen and an adjuvant.

Embodiment 27. The method of any one of embodiments 1-25, wherein the anucleate cell-derived vesicles comprising the mutated Ras antigen are prepared by a) passing a cell suspension comprising input anucleate cells through a cell-deforming constriction, wherein a diameter of the constriction is a function of a diameter of the input anucleate cells in the suspension, thereby causing perturbations of the input anucleate cells large enough for a nucleic acid encoding the mutated Ras antigen to pass through to form a perturbed input anucleate cells; and b) incubating the perturbed input anucleate cells with the nucleic acid encoding the mutated Ras antigen for a sufficient time to allow the nucleic acid encoding the mutated Ras antigen to enter the perturbed input anucleate cells; wherein the nucleic acid encoding the mutated Ras antigen is expressed thereby generating anucleate cell-derived vesicles comprising the mutated Ras antigen.

Embodiment 28. The method of any one of embodiments 1-24, wherein the anucleate cell-derived vesicles comprising the mutated Ras antigen and an adjuvant are prepared by a) passing a cell suspension comprising input anucleate cells through a cell-deforming constriction, wherein a diameter of the constriction is a function of a diameter of the input anucleate cells in the suspension, thereby causing perturbations of the input anucleate cells large enough for a nucleic acid encoding the mutated Ras antigen and for an adjuvant to pass through to form a perturbed input anucleate cells; and b) incubating the perturbed input anucleate cells with the nucleic acid encoding the mutated Ras antigen and with the adjuvant for a sufficient time to allow the nucleic acid encoding the mutated Ras antigen and for the adjuvant to enter the perturbed input anucleate cells; wherein the nucleic acid encoding the mutated Ras antigen is expressed thereby generating anucleate cell-derived vesicles comprising the mutated Ras antigen and an adjuvant.

Embodiment 29. The method of any one of embodiments 26-28, wherein the width of the constriction is about 10% to about 99% of the mean diameter of the input anucleate cells.

Embodiment 30. The method of any one of embodiments 26-29, wherein the width of the constriction is about 1.6 μm to about 2.4 μm or about 1.8 μm to about 2.2 μm.

Embodiment 31. The method of any one of embodiments 26-30, wherein the cell suspension comprising the plurality of input anucleate cells are passed through multiple constrictions wherein the multiple constrictions are arranged in series and/or in parallel.

Embodiment 32. The method of any one of embodiments 1-31, wherein the anucleate cell is a red blood cell or a platelet.

Embodiment 33. The method of any one of embodiments 1-32, wherein the anucleate cell is an erythrocyte or a reticulocyte.

Embodiment 34. The method of any one of embodiments 1-33, wherein the composition comprising the anucleate cell-derived vesicles is administered a plurality of times.

Embodiment 35. The method of any one of embodiments 1-34, wherein the composition is administered intravenously.

Embodiment 36. The method of any one of embodiments 1-35, wherein the individual is a human.

Embodiment 37. The method of any one of embodiments 1-36, wherein the composition is administered prior to, concurrently with, or following administration of another therapy.

Embodiment 38. The method of embodiment 37, wherein the another therapy is a chemotherapy, a radiation therapy, an antibody, a cytokine, an immune checkpoint inhibitor, or a bispecific polypeptide used in immune-oncology therapy.

Embodiment 39. A composition comprising anucleate cell-derived vesicles, wherein the anucleate cell-derived vesicles comprise a mutated Ras antigen; wherein the mutated Ras antigen is delivered to the anucleate cell-derived vesicles intracellularly.

Embodiment 40. The composition of embodiment 39, wherein the composition further comprises an adjuvant.

Embodiment 41. The composition of embodiment 40, wherein the adjuvant is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid, R837, R848, a TLR3 agonist, a TLR4 agonist or a TLR9 agonist.

Embodiment 42. The composition of embodiment 40 or 41, wherein the adjuvant is polyinosinic-polycytidylic acid.

Embodiment 43. A composition comprising anucleate cell-derived vesicles comprising a mutated Ras antigen or a mutated Ras antigen and an adjuvant, wherein the anucleate cell-derived vesicles comprising the mutated Ras antigen or the mutated Ras antigen and an adjuvant are prepared by a) passing a cell suspension comprising input anucleate cells through a cell-deforming constriction, wherein a diameter of the constriction is a function of a diameter of the input anucleate cells in the suspension, thereby causing perturbations of the input anucleate cells large enough for the mutated Ras antigen or the mutated Ras antigen and the adjuvant to pass through to form a perturbed input anucleate cells; and b) incubating the perturbed input anucleate cells with the mutated Ras antigen or the mutated Ras antigen and the adjuvant for a sufficient time to allow the mutated Ras antigen the mutated Ras antigen or the mutated Ras antigen and the adjuvant to enter the perturbed input anucleate cells; thereby generating anucleate cell-derived vesicles comprising the mutated Ras antigen or the mutated Ras antigen and the adjuvant.

Embodiment 44. A composition comprising anucleate cell-derived vesicles comprising a mutated Ras antigen, wherein the anucleate cell-derived vesicles comprising the mutated Ras antigen are prepared by a) passing a cell suspension comprising input anucleate cells through a cell-deforming constriction, wherein a diameter of the constriction is a function of a diameter of the input anucleate cells in the suspension, thereby causing perturbations of the input anucleate cells large enough for a nucleic acid encoding the mutated Ras antigen to pass through to form perturbed input anucleate cells; and b) incubating the perturbed input anucleate cells with the nucleic acid encoding the mutated Ras antigen for a sufficient time to allow the nucleic acid encoding the mutated Ras antigen to enter the perturbed input anucleate cells, wherein the nucleic acid expressed the mutated Ras antigen; thereby generating anucleate cell-derived vesicles comprising the mutated Ras antigen.

Embodiment 45. A composition comprising anucleate cell-derived vesicles comprising a mutated Ras antigen and an adjuvant, wherein the anucleate cells comprising the mutated Ras antigen and an adjuvant are prepared by a) passing a cell suspension comprising input anucleate cells through a cell-deforming constriction, wherein a diameter of the constriction is a function of a diameter of the input anucleate cells in the suspension, thereby causing perturbations of the input anucleate cells large enough for a nucleic acid encoding the mutated Ras antigen and for the adjuvant to pass through to form perturbed input anucleate cells; and b) incubating the perturbed input anucleate cells with the nucleic acid encoding the mutated Ras antigen and with the adjuvant for a sufficient time to allow the nucleic acid encoding the mutated Ras antigen and for the adjuvant to enter the perturbed input anucleate cells; wherein the nucleic acid encoding the mutated Ras antigen is expressed thereby generating anucleate cell-derived vesicles comprising the mutated Ras antigen and the adjuvant.

Embodiment 46. The composition of any one of embodiments 43-44, wherein the width of the constriction is about 10% to about 99% of the mean diameter of the input anucleate cells.

Embodiment 47. The composition of any one of embodiments 43-46, wherein the width of the constriction is about 1.6 μm to about 2.4 μm or about 1.8 μm to about 2.2 μm.

Embodiment 48. The composition of any one of embodiments 43-47, wherein the cell suspension comprising the input anucleate cells are passed through multiple constrictions wherein the multiple constrictions are arranged in series and/or in parallel.

Embodiment 49. The composition of any one of embodiments 43-48, wherein the input anucleate cell is a red blood cell or a platelet.

Embodiment 50. The composition of any one of embodiments 43-48, wherein the input anucleate cell is an erythrocyte or a reticulocyte.

Embodiment 51. The composition of any one of embodiments 38-48, wherein the anucleate cell-derived vesicle is a red blood cell-derived vesicle or a platelet-derived vesicle Embodiment 52. The composition of any one of embodiments 38-48, wherein the anucleate cell-derived vesicle is a reticulocyte-derived vesicle or a erythryocte-derived vesicle Embodiment 53. The composition of any one of embodiments 38-52, wherein the mutated Ras antigen is a mutated K-Ras antigen, a mutated H-Ras antigen, or a mutated N-Ras antigen.

Embodiment 54. The composition of any one of embodiments 38-53, wherein the mutated Ras antigen is a mutated K-Ras4A antigen or a mutated K-Ras4B antigen.

Embodiment 55. The composition of any one of embodiments 38-54, wherein the mutated Ras antigen is a single polypeptide that elicits a response against the same and or different mutated Ras antigens.

Embodiment 56. The composition of any one embodiments 38-55, wherein the mutated Ras antigen is a pool of multiple polypeptides that elicit a response against the same and or different mutated Ras antigens.

Embodiment 57. The composition of any one of embodiments 38-56, wherein the mutated Ras antigen complexes with other antigens or with an adjuvant.

Embodiment 58. The composition of any one of embodiments 38-57, wherein the mutated Ras antigen comprises a G12D mutation, a G12V mutation, a G12C mutation, or a G13D mutation.

Embodiment 59. The composition of any one of embodiments 38-58, wherein the mutated Ras antigen comprises an amino acid sequence with at least 90% similarity to any one of SEQ ID NOs:9-15.

Embodiment 60. The composition of any one of embodiments 38-59, wherein the mutated Ras antigen comprises an amino acid sequence of SEQ ID NOs:9-15.

Embodiment 61. The composition of any one of embodiments 51-60, wherein the mutated Ras antigen is one or more of a G12D1 16, a G12D2-19, a G12D2-22, a G12D2-29 antigen, a G12V1 16, a G12V2-19, a G12V3-17, or a G12V3-42 antigen.

Embodiment 62. The composition of any one of embodiments 38-61, wherein the mutated Ras antigen comprises an amino acid sequence with at least 90% similarity to any one of SEQ ID NOs:1-8.

Embodiment 63. The composition of any one of embodiments 38-62, wherein the mutated Ras antigen comprises an amino acid sequence of SEQ ID NOs:1-8.

Embodiment 64. The composition of any one of embodiments 38-63, wherein the mutated Ras antigen is a polypeptide comprising one or more antigenic mutated Ras epitopes that is flanked on the N-terminus and/or the C-terminus by one or more heterologous peptide sequences.

Embodiment 65. The composition of any one of embodiments 38-64, wherein the mutated Ras antigen is capable of being processed into an MHC class I-restricted peptide.

Embodiment 66. The composition of any one of embodiments 38-65, wherein the mutated Ras antigen is capable of being processed into an MHC class II-restricted peptide.

Embodiment 67. The composition of any one of embodiments 38-66, wherein the composition further comprises an adjuvant.

Embodiment 68. The composition of embodiment 67, wherein the adjuvant is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid, R837, R848, a TLR3 agonist, a TLR4 agonist or a TLR9 agonist.

Embodiment 69. The composition of embodiment 67 or 68, wherein the adjuvant is polyinosinic-polycytidylic acid.

Embodiment 70. A composition for stimulating an immune response to mutated Ras protein in an individual, wherein the composition comprises an effective amount of the composition of any one of embodiments 39-69.

Embodiment 71. A composition for reducing tumor growth in an individual, wherein the composition comprises an effective amount of the composition of any one of embodiments 39-69.

Embodiment 72. The composition of embodiment 70 or 71, wherein the individual has cancer.

Embodiment 73. A composition for treating cancer in an individual, wherein the composition comprises an effective amount of the composition of any one of embodiments 39-69.

Embodiment 74. The composition of embodiment 72 or 73, wherein the cancer is a pancreatic cancer, a colon cancer, a small intestine cancer, a biliary tract cancer, an endometrial cancer, a lung cancer, a skin cancer, an ovarian cancer, a stomach cancer, an esophageal cancer, a cervical cancer or a urinary tract cancer.

Embodiment 75. The composition of any one of embodiments 71-74, wherein the composition further comprises an adjuvant.

Embodiment 76. The composition of any one of embodiments 71-74, wherein the composition is administered in conjunction with an adjuvant.

Embodiment 77. The composition of embodiment 76, wherein the adjuvant is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid, R837, R848, a TLR3 agonist, a TLR4 agonist or a TLR9 agonist.

Embodiment 78. The composition of embodiment 76 or 77, wherein the adjuvant is polyinosinic-polycytidylic acid.

Embodiment 79. The composition of any one of embodiments 70-78, wherein the composition comprising anucleate cells is administered a plurality of times.

Embodiment 80. The composition of any one of embodiments 70-79, wherein the composition is administered intravenously.

Embodiment 81. The composition of any one of embodiments 70-80, wherein the individual is a human.

Embodiment 82. The composition of any one of embodiments 70-81, wherein the composition is administered prior to, concurrently with, or following administration of another therapy.

Embodiment 83. The composition of embodiment 82, wherein another therapy is a chemotherapy, a radiation therapy, an antibody, a cytokine, an immune checkpoint inhibitor, or a bispecific polypeptide used in immune-oncology therapy.

Embodiment 84. Use of a composition comprising an effective amount of anucleate cells in the manufacture of a medicament for stimulating an immune response to mutated Ras, wherein the composition comprises an effective amount of the composition of any one of embodiments 39-69.

Embodiment 85. Use of a composition comprising an effective amount of anucleate cells in the manufacture of a medicament for reducing tumor growth in an individual, wherein the composition comprises an effective amount of the composition of any one of embodiments 39-69.

Embodiment 86. The use of embodiment 84 or 85, wherein the individual has cancer.

Embodiment 87. Use of a composition comprising an effective amount of anucleate cell-derived vesicles in the manufacture of a medicament for treating cancer in an individual, wherein the composition comprises an effective amount of the composition of any one of embodiments 38-61.

Embodiment 88. The use of embodiment 86 or 87, wherein the cancer is a pancreatic cancer, a colon cancer, a small intestine cancer, a biliary tract cancer, an endometrial cancer, a lung cancer, a skin cancer, an ovarian cancer, a stomach cancer, an esophageal cancer, a cervical cancer or a urinary tract cancer.

Embodiment 89. The use of any one of embodiments 84-88, wherein the composition further comprises an adjuvant.

Embodiment 90. The use of any one of embodiments 84-89, wherein the composition is formulated for administration in conjunction with an adjuvant.

Embodiment 91. The use of embodiment 90, wherein the adjuvant is a a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid, R837, R848, a TLR3 agonist, a TLR4 agonist or a TLR9 agonist.

Embodiment 92. The use of any one of embodiments 84-89, wherein the adjuvant is polyinosinic-polycytidylic acid.

Embodiment 93. The use of any one of embodiments 84-92, wherein the composition comprising anucleate cell-derived vesicles is administered a plurality of times.

Embodiment 94. The use of any one of embodiments 84-93, wherein the composition is administered intravenously.

Embodiment 95. The use of any one of embodiments 84-94, wherein the individual is a human.

Embodiment 96. The use of any one of embodiments 84-95, wherein the composition is administered prior to, concurrently with, or following administration of another therapy.

Embodiment 97. The use of embodiment 96, wherein another therapy is a chemotherapy or a radiation therapy, an antibody, a cytokine, an immune checkpoint inhibitor, or a bispecific polypeptide used in immune-oncology therapy.

Embodiment 98. A kit for use in the method of any one of embodiments 1-38.

Embodiment 99. A kit comprising the composition of any one of embodiments 39-69.

Embodiment 100. The kit of embodiment 98 or 99, wherein the kit further comprises one or more of buffers, diluents, filters, needles, syringes, or package inserts with instructions for administering the composition to an individual to stimulate an immune response to a mutated Ras, reduce tumor growth and/or treat cancer.

Embodiment 101. A method for producing a composition of anucleate cell-derived vesicles comprising a mutated Ras antigen; the method comprising introducing the mutated Ras antigen to the anucleate cell-derived vesicles intracellularly.

Embodiment 102. The method of embodiment 101, wherein the anucleate cell further comprises an adjuvant.

Embodiment 103. The method of embodiment 102, wherein the adjuvant is a a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid, R837, R848, a TLR3 agonist, a TLR4 agonist or a TLR9 agonist.

Embodiment 104. The method of embodiment 102 or 103, wherein the adjuvant is polyinosinic-polycytidylic acid.

Embodiment 105. The method of embodiment 104, wherein introducing the mutated Ras antigen or the mutated Ras antigen and the adjuvant to anucleate cell-derived vesicles intracellularly comprises a) passing a cell suspension comprising input anucleate cells through a cell-deforming constriction, wherein a diameter of the constriction is a function of a diameter of the input anucleate cells in the suspension, thereby causing perturbations of the input anucleate cells large enough for the mutated Ras antigen or the mutated Ras antigen and the adjuvant to pass through to form perturbed input anucleate cells; and b) incubating the perturbed input anucleate cells with the mutated Ras antigen or the mutated Ras antigen and the adjuvant for a sufficient time to allow the mutated Ras antigen or the mutated Ras antigen and the adjuvant to enter the perturbed input anucleate cells; thereby generating anucleate cell-derived vesicles comprising the mutated Ras antigen or the mutated Ras antigen and the adjuvant.

Embodiment 106. The method of embodiment 104, wherein introducing the mutated Ras antigen to the anucleate cell-derived vesicles intracellularly comprises a) passing a cell suspension comprising input anucleate cells through a cell-deforming constriction, wherein a diameter of the constriction is a function of a diameter of the input anucleate cells in the suspension, thereby causing perturbations of the input anucleate cells large enough for a nucleic acid encoding the mutated Ras antigen to pass through to form a perturbed input anucleate cells; and b) incubating the perturbed input anucleate cells with the nucleic acid encoding the mutated Ras antigen for a sufficient time to allow the nucleic acid encoding the mutated Ras antigen to enter the perturbed input anucleate cells, wherein the nucleic acid expressed the mutated Ras antigen; thereby generating anucleate cells comprising the mutated Ras antigen.

Embodiment 107. The method of embodiment 104, wherein the anucleate cell-derived vesicles further comprises an adjuvant intracellularly, wherein introducing the mutated Ras antigen and the adjuvant to the anucleate cell intracellularly comprises a) passing a cell suspension comprising input anucleate cells through a cell-deforming constriction, wherein a diameter of the constriction is a function of a diameter of the input anucleate cells in the suspension, thereby causing perturbations of the input anucleate cells large enough for a nucleic acid encoding the mutated Ras antigen and for the adjuvant to pass through to form perturbed input anucleate cells; and b) incubating the perturbed input anucleate cells with the nucleic acid encoding the mutated Ras antigen and with the adjuvant for a sufficient time to allow the nucleic acid encoding the mutated Ras antigen and for the adjuvant to enter the perturbed input anucleate cells; wherein the nucleic acid encoding the mutated Ras antigen is expressed thereby generating anucleate cell-derived vesicles comprising the mutated Ras antigen and the adjuvant.

Embodiment 108. The method of any one of embodiments 105-107, wherein the width of the constriction is about 10% to about 99% of the mean diameter of the input anucleate cells.

Embodiment 109. The method of any one of embodiments 105-108, wherein the width of the constriction is about 1.6 μm to about 2.4 μm or about 1.8 μm to about 2.2 μm.

Embodiment 110. The method of any one of embodiments 105-109, wherein the cell suspension comprising the plurality of input anucleate cells are passed through multiple constrictions wherein the multiple constrictions are arranged in series and/or in parallel.

EXAMPLES

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

Example 1

In order to determine if anucleate cell vesicles squeeze-loaded with a mutant K-Ras antigen can be internalized by human antigen presenting cells (APCs), red blood cells from healthy human donors are squeeze-processed in the presence of one or more mutated K-Ras antigens and the resulting antigen-loaded anucleate vesicles are tested for in vitro uptake by dendritic cells.

Methods

Monocyte-derived dendritic cells (MODCs) are generated from HLA donors through a five-day GM-CSF/IL-4 differentiation from $CD14^+$ monocytes. These MODCs can be used as an in vitro model of human APCs (in this and other examples throughout the application). HLA donors may be from any subgroup, including subgroups HLA-A*02, HLA-A*11, HLA-B*07, HLA-C*08.

PKH26 labelled AAC-K-Ras (activating antigen carrier comprising K-Ras antigen and adjuvant) are generated by taking red blood cells (RBCs) from healthy human donors and labelling them with PKH26, a lipophilic fluorescent membrane dye, prior to squeeze-processing the RBCs with two synthetic long peptides (SLPs) comprising mutated K-Ras antigen(s) and an adjuvant, to form PKH26-labeled anucleate cell vesicles comprising the mutated K-Ras antigen(s) and the adjuvant (AAC-K-Ras). The two SLPs may be 1 or more G12D SLPs, 1 or more G12V SLPs, or a combination of 2 or more SLPs selected from at least 1 G12D SLP and at least 1 G12V SLP. The adjuvant may be an adjuvant known in the art, including polyinosinic-polycytidylic acid (poly I:C). Human donor MODCs are then co-cultured overnight with PKH26-labeled AAC-K-Ras at 37° C. or 4° C., and washed 3 times with FACS buffer. To assay for AAC-K-Ras internalization, the MODC samples are assayed via flow cytometry and PKH26 fluorescence associated with the MODCs is analyzed using FlowJo software.

Results

PKH26 fluorescence (average±standard deviation of the mean of biological replicates or triplicates) are detected from MODCs co-cultured with PKH26-labeled AAC-K-Ras at 37° C. and 4° C., to demonstrate the in vitro uptake of Squeeze-AAC-K-Ras by human APCs.

Example 2

In order to determine whether antigen-specific response is induced by antigen-presenting cells following internalization of AAC-K-Ras generated from RBCs, the activation of antigen-specific responder T cells after in vitro co-cultures with AAC-K-Ras and MODCs is measured by IFN-γ expression or secretion assays.

Methods

The readout of AAC-K-Ras functionality can be determined by measuring IFN-7 secretion in the conditioned medium containing in vitro co-cultures of AAC-K-Ras, MODCs, and antigen specific $CD8^+$ T cell responders. Red blood cells (RBCs) from 2 healthy human donors are squeeze processed with a mixture of two synthetic long peptides (SLPs)(either 1 or more from G12D, 1 or more from G12V, or a combination of G12D and G12V peptides) and the adjuvant polyinosinic-polycytidylic acid (poly I:C), to generate AAC-KRAS. G12D and G12V SLPs contain HLA restricted epitopes, the presentation of which can induce antigen-specific T cell response against cells containing the respective K-Ras mutants. Different batches of AAC-K-Ras are individually co-cultured with HLA+ MODCs and HLA+ restricted $CD8^+$ T cells, and the level of IFN-γ expression and/or secretion may be measured by ELISA, ELISPOT, or flow cytometry-based assays.

MODCs are generated by stimulation of $CD14^+$ monocytes isolated from an HLA haplotyped healthy donor with granulocyte-macrophage colony-stimulating factor and interleukin-4 for five days. MODCs co-cultured with K-Ras mutant specific $CD8^+$ T cells in media (without AACs) is used as a negative control. To distinguish AAC-K-Ras-dependent activity from activity of the surrounding medium, a solution containing AAC-K-Ras fluid phase is co-cultured with MODCs and K-Ras mutant specific $CD8^+$ T cells. MODCs incubated in the presence of free K-Ras mutant SLP and co-cultured with K-Ras mutant specific $CD8^+$ T cells serves as a positive control. Lipopolysaccharide (LPS) is used to enhance MODCs processing of AAC-K-Ras in vitro and is applied to all co-culture groups for control purpose. The amount of IFN-γ secreted is determined using a human IFN-γ ELISA.

Results

The change in responder IFN-γ expression and/or secretion induced by co-culture of MODCs and responders with AAC-K-Ras generated from donor RBCs is compared to that from co-culture with wild type K-Ras controls, the fluid phase solution controls and untreated controls, in order to demonstrate any in vitro uptake of AAC-K-Ras by human antigen presenting cells (APCs) which results in the presentation of HLA-restricted mutant K-Ras epitopes by MODCs which in turn elicits functional antigen-specific responses from $CD8^+$ T cells that recognize the mutant K-Ras minimal epitope.

Example 3

In order to determine whether incubation with AAC-K-Ras can mediate in vitro maturation of antigen presenting cells, AAC-K-Ras is co-cultured with MODCs and the change in maturation markers of MODCs are assessed using flow cytometry.

Methods

Monocyte-derived dendritic cells (MODCs) are generated from HLA donors through a five-day GM-CSF/IL-4 differentiation of CD14+ monocytes. These MODCs are used as an in vitro model of human APCs. HLA donors are from any subgroup, including subgroups HLA-A*02, HLA-A*11, HLA-B*07, HLA-C*08.

AAC-K-Ras are generated by taking RBCs from 3 healthy human donors and squeeze-processing with a mixture of two synthetic long peptides (SLPs) (either 1 or more G12D SLPs, 1 or more G12V SLPs, or a combination of 2 or more G12D and G12V SLPs) and the adjuvant polyinosinic-polycytidylic acid (poly I:C), to generate AAC-K-Ras comprising the adjuvant and the respective mixtures of SLPs. G12D and G12V SLPs contain HLA restricted epitopes, the presentation of which can induce antigen-specific T cell response against cells containing the respective K-Ras mutants. Three batches of AAC-K-Ras are individually co-cultured with $HLA^+$ MODCs and upregulation of maturation markers (CD80, CD86, CD83, MHC-II) is assessed by flow cytometry after about 46 hrs of co-culture. Data is compared to media & empty control.

Results

Following incubation of AAC-K-Ras with human MODCs antigen presenting cells (APCs), the changes in levels of maturation markers (CD80, CD86, CD83, MHC-II) on the MODCs are measured, an upregulation of one or more of which can indicate that the respective AAC-K-Ras can mediate in vitro maturation of MODCs.

Example 4

In order to determine if human RBCs squeeze-processed with a mutant K-Ras-G12D antigen can activate antigen specific responder T cells in vitro, human RBCs are squeeze-processed with G12D antigen, and the activity of G12D specific responder T cells (e.g. IFN-γ expression and/or secretion) after co-culture with APCs contacted with RBCs squeeze-loaded with G12D antigen may be measured via ELISPOT, ELISA or flow cytometry-based assay.

Methods

Human donor RBCs are isolated. Cells are squeeze-processed at room temperature through a microfluidic chip at a density of $2\times10^9$ RBCs/mL at 60 psi with 100 μM synthetic long peptide (G12D) or vehicle (DMSO) control in RPMI. Following squeeze processing, RBCs are centrifuged, and the supernatant is discarded. Cells are washed one time in R10 media and then twice in CTL medium (supplemented with 1% glutamine) before resuspension in CTL medium (supplemented with 1% glutamine).

Squeeze-processed RBCs comprising the G12D antigen and adjuvant (AACs) are then incubated with APCs and K-Ras G12D responder T cells on an ELISPOT plate. After any internalization of AACs comprising G12D antigen, the effect of APCs presenting the HLA-restricted G12D epitope on K-Ras G12D responder T cells can be measured by ELISPOT assays. As a positive control, K-Ras G12D peptide containing the minimal epitope is added directly to untreated MODCs and responder cells in the ELISPOT plate. The plate is incubated overnight at 37° C. and developed/quantified according to manufacturer's instructions.

Results

After incubation of APCs with AACs squeeze-loaded with G12D antigen, and G12D-specific responder T cells, the amount of IFN-γ expressing T cells is measured via ELISPOT assay, an upregulation of which indicates that AACs squeeze-loaded with G12D antigen are capable of being internalized by APCs and subsequently mediates the activation of antigen-specific T cell response.

Example 5

In order to determine if human RBCs squeeze-processed with a mutant K-Ras antigen can activate antigen specific responder T cells in vitro, human RBCs are squeeze-processed with G12D antigen, and the activity of G12D specific responder T cells (e.g. IFN-γ expression and/or secretion) after co-culture with APCs contacted with RBCs squeeze-loaded with G12D antigen may be measured via ELISPOT, ELISA or flow cytometry-based assay.

Methods

Human donor RBCs are isolated and squeeze-processed at room temperature through a microfluidic chip at 60 psi with 100 μM synthetic long peptide (wild type K-Ras or K-Ras G12D) or vehicle (DMSO) control in RPMI. Following squeeze-processing, RBCs are centrifuged, and the supernatant is discarded. Cells are washed one time in R10 medium and then twice in CTL medium (supplemented with 1% glutamine) before resuspension in CTL medium (supplemented with 1% glutamine). Squeeze-processed RBCs comprising an adjuvant and either WT K-Ras or G12D antigen (AACs) are then incubated with APCs and K-Ras G12D responder T cells on an ELISPOT plate. After any internalization of AACs comprising WT K-Ras or G12D antigen, the effect of APCs presenting the HLA-restricted WT K-Ras or G12D epitope on K-Ras G12D responder T cells can be measured by ELISPOT assays. As controls, peptide containing either the WT or G12D versions of the minimal epitope are added directly to untreated MODCs and responder cells in the ELISPOT plate. The plate is incubated overnight at 37° C. and developed/quantified according to manufacturer's instructions.

Results

After incubation of APCs with AAC squeeze-loaded with G12D antigen and G12D-specific responder T cells, the amount of IFN-γ expressing T cells is measured via ELISPOT assay, an upregulation of which indicates that AACs squeeze-loaded with G12D antigen are capable of being internalized by APCs and subsequently mediates the activation of antigen-specific T cell response. Further, an upregulation of amount of IFN-γ expressing T cells mediated by AAC squeeze-loaded with G12D contrasted with lack of comparable effects by AACs squeeze-loaded with wild type K-Ras antigen can further illustrate that the activation of antigen-specific T cell response is mutation-specific.

Example 6

In order to determine if human RBCs squeeze-processed with a mutant K-Ras-G12V antigen can activate antigen specific responder T cells in vitro, human RBCs are squeeze-processed with G12V antigen, and the activity of G12V specific responder T cells (e.g. IFN-γ expression and/or secretion) after co-culture with APCs contacted with RBCs squeeze-loaded with G12V antigen may be measured via ELISPOT, ELISA or flow cytometry-based assay.

Methods

Human donor RBCs are isolated. Cells are squeeze-processed at room temperature through a microfluidic chip at a density of $2\times10^9$ RBCs/mL at 60 psi with 100 μM synthetic long peptide (G12V) or vehicle (DMSO) control in RPMI. Following squeeze processing, RBCs are centrifuged, and the supernatant is discarded. Cells are washed one time in R10 media and then twice in CTL medium (supplemented with 1% glutamine) before resuspension in CTL medium (supplemented with 1% glutamine).

Squeeze-processed RBCs comprising the G12V antigen and adjuvant (AACs) are then incubated with APCs and K-Ras G12V responder T cells on an ELISPOT plate. After any internalization of AACs comprising G12V antigen, the effect of APCs presenting the HLA-restricted G12V epitope on K-Ras G12V responder T cells can be measured by ELISPOT assays. As a positive control, K-Ras G12V peptide containing the minimal epitope is added directly to untreated MODCs and responder cells in the ELISPOT plate. The plate is incubated overnight at 37° C. and developed/quantified according to manufacturer's instructions.

Results

After incubation of APCs with AAC squeeze-loaded with G12V antigen and subsequently with G12V-specific responder T cells, the amount of IFN-γ expressing T cells is measured via ELISPOT assay, an upregulation of which indicates that AACs squeeze-loaded with G12V antigen are capable of being internalized by APCs and subsequently mediates the activation of antigen-specific T cell response.

Example 7

In order to determine if human RBCs squeeze-processed with a combination of G12D and G12V antigens can mediate activation of antigen specific responder T cells in vitro, human RBCs are squeeze-processed with a combination of G12D and G12V antigens, and the activity of G12D specific responder T cells (e.g. IFN-γ expression and/or secretion) after co-culture with APCs contacted with RBCs squeeze-loaded with a combination of G12D and G12V antigens is measured via ELISPOT, ELISA or flow cytometry-based assay.

Methods

Human donor RBCs are isolated and squeeze-processed at room temperature through a microfluidic chip at 60 psi with either a single G12D synthetic long peptide (SLP), a combination of 1 G12D SLP and 1 G12V SLP, or vehicle (DMSO) control in RPMI. Following squeeze-processing, the RBCs are centrifuged, and the supernatant is discarded. Cells are washed one time in R10 medium and then twice in CTL medium (supplemented with 1% glutamine) before resuspension in CTL medium (supplemented with 1% glutamine).

Squeeze-processed RBCs (AACs) comprising the respective antigens are incubated with APCs and K-Ras G12D responder T cells on an ELISPOT plate. After any internalization of AACs comprising G12D antigen, the effects of APCs presenting the HLA-restricted G12D epitope on K-Ras G12D responder T cells can be measured by ELISPOT assays in an. As a positive control, K-Ras G12D peptide containing the minimal epitope is added directly to untreated MODCs and responder cells in the ELISPOT plate. The plate is incubated overnight at 37° C. and developed/quantified according to manufacturer's instructions.

Results

After incubation of APCs with AACs (squeeze-loaded with either G12D antigen or a combination of G12D and G12V antigens), and with G12D-specific responder T cells, the amount of IFN-γ expressing responders is measured via ELISPOT assay, where a comparable upregulation induced by APCs contacted with either AAC sample will indicate that RBCs squeeze processed with a combination of K-Ras-G12 mutant SLPs can activate G12D responder T cells in vitro to a similar extent as RBCs squeeze processed with G12D only, and that the addition of G12V SLP payload to G12D SLP-comprising AACs causes no significant changes to the responses of G12D-specific T cells mediated by G12D SLP-comprising AACs.

Example 8

In order to determine if human RBCs squeeze-processed with a combination of G12D and G12V antigens can mediate activation of antigen specific responder T cells in vitro, human RBCs are squeeze-processed with a combination of G12D and G12V antigens, and the activity of G12V specific responder T cells (e.g. IFN-γ expression and/or secretion) after co-culture with APCs contacted with RBCs squeeze-loaded with a combination of G12D and G12V antigens is measured via ELISPOT assay.

Methods

Human donor RBCs are isolated and squeeze-processed at room temperature through a microfluidic chip at 60 psi with either a single G12V synthetic long peptide (SLP), a combination of 1 G12D SLP and 1 G12V SLP, or vehicle (DMSO) control in RPMI. Following squeeze-processing, the RBCs are centrifuged, and the supernatant is discarded. Cells are washed one time in R10 medium and then twice in CTL medium (supplemented with 1% glutamine) before resuspension in CTL medium (supplemented with 1% glutamine).

Squeeze-processed RBCs (AACs) comprising the respective antigens are incubated with APCs and K-Ras G12V responder T cells on an ELISPOT plate. After any internalization of AACs comprising G12V antigen, the effects of APCs presenting the HLA-restricted G12V epitope on K-Ras G12V responder T cells can be measured by ELISPOT assays. As a positive control, K-Ras G12V peptide containing the minimal epitope is added directly to untreated MODCs and responder cells in the ELISPOT plate. The plate is incubated overnight at 37° C. and developed/quantified according to manufacturer's instructions.

Results

After incubation of APCs with AACs (squeeze-loaded with either G12V antigen or a combination of G12D and G12V antigens), and with G12V-specific responder T cells, the amount of IFN-γ expressing T cells is measured via ELISPOT assay, where a comparable upregulation induced by APCs contacted with either AAC sample will indicate that RBCs squeeze processed with a combination of K-Ras-G12 mutant SLPs can activate G12V responder T cells in vitro to a similar extent as RBCs squeeze processed with G12V only and that the addition of G12V SLP payload to G12D SLP-comprising AACs causes no significant changes to the responses of G12V-specific T cells mediated by G12V SLP-comprising AACs.

Example 9

In order to determine whether human RBCs can be squeeze-loaded with a K-Ras synthetic long peptide, human RBCs were squeeze-processed with a FAM-labeled with K-Ras G12V$^{1-16}$ SLP. The squeeze-loaded RBCs (AACs) were then analyzed using flow cytometry for FAM fluorescence.

Methods

Human RBCs were isolated and incubated with synthetic long peptide in RPMI at room temperature (RT), 37° C., or ice for at least 15 minutes. RBC were then squeeze-processed at a density of $2\times10^9$ cells/mL through a microfluidic constriction of 2.2 μm width, 10 μm length and 70 μm depth, at 60 psi and in the presence of 100 μM FAM-labeled K-Ras G12V$^{1-16}$. Cells were resuspended in RPMI supplemented with DMSO to a final concentration of 5%. Following squeeze-processing, RBCs were held at the same temperature (RT, 37° C., or ice respectively) for 20 minutes, washed five times with PBS, enriched for AACs (by centrifugation and collecting the top, light colored layer of the pellet that forms), and then resuspended in PBS. The resulting AACs are also stained with annexin V (data not shown). AACs comprising the FAM-labeled SLPs were then analyzed using flow cytometry to register FAM$^+$ events.

Results

As shown in FIG. 1, the increase in FAM label fluorescence indicates human AACs can be loaded with a G12V$^{1-16}$ SLP. In addition, squeeze-mediated loading was effective across all squeeze/holding temperatures tested, including at RT (25° C.), 37° C., and on ice (4° C.).

Example 10

In order to determine whether human RBCs can be squeeze-loaded with a K-Ras synthetic long peptide, human RBCs were squeeze-processed in the presence of FAM-labeled K-Ras G12D$^{1-16}$ or K-Ras G12D$^{2-19}$ SLP. AACs were then analyzed using flow cytometry for FAM$^+$ events.

Methods

Human RBCs were isolated and squeeze-processed at a density of $2\times10^9$ cells/mL through a microfluidic constriction of 2.2 μm width, 10 μm length and 70 μm depth, at 60 psi and in the presence of 100 μM FAM-labeled K-Ras G12D$^{1-16}$ or K-Ras-G12D$^{2-19}$. Cells were resuspended in RPMI supplemented with DMSO to a final concentration of 5%. Following squeeze-processing, samples were incubated at room temperature for 20 minutes, washed five times with PBS, enriched for AACs (by centrifugation and collecting the top, light colored layer of the pellet that forms), and then resuspended in PBS. AACs comprising the FAM-labeled SLPs were then analyzed using flow cytometry to register FAM$^+$ events.

Results

Figure 2:
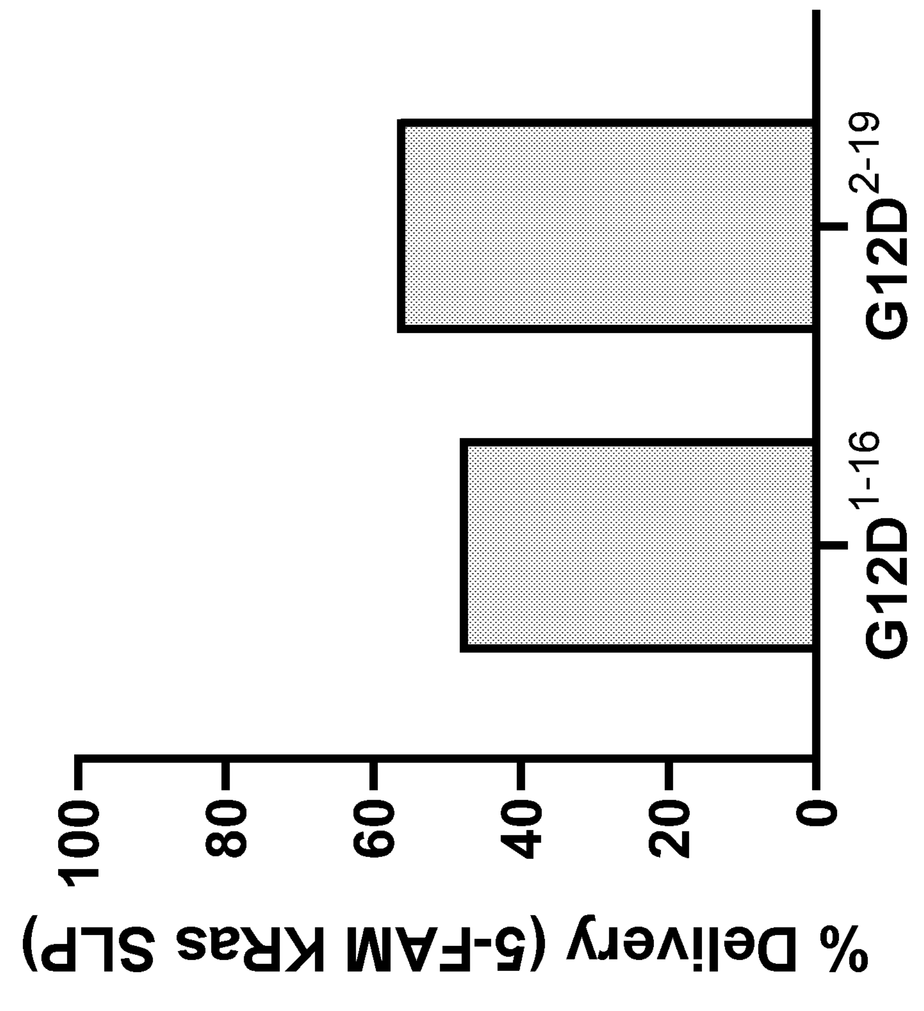
FIG. 2 shows the efficacy of intracellular delivery of two fluorescently labeled mutant Ras synthetic long peptides into RBCs by constriction-mediated delivery (squeeze).

As shown in FIG. 2, the increase in FAM label fluorescence indicates human AACs can be efficiently loaded with both the G12D$^{1-16}$ or G12D$^{2-19}$ SLP, with delivery into at least 40% of the AACs.

Example 11

To determine the efficacy of co-administration of antigen carriers (ACs) and adjuvant as a boosting vaccination in eliciting an antigen specific responder T cells in vivo, murine RBCs were squeeze-processed with G12V antigen, and co-administered with poly I:C to HLA-A*11 transgenic mice in various boosting schedules. The activity of specific responder cells harvested from the immunized mice (e.g. IFN-γ expression and/or secretion) after stimulation with G12V antigen was measured via ELISPOT.

Methods

Murine donor RBCs were isolated. The RBCs were squeeze-processed at room temperature through a microfluidic chip (2.2 μm width, 10 μm length, 70 μm depth) at a density of $1\times10^9$ RBCs/mL at 50 psi in the presence of 200 μM synthetic long peptide (G12V$^{1-16}$ SLP) in RPMI. Unprocessed RBCs were also used as control (no contact). Following squeeze-processing, the processed RBCs were rested at room temperature for 40 minutes, then centrifuged (at 8000×g) and washed in PBS before resuspension in either PBS or CTL medium (supplemented with 1% glutamine). The squeeze-processed RBCs comprising the G12V$^{1-16}$ SLP (antigen carriers AC$^{G12V1-16}$) were enriched (e.g. through physical separation) for the ghost population within the ACs (enriched). Control RBCs (no contact) and the AC populations (pre-enriched ACs, enriched ACs) were analyzed for cell surface phosphatidylserine (Annexin V staining).

Figure 3A:
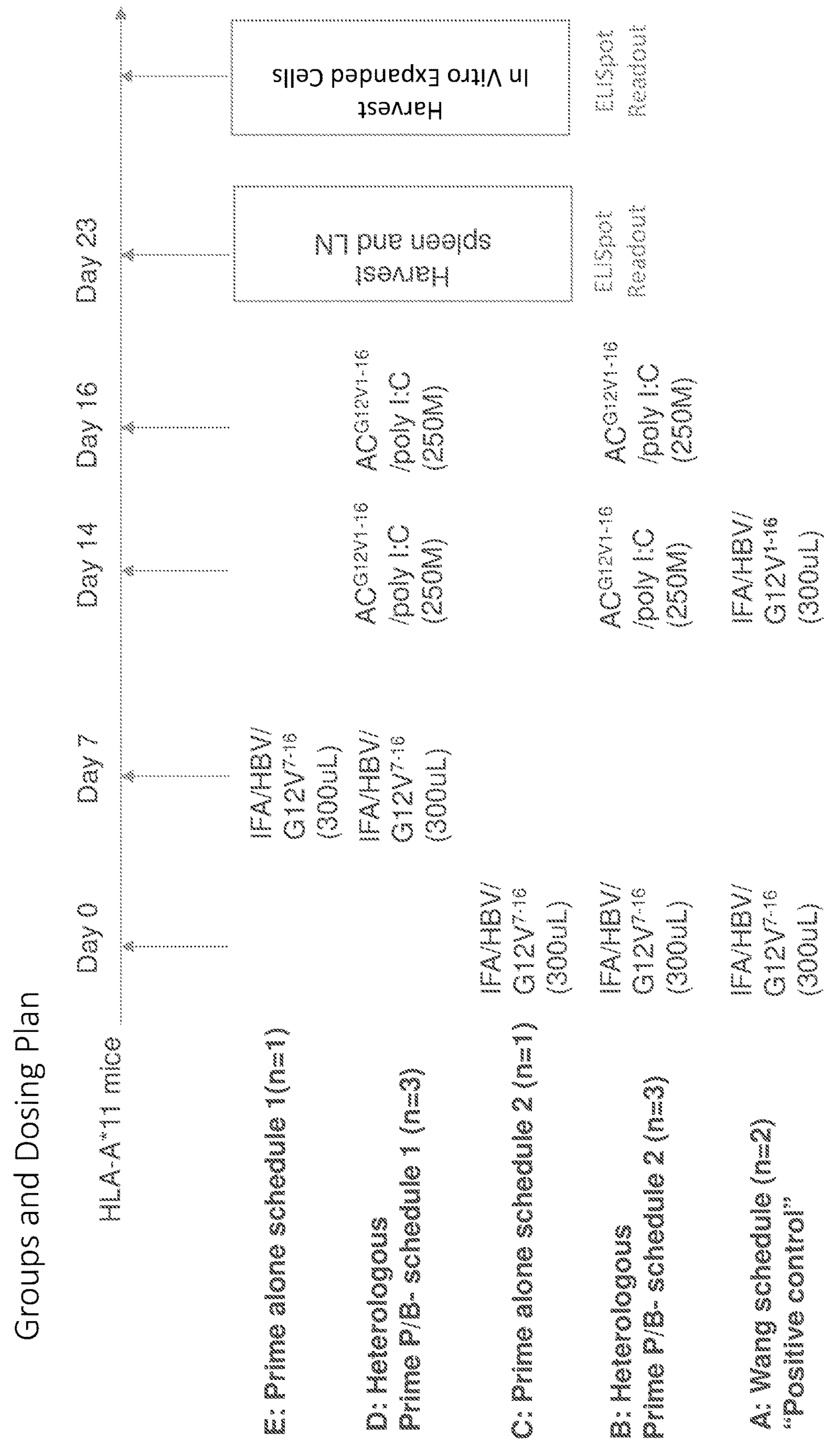
FIG. 3A is a schematic of the dosing groups and schedules showing administrations of IFA/HBV/G12V$^{7-16}$ (emulsion of peptides) and/or AC$^{G12V1-16}$/poly I:C (antigen carriers comprising KRas-G12V$^{1-16}$ co-administered with poly I:C) in a murine model, and the subsequent tissue harvests and assays for immune activity (IFN-γ ELISPOT).

An emulsion containing K-Ras short peptide (G12V$^{7-16}$)/HBV core peptide/IFA (See Wang et al., *Cancer Immunol Res.* 2016 March; 4(3):204-14) was administered as the prime vaccination (KRas/HBV/IFA; IFA prime); whereas subsequently either an additional KRas/HBV/IFA emulsion (IFA boost), or ACs$^{G12V1-16}$ (250 million ACs)+1 mg/mL Poly I:C (AC/Poly I:C boost) were retro-orbitally (RO) administered as the boost vaccination, to HLA-A*11 transgenic mice according to the dosing groups and schedules shown in FIG. 3A and FIG. 3B. PBS administration was used as a control.

Figure 3C:
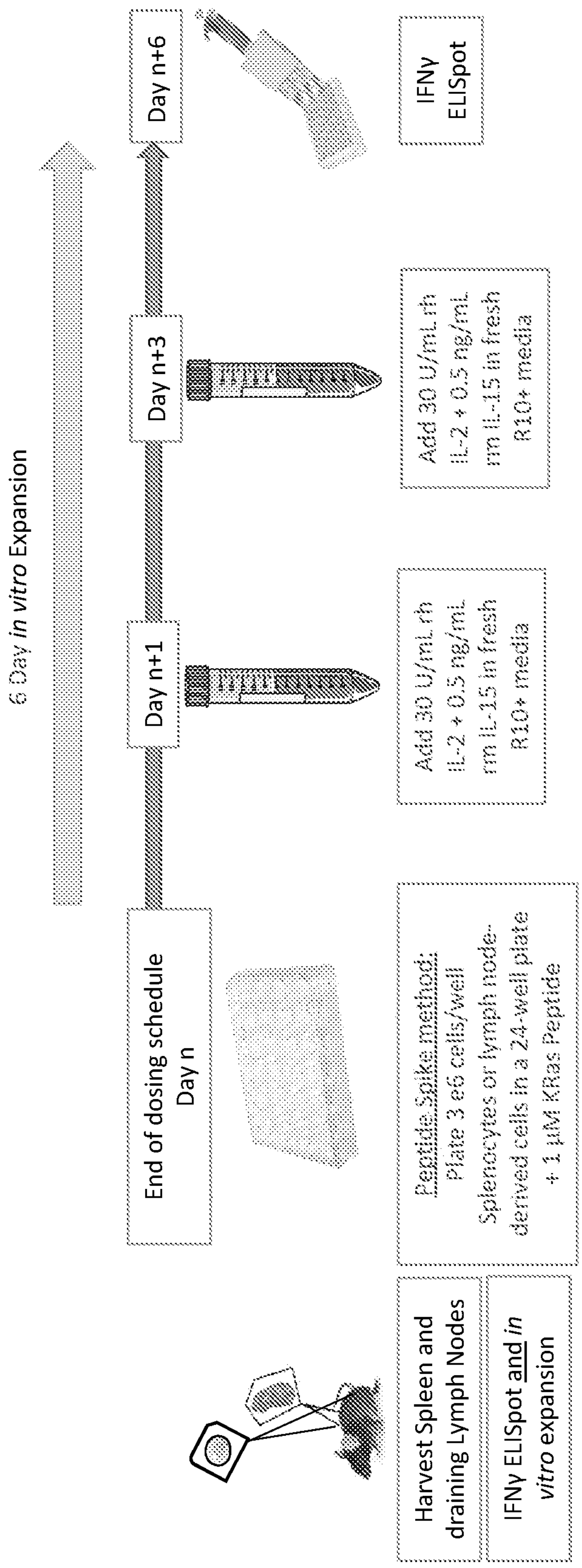
FIG. 3C illustrates the in vitro expansion workflow subsequent to tissue harvest from the murine model.

At the end of the described dosing schedule (take-down), the spleen and/or draining lymph nodes were harvested from the treated or control mice, wherein the splenocytes or lymph-node derived cells were treated with spiking of 1 μM G12V$^{7-16}$ K-Ras Peptide or a non-relevant control peptide (MART1), and either subjected to IFN-γ ELISPOT assay immediately (take-down) or subjected to IFN-γ ELISPOT assay after 6 days of in vitro expansion, as shown in FIG. 3C.

Results

Figure 3D:
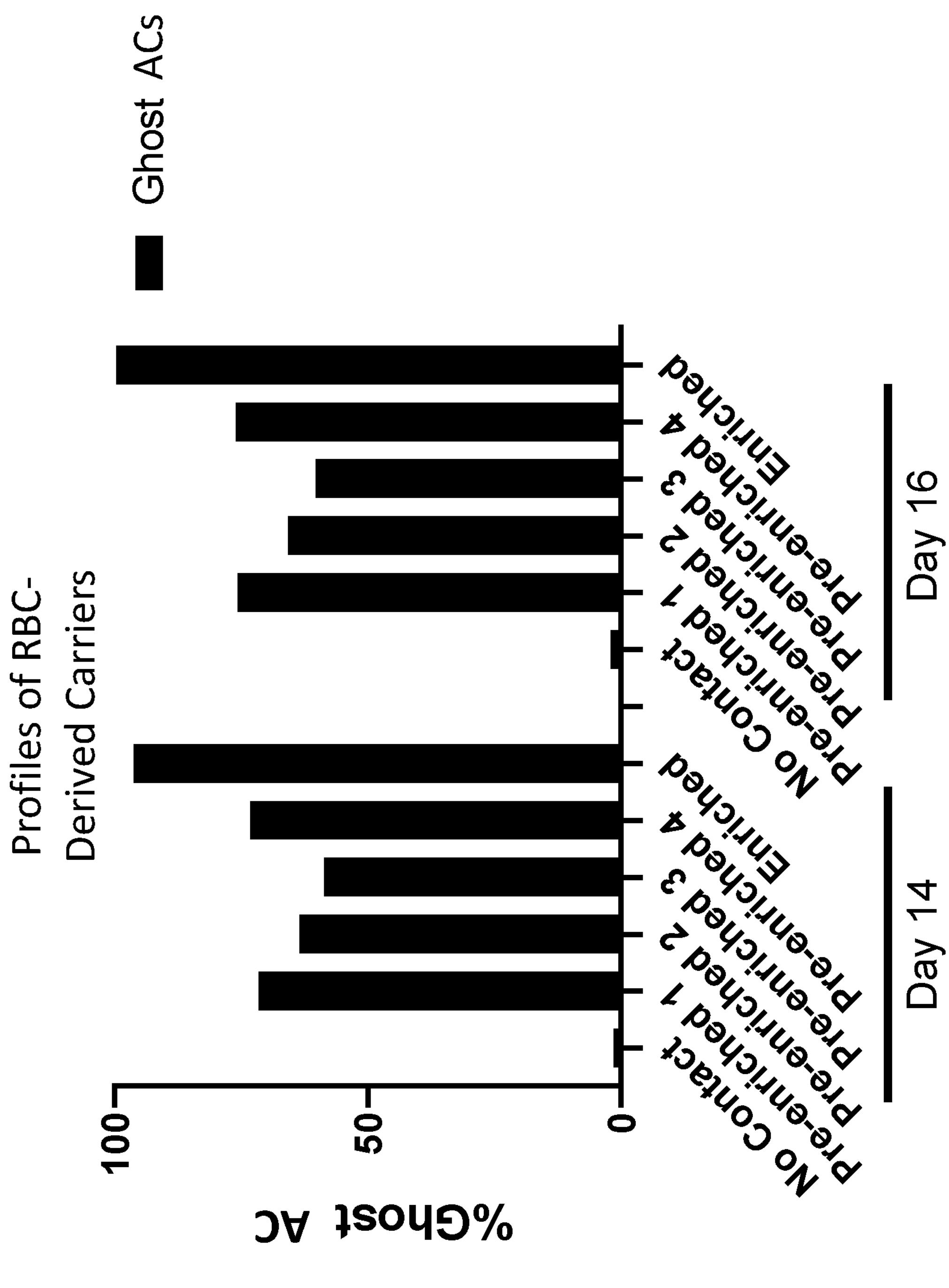
FIG. 3D shows the percentage of ghost populations within the indicated red blood cell-derived carriers (antigen carriers) subsequent to squeeze-processing, or subsequent to squeeze-processing and enrichment.
Figure 3E:
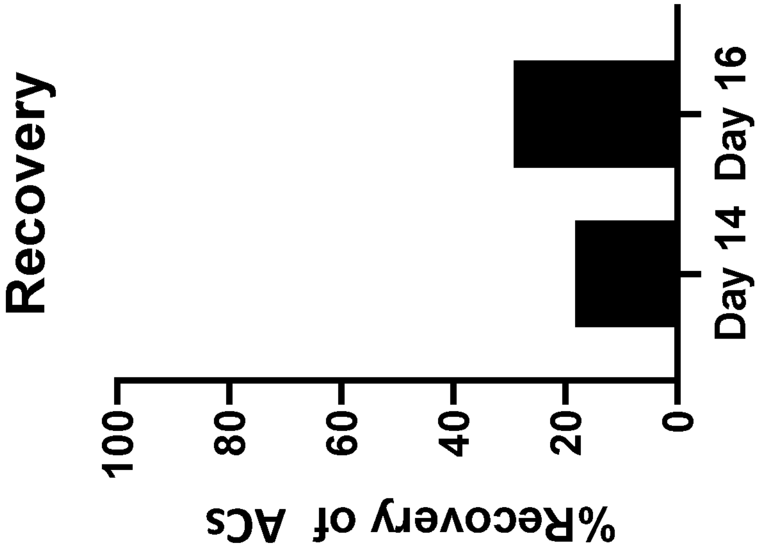
FIG. 3E shows the percentage of recovery of antigen carriers subsequent to squeeze-processing of RBCs.
Figure 3F:
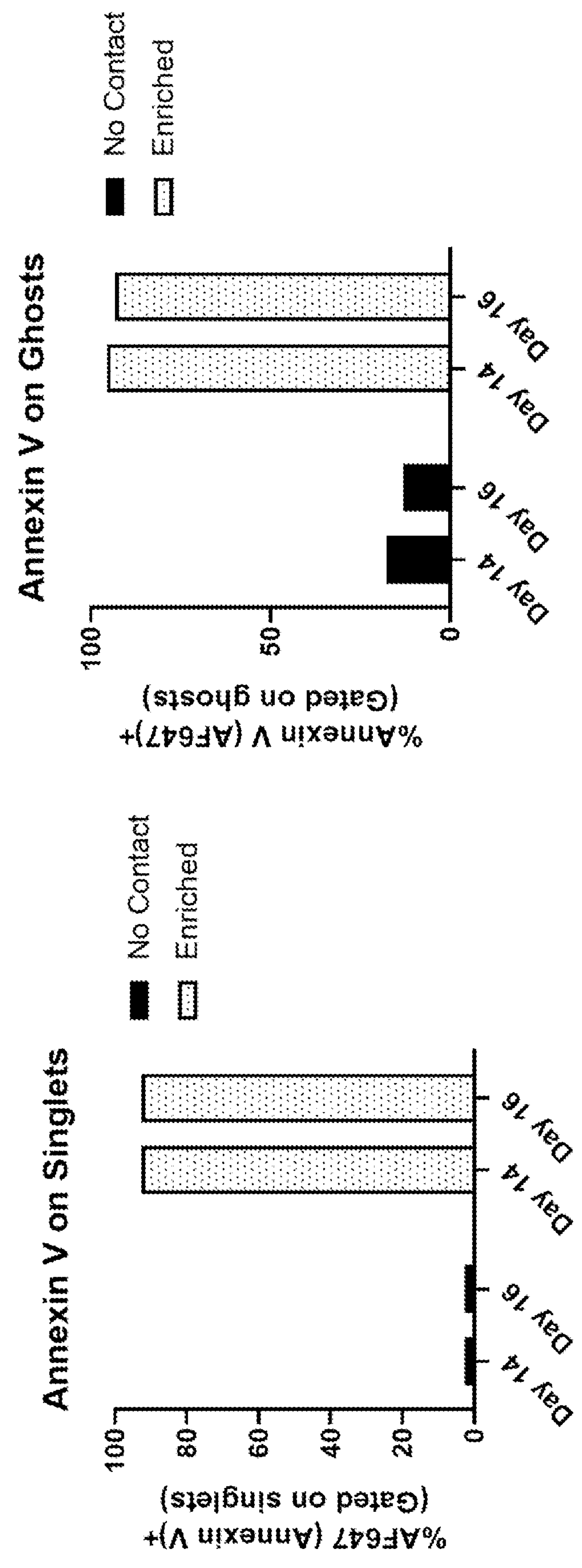
FIG. 3F shows the population of enriched ACs (singlet population-left; ghost population-right) which exhibit cell surface phosphatidylserine (Annexin V staining).

As shown in FIG. 3D, ghost populations subsequent to squeeze-processing ranged from 64-73% after RBCs were squeeze-processed to generate ACs for Day 14 administration, and from 61-76% after RBCs were squeeze-processed to generate ACs for Day 16 administration, showing consistent generation of ghost populations after RBCs were squeeze-processed. Also, as shown in FIG. 3E, yield of ACs generated from squeeze processing were comparable in ACs generated for Day 14 administration (18%) and Day 16 administration (29%). In addition, a high proportion of the squeeze-processed RBCs exhibited cell surface phosphatidylserine, as assayed by Annexin V staining (93% out of enriched ACs; or 96% within ghost populations of enriched ACs; FIG. 3F left and right panel, respectively).

Figure 3G:
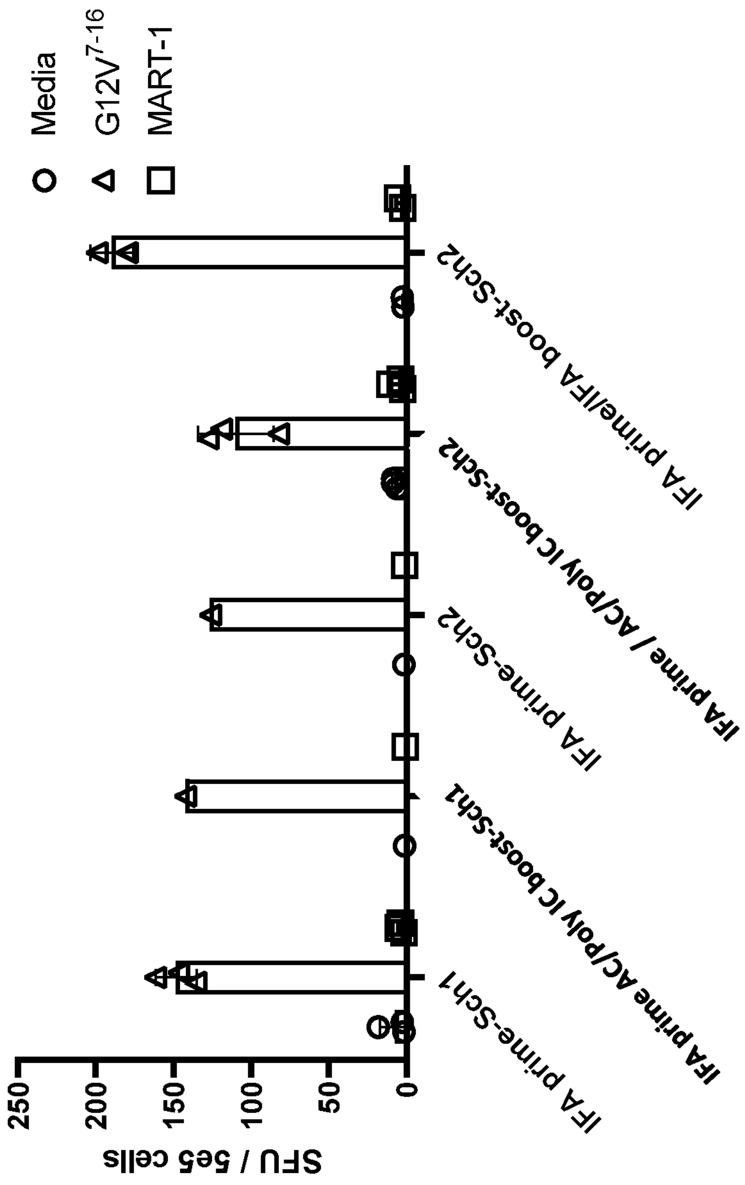
FIG. 3G shows the spot-forming unit (SFU) per 5e5 cells in IFN-γ ELISPOT assays of harvested murine cells at takedown subsequent to spiking with the indicated protein (G12V$^{7-16}$ or MART-1) or control (media).
Figure 3H:
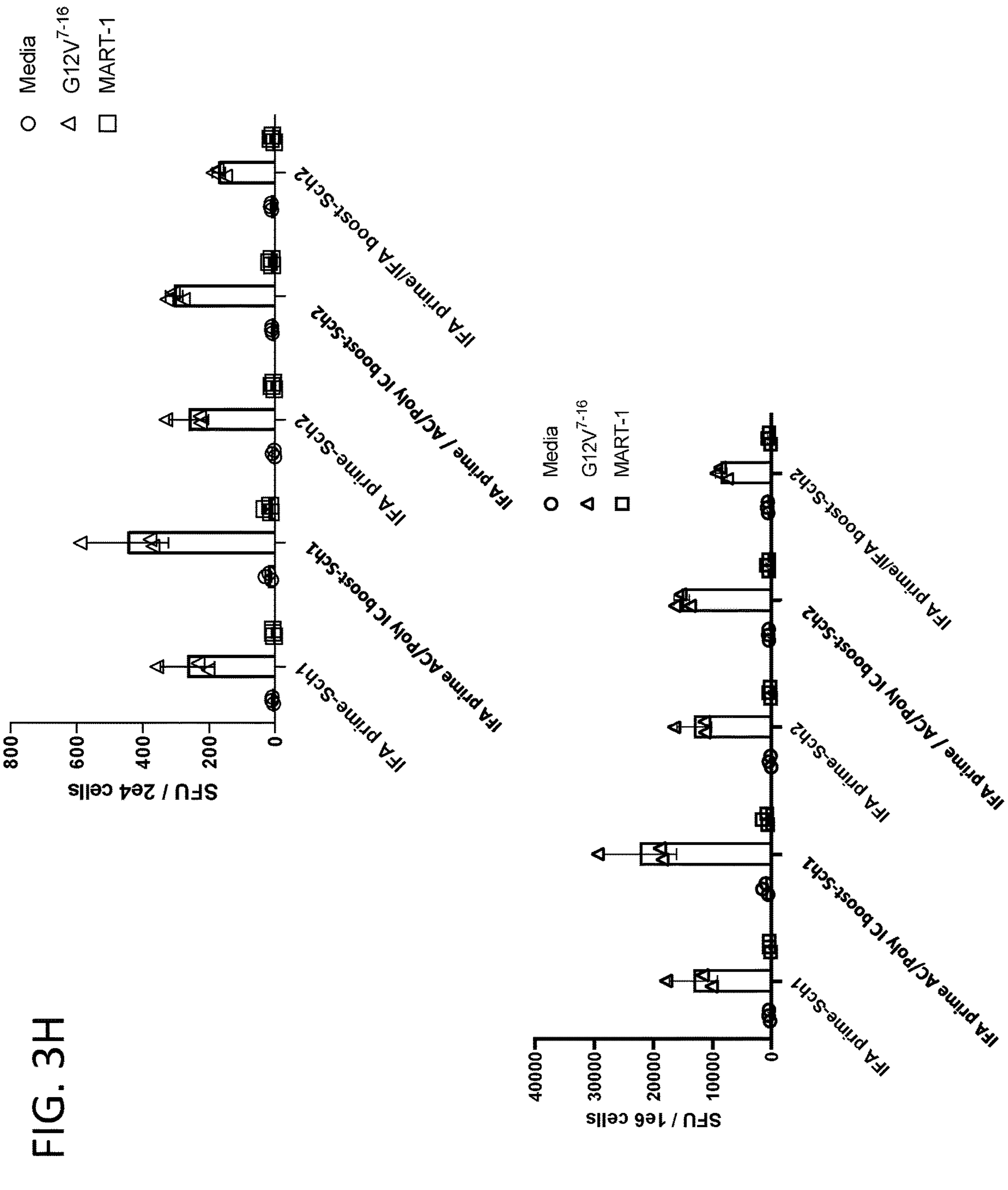
FIG. 3H shows the SFU per 2e4 cells (upper panel) or SFU per 1e6 cells (lower panel) in IFN-γ ELISPOT assays of harvested murine cells subsequent to spiking with the indicated protein (G12V$^{7-16}$ or MART-1) or control (media), and 6 days of in vitro culture.

As shown in FIG. 3G, use of KRas/HBV/IFA as a boosting vaccination (IFA boost) resulted only in a modestly increased antigen-specific T cell response, as assayed by IFN-γ ELISPOT assay at the end of the dosing schedule (take-down). As shown in FIG. 3H, with 6 days of in vitro expansion after K-Ras G12V peptide spike, use of AC$^{G12V1-16}$/polyI:C as a boosting vaccination resulted in comparable or modestly increased antigen-specific T cell response, as assayed by IFN-γ ELISPOT assay.

Example 12

To determine the efficacy of co-administration of antigen carriers (ACs) and adjuvant in eliciting an antigen specific responder T cells in vivo and to optimize dosing schedules, murine RBCs were squeeze-processed with G12V antigen, and co-administered with poly I:C to HLA-A*11 transgenic mice in various dosing schedules. The activity of specific responder cells harvested from the immunized mice (e.g. IFN-γ expression and/or secretion) after stimulation with G12V antigen was measured via ELISPOT.

Methods

Murine donor RBCs were isolated. The RBCs were squeeze-processed at room temperature through a microfluidic chip (2.2 μm width, 10 μm length, 70 μm depth) at a density of $1\times10^9$ RBCs/mL at 50 psi or 70 psi in the presence of 200 μM synthetic long peptide (G12V$^{1-16}$ SLP) in RPMI. Unprocessed RBCs were also used as control (no contact). Following squeeze-processing, the processed RBCs were rested at room temperature for 40 minutes, then centrifuged (at 8000×g) and washed in PBS before resuspension in PBS or CTL medium (supplemented with 1% glutamine). The squeeze-processed RBCs comprising the G12V$^{1-16}$ SLP (AC$^{G12V1-16}$) were enriched (e.g. through physical separation) for the ghost population within the ACs (enriched). Control RBCs (no contact) and the AC populations (pre-enriched ACs, enriched ACs) were analyzed for cell surface phosphatidylserine (Annexin V staining).

Figure 4A:
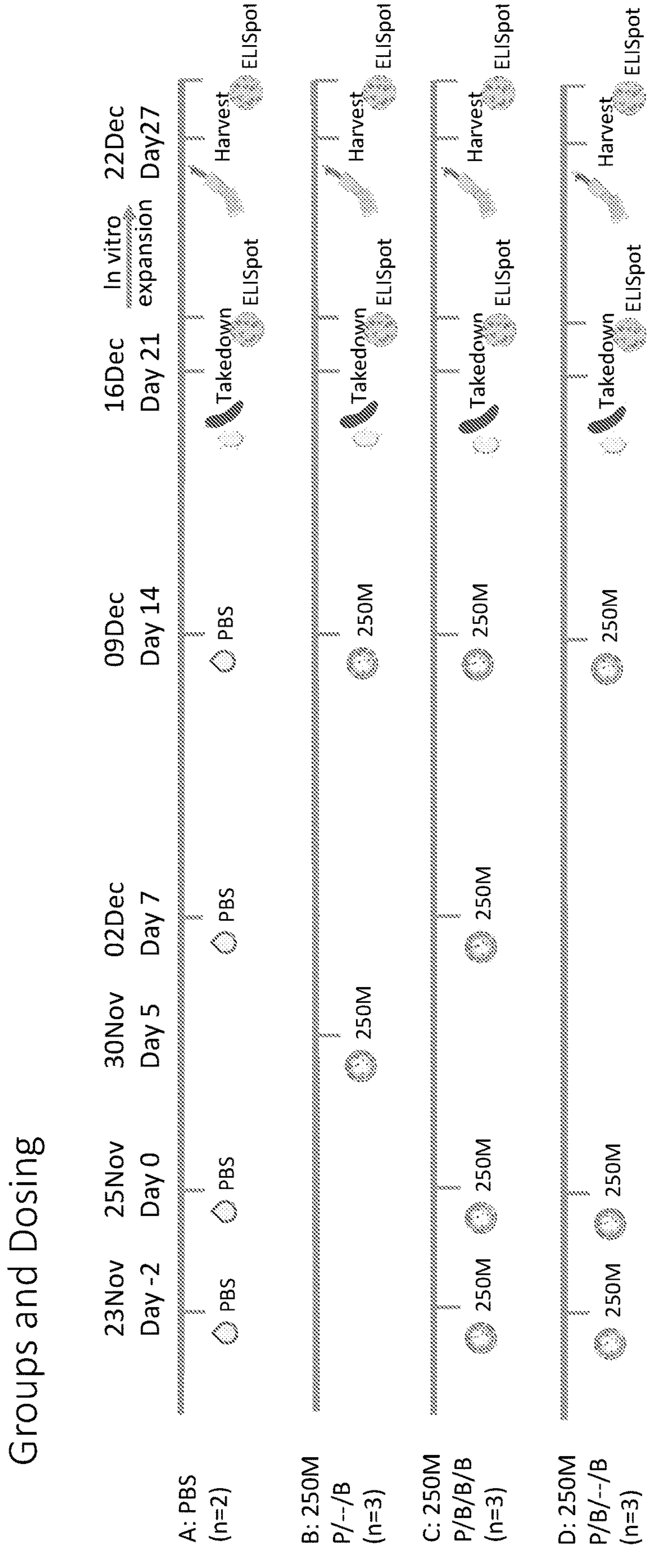
FIG. 4A is a schematic of the dosing groups and schedules showing administrations of AC$^{G12V1-16}$/poly I:C in a murine model, and the subsequent tissue harvests and assays for immune activity (IFN-γ ELISPOT).

Subsequently, ACs$^{G12V1-16}$ (250 million ACs)+1 mg/mL Poly I:C, or PBS (control) were retro-orbitally (RO) administered to HLA-A*11 transgenic mice according to the dosing schedule shown in FIG. 4A:

Group A: PBS (control) on Day −2, Day 0, Day 7 and Day 14.

Group B: 250M ACs$^{G12V1-16}$+poly I:C administered on Day 5 and Day 14 (P/-/B)

Group C: 250M ACs$^{G12V1-16}$+poly I:C administered on Day −2, Day 0, Day 7 and Day 14 (P/B/B/B)

Group D: 250M ACs$^{G12V1-16}$ administered on Day −2, Day 0, and Day 14 (P/B/-/B)

At the end of the described dosing schedule (take-down), the spleen and/or draining lymph nodes were harvested from the treated or control mice, wherein the splenocytes or lymph-node derived cells were treated by spiking with 1 μM G12V$^{7-16}$ K-Ras peptide or a non-relevant control peptide (MART1), and either subjected to IFN-γ ELISPOT assay immediately (take-down) or subjected to IFN-γ ELISPOT assay after 6 days of in vitro expansion, as shown in FIG. 3C.

Results

Figure 4B:
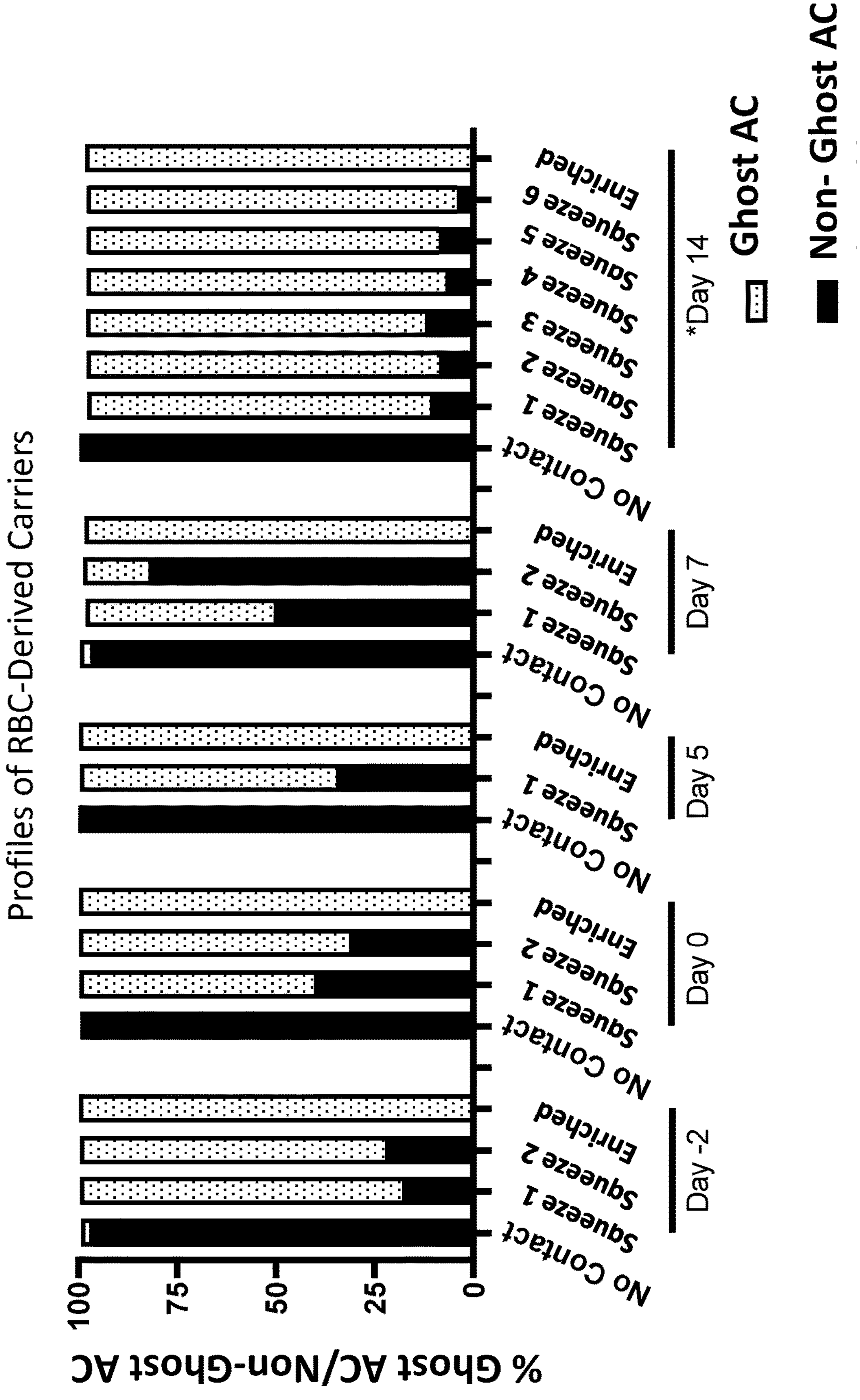
FIG. 4B shows the percentage of ghost populations within the indicated red blood cell-derived carriers (antigen carriers) subsequent to squeeze-processing, or subsequent to squeeze-processing and enrichment.
Figure 4C:
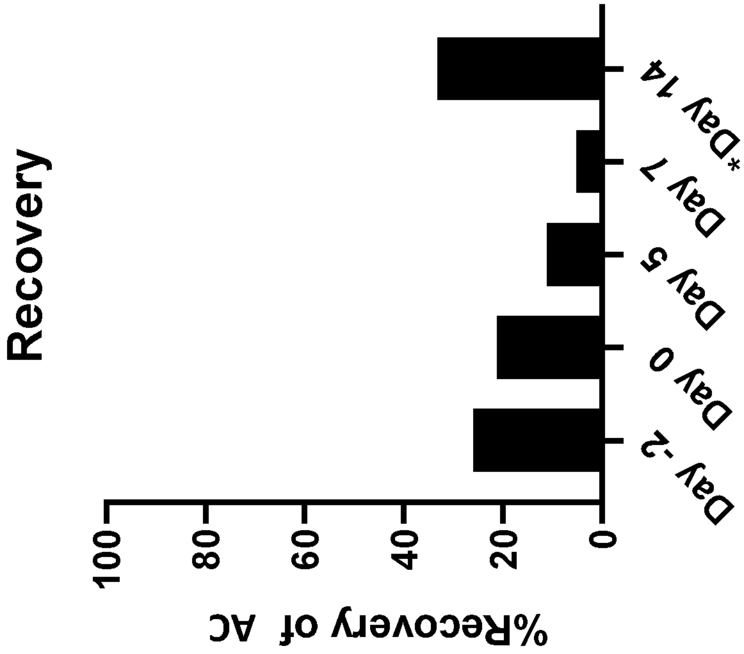
FIG. 4C shows the percentage of recovery of antigen carriers subsequent to squeeze-processing of RBCs.
Figure 4D:
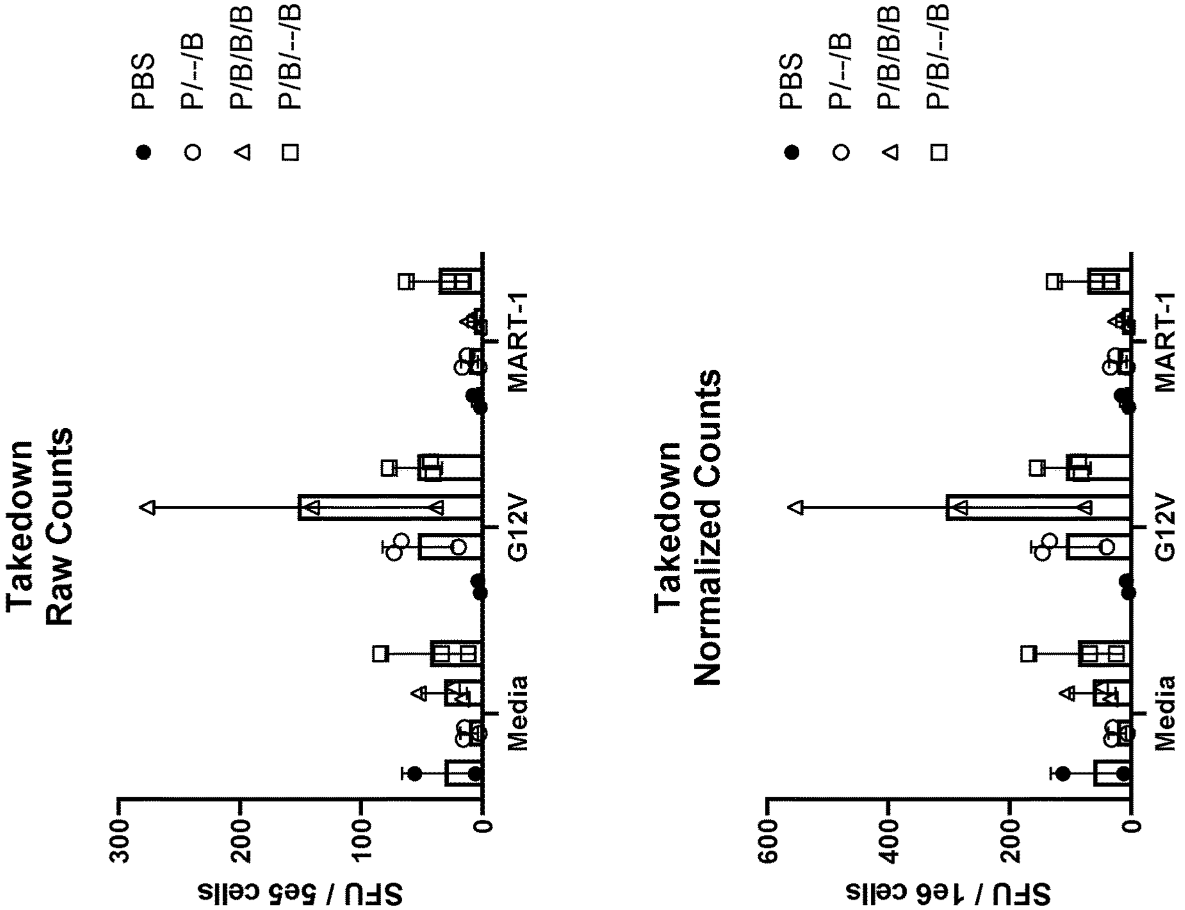
FIG. 4D shows the SFU per 5e5 cells (upper panel) or SFU per 1e6 cells (lower panel) in IFN-γ ELISPOT assays of harvested murine cells at takedown subsequent to spiking with the indicated protein (G12V$^{7-16}$ or MART-1) or control (media).
Figure 4E:
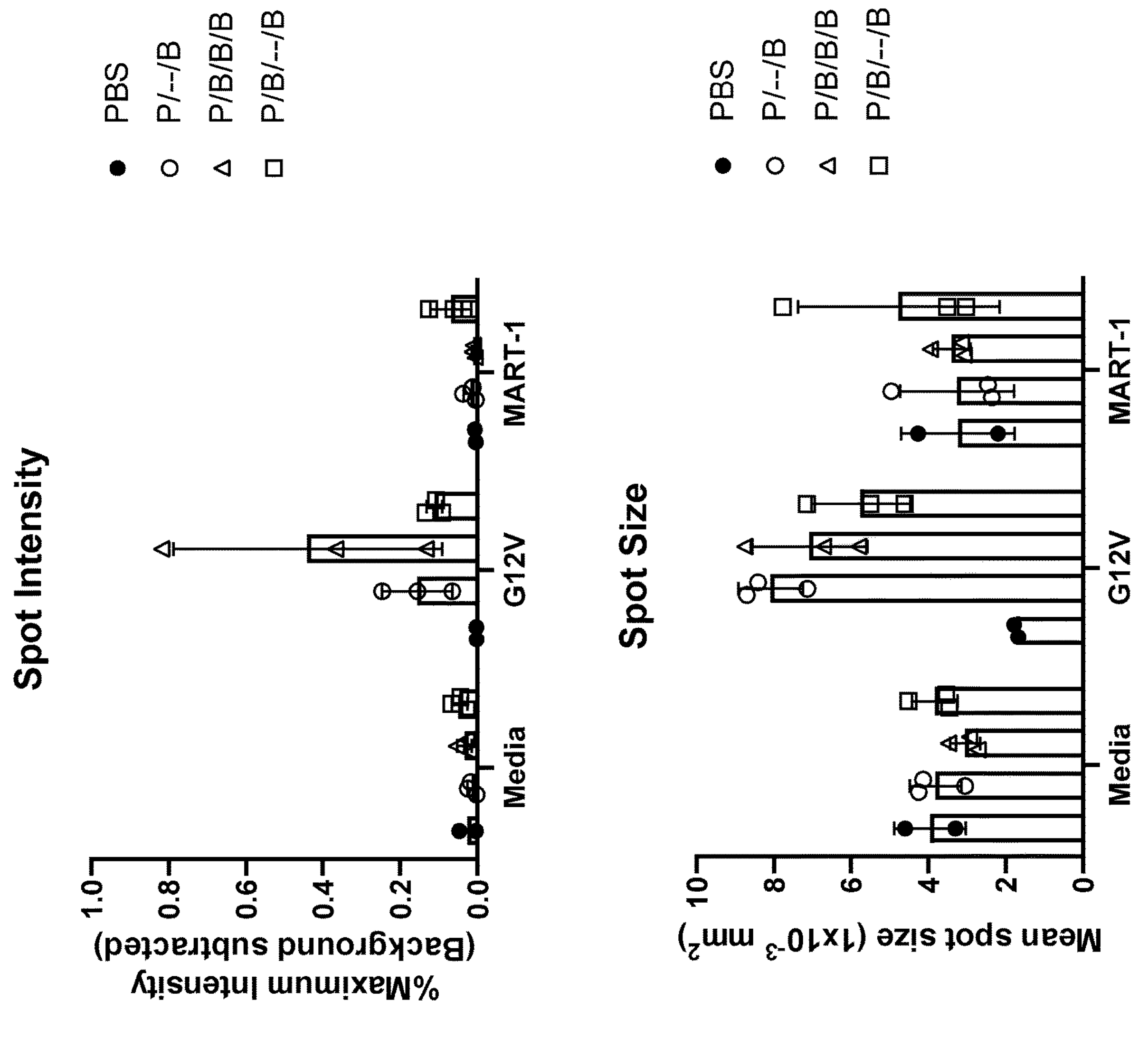
FIG. 4E shows the spot intensity (upper panel) and spot size (lower panel) in IFN-γ ELISPOT assays of harvested murine cells at takedown subsequent to spiking with the indicated protein (G12V$^{7-16}$ or MART-1) or control (media).
Figure 4F:
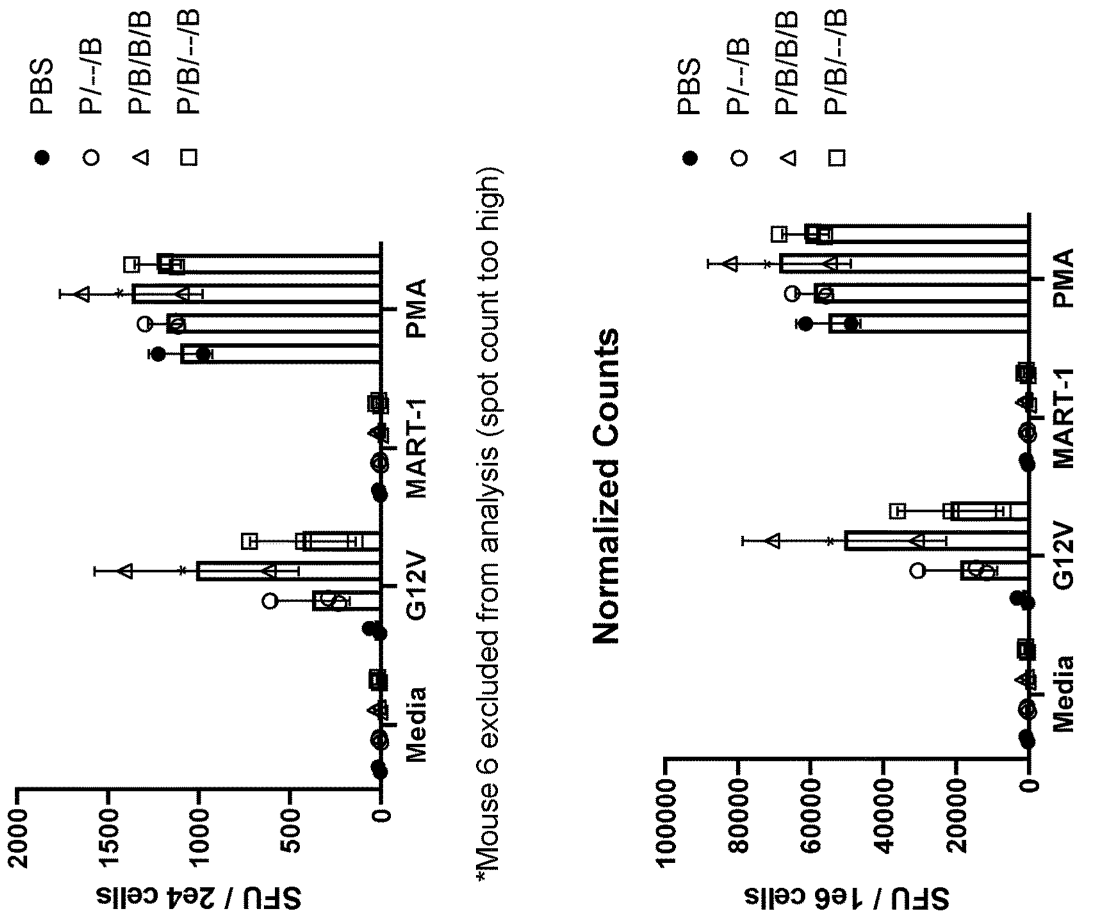
FIG. 4F shows the SFU per 2e4 cells (upper panel) or SFU per 1e6 cells (lower panel) in IFN-γ ELISPOT assays of harvested murine cells subsequent to spiking with the indicated protein (G12V$^{7-16}$ or MART-1) or control (media), and 6 days of in vitro culture.
Figure 4G:
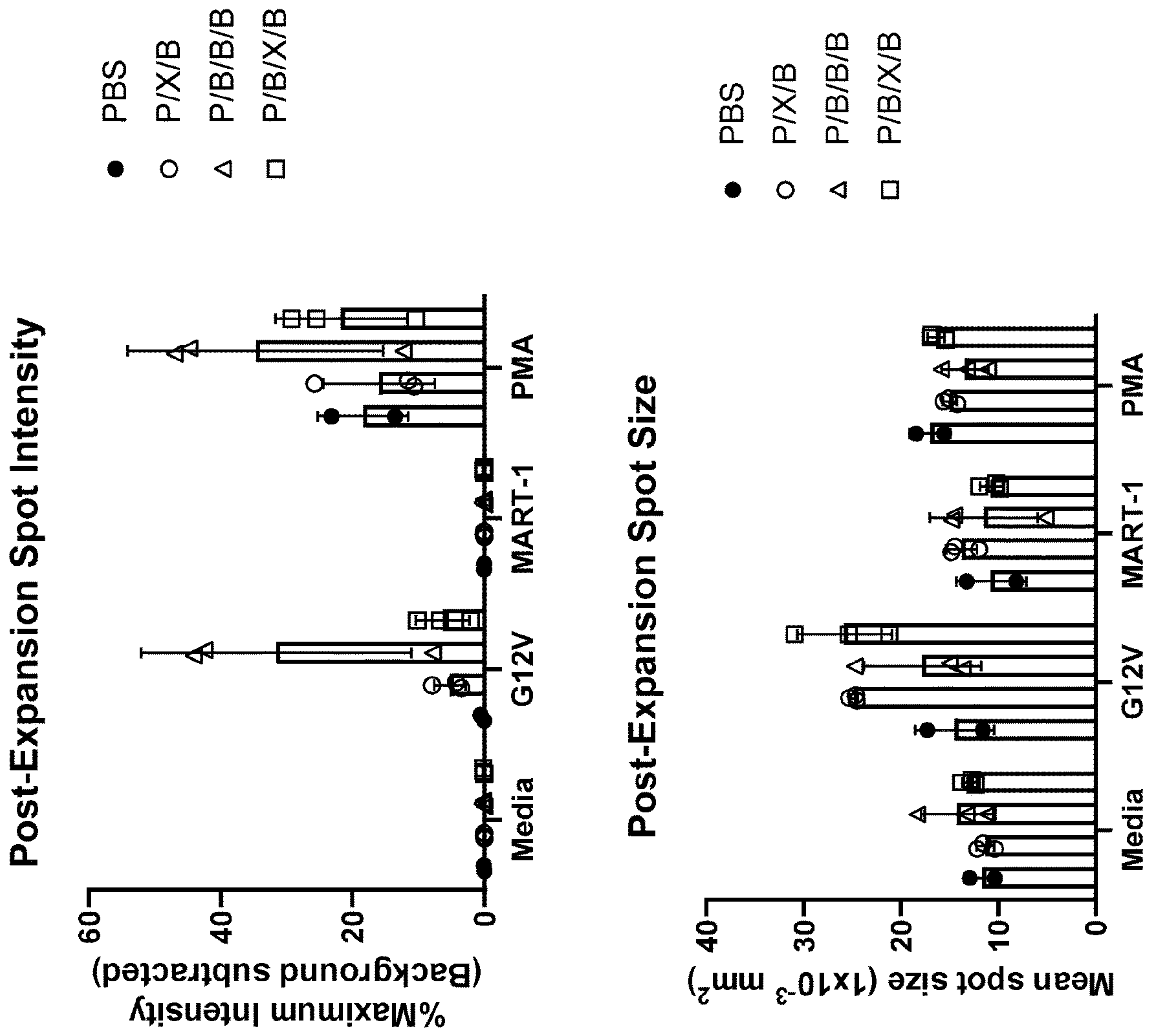
FIG. 4G shows the spot intensity (upper panel) and spot size (lower panel) in IFN-γ ELISPOT assays of harvested murine cells subsequent to spiking with the indicated protein (G12V$^{7-16}$ or MART-1) or control (media), and 6 days of in vitro culture.

As shown in FIG. 4B, ghost populations subsequent to squeeze-processing ranged from 17%-68% after RBCs were squeeze-processed to generate ACs for Day −2, Day 0 and Day 7 administrations (squeeze-processed at 50 psi), and about 86% to 94% after RBCs were squeeze-processed to generate ACs for Day 14 administration (squeeze-processed at 70 psi). Also, as shown in FIG. 4C, recovery yield of ACs generated from squeeze processing were comparable in ACs generated for Day −2, Day 0, Day 5 and Day 7 administrations (5%-26%, squeeze-processed at 50 psi), whereas the recovery yield was higher for ACs generated for Day 16 administration (33%, squeeze-processed at 70 psi).

As shown in FIGS. 4D, 4E, 4F and 4G, administration of $AC^{G12V1\text{-}16}$/poly I:C resulted in increased antigen-specific T cell response, as assayed by IFN-γ ELISPOT assay. In particular, $AC^{G12V1\text{-}16}$/poly I:C administered according to P/B/B/B schedule resulted in strongly elicited antigen-specific T cell response, as assayed by IFN-γ ELISPOT assay both at takedown (mean ~300 SFU/1e6 cells, FIG. 4D) and after in vitro expansion (mean ~51000 SFU/1e6 cells, FIG. 4F). In contrast, $AC^{G12V1\text{-}16}$/poly I:C administered according to P/--/B schedule and P/B/--/B schedule resulted in modestly activated response at takedown and after in vitro expansion (~19000-22000 SFU/1e6 cells).

Example 13

To determine the efficacy of activating antigen carriers (AACs) comprising antigen and adjuvant versus a co-administration of antigen carriers (ACs) with adjuvant in eliciting an antigen specific responder T cells in vivo, murine RBCs were squeeze-processed with G12V antigen with or without poly I:C, and administered (with or without co-injection of poly I:C) to HLA-A*11 transgenic mice in various dosing schedules. The activity of specific responder cells harvested from the immunized mice (e.g. IFN-γ expression and/or secretion) after stimulation with G12V antigen was measured via ELISPOT.

Methods

Murine donor RBCs were isolated. The RBCs were squeeze-processed at room temperature through a microfluidic chip (2.2 μm width, 10 μm length, 70 μm depth) at a density of $2\times10^9$ RBCs/mL at 70 psi in the presence of (1) 200 μM synthetic long peptide ($G12V^{1\text{-}16}$ SLP), or (2) 200 μM $G12V^{1\text{-}16}$ SLP and 1 mg/mL Poly I:C. Unprocessed RBCs were also used as control (no contact). Following squeeze-processing, the processed RBCs were rested at room temperature for 40 minutes, then centrifuged (at 8000× g) and washed in PBS before resuspension in either PBS or CTL medium (supplemented with 1% glutamine). The squeeze-processed RBCs comprising the $G12V^{1\text{-}16}$ SLP ($AC^{G12V1\text{-}16}$) or comprising $G12V^{1\text{-}16}$ SLP and poly I:C ($AAC^{G12V1\text{-}16}$) were enriched (e.g. through physical separation) for the ghost population within the ACs or AACs (enriched). Control RBCs (no contact) and the AC or AAC populations (pre-enriched ACs or AACs, enriched ACs or AACs) were analyzed for cell surface phosphatidylserine (Annexin V staining).

Figure 5A:
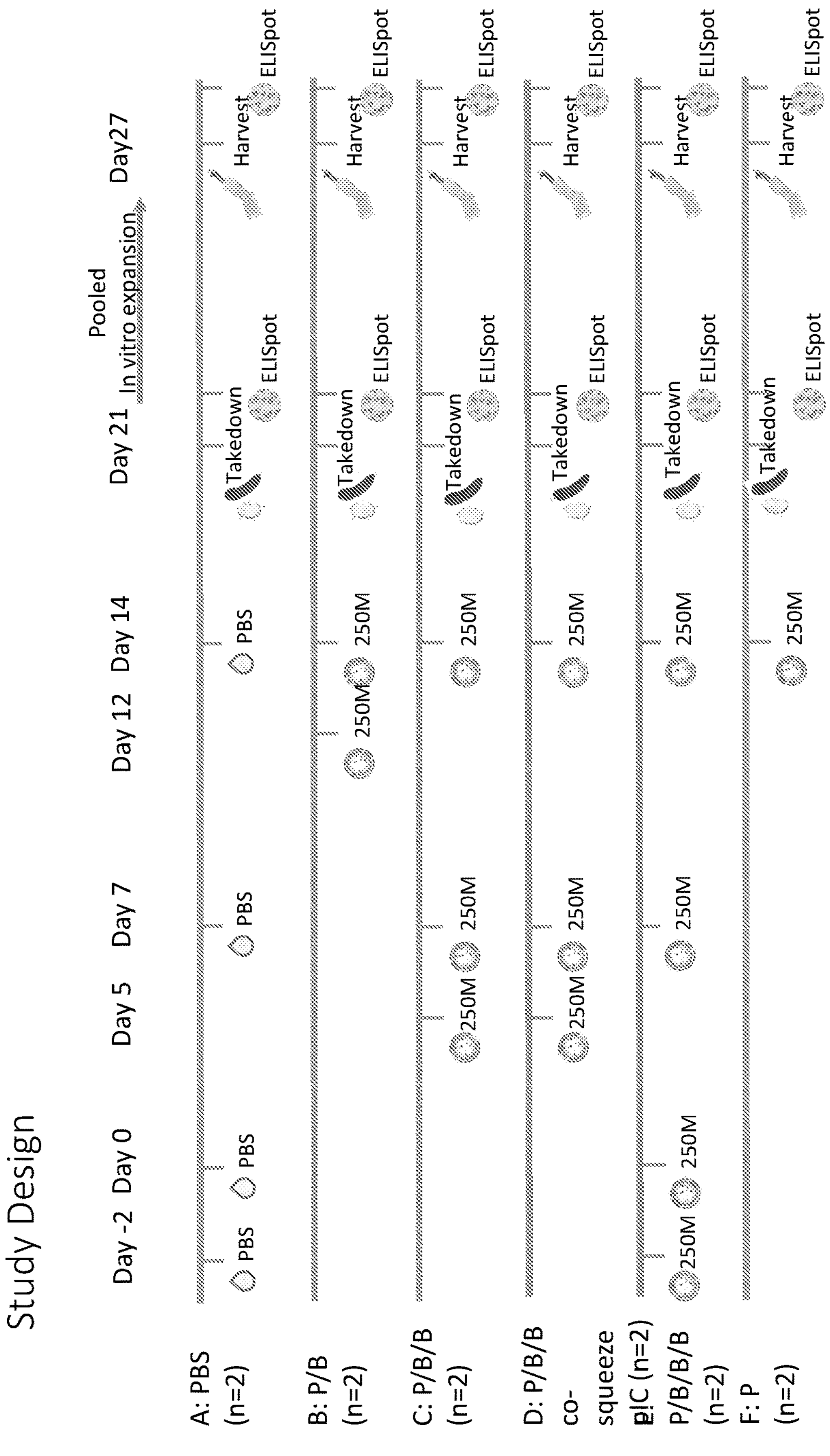
FIG. 5A is a schematic of the dosing groups and schedules showing administrations of AC$^{G12V1-16}$/poly I:C or AAC$^{G12V1-16}$ (activating antigen carriers comprising KRas-G12V$^{1-16}$+polyI:C within) in a murine model, and the subsequent tissue harvests and assays for immune activity (IFN-γ ELISPOT).

Subsequently, co-administration of $ACs^{G12V1\text{-}16}$ (250 million ACs) and 1 mg/mL Poly I:C; or administration of $AAC^{G12V1\text{-}16}$ (250 million AACs), or PBS (control) were retro-orbitally (RO) administered to HLA-A*11 transgenic mice according to the dosing schedule shown in FIG. 5A:

Group A: PBS (control) on Day −2, Day 0, Day 7 and Day 14.

Group B: 250M $ACs^{G12V1\text{-}16}$+poly I:C administered on Day 12 and Day 14 (P/-/B)

Group C: 250M $ACs^{G12V1\text{-}16}$+poly I:C administered on Day 5, Day 7 and Day 14 (P/B/B)

Group D: 250M $AAC^{G12V1\text{-}16}$ (generated by co-squeezing $G12V^{1\text{-}16}$ and poly I:C) administered on Day 5, Day 7, and Day 14 (P/B/B co-squeeze pIC)

Group E: 250M $ACs^{G12V1\text{-}16}$+poly I:C administered on Day −2, Day 0, Day 7 and Day 14 (P/B/B)

Group F: 250M $ACs^{G12V1\text{-}16}$+poly I:C administered on Day 14 (P)

At the end of the described dosing schedule (take-down), the spleen and/or draining lymph nodes were harvested from the treated or control mice, wherein the splenocytes or lymph-node derived cells were treated with spiking of 1 μM $G12V^{7\text{-}16}$ K-Ras Peptide or a non-relevant control protein (MART1), and either subjected to IFN-γELISPOT assay immediately (take-down) or subjected to IFN-γ ELISPOT assay after 6 days of in vitro expansion, as previously shown in FIG. 3C.

Results

Figure 5B:
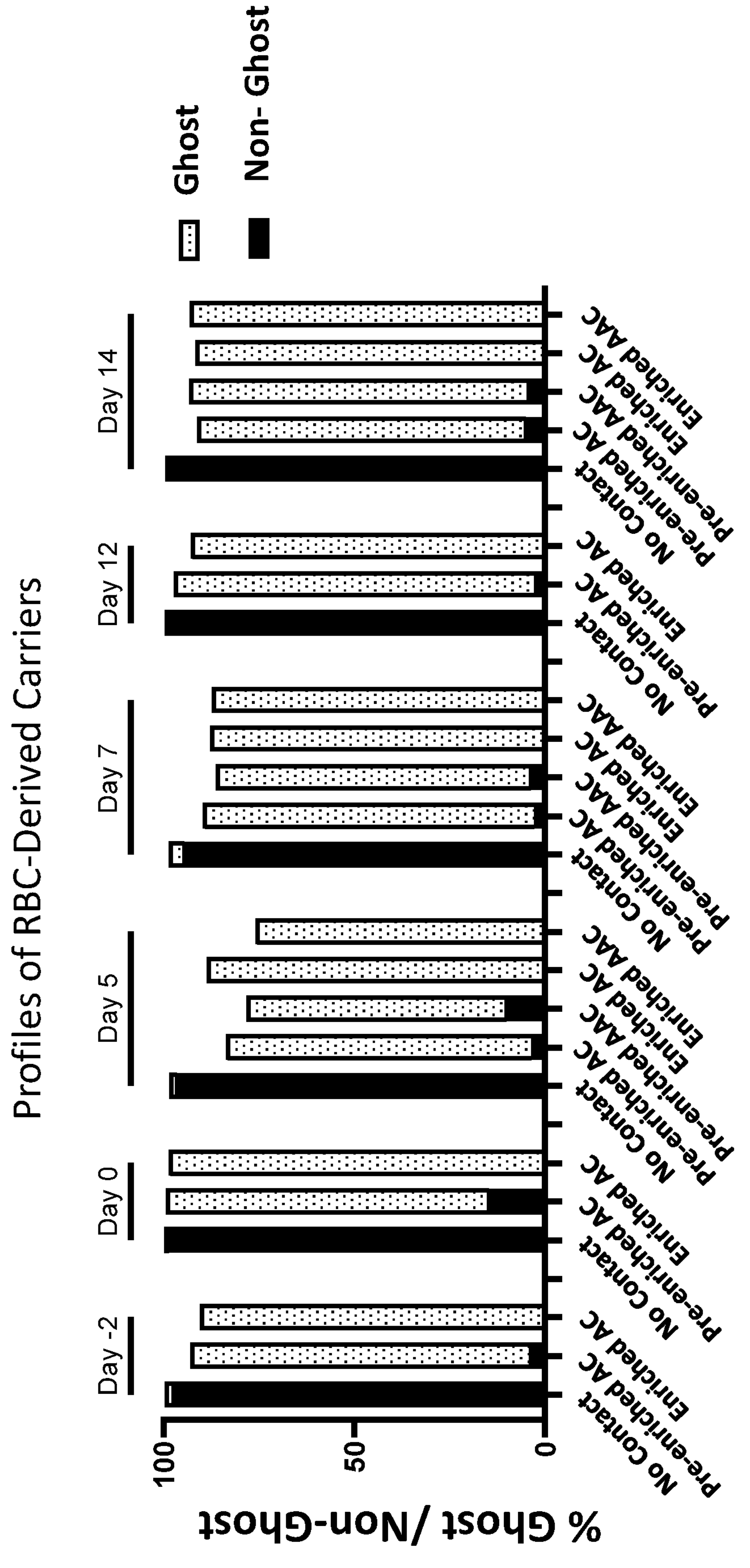
FIG. 5B shows the percentage of ghost populations within the indicated red blood cell-derived carriers (ACs or AACs) subsequent to squeeze-processing, or subsequent to squeeze-processing and enrichment. FIG.
Figure 5C:
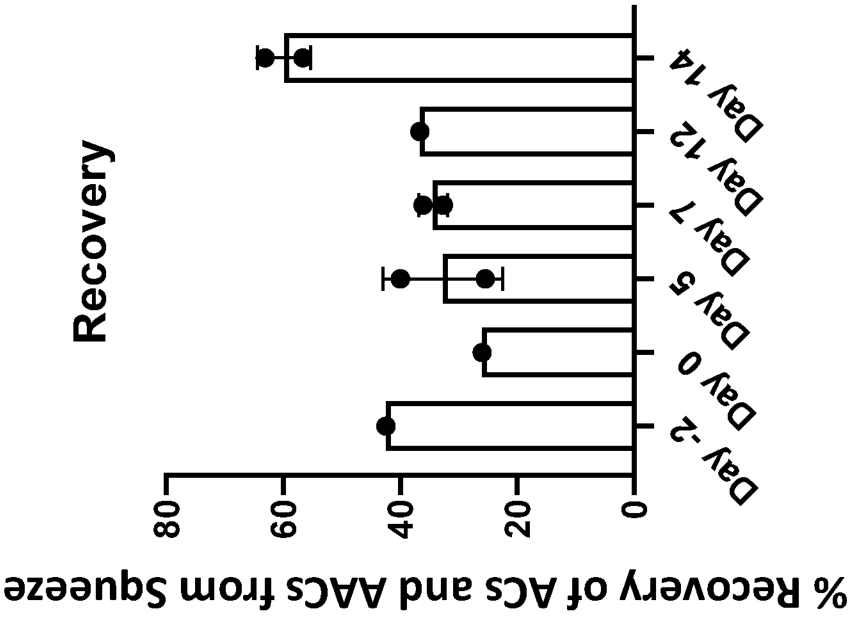
FIG. 5D shows the SFU per 1e6 cells in IFN-γ ELISPOT assays of harvested murine cells at takedown subsequent to spiking with the indicated protein (G12$V^{7-16}$ or MART-1) or control (media).
FIG. 5E shows the SFU per 1e6 cells in IFN-γ ELISPOT assays of harvested murine cells subsequent to spiking with the indicated protein (G12$V^{7-16}$ or MART-1) or control (media), and 6 days of in vitro culture.

As shown in FIG. 5B, ghost populations subsequent to squeeze-processing ranged from 68%-94% after RBCs were squeeze-processed to generate ACs or AACs for Day −2, Day 0, Day 5, Day 7, Day 12, and Day 14 administration, showing consistent generation of high proportion of ghost populations after RBCs were squeeze-processed. Also, as shown in FIG. 5C, recovery from squeeze processing were comparable in ACs and AACs generated for Day −2, Day 0, Day 5, Day 7, Day 12 administrations (about 20%-40%, squeezing at 50 psi) and further elevated for ACs and AACs generated for Day 14 administration (about 60%, squeezing at 70 psi).

Figure 5D:
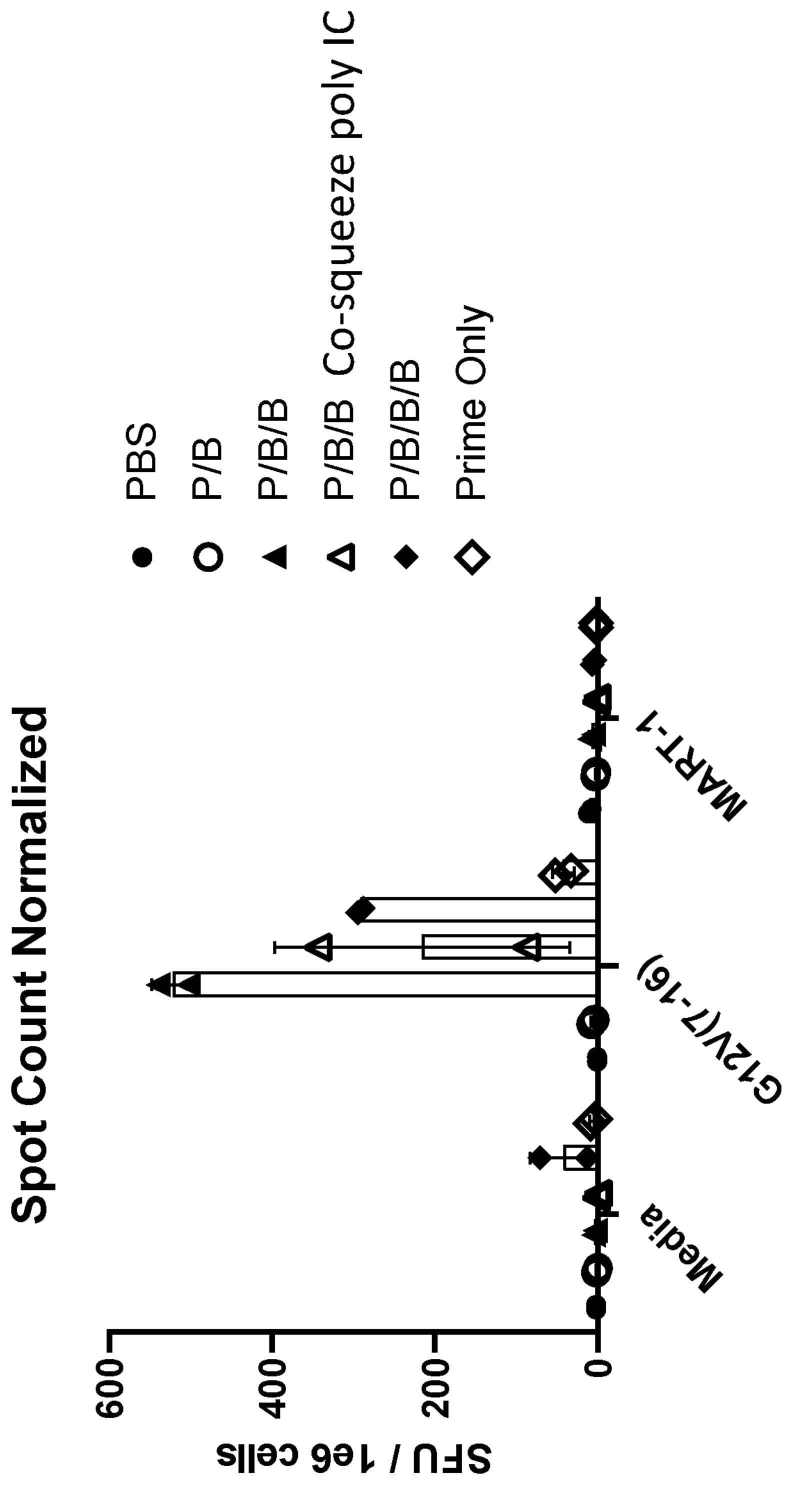
Figure 5E:
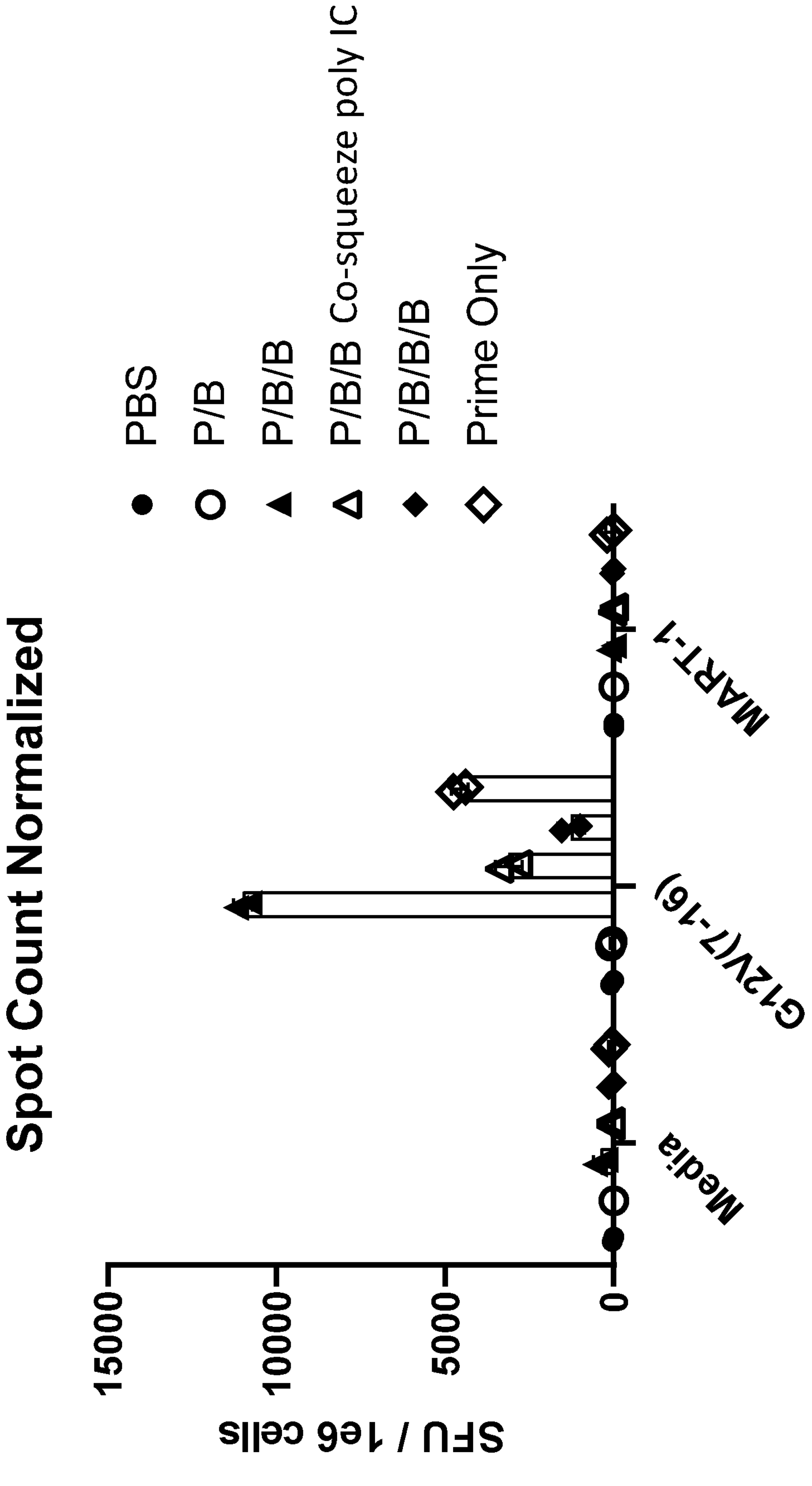

As shown in FIGS. 5D and 5E, P/B/B group (250M $ACs^{G12V1\text{-}16}$+poly I:C co-administered on Day 5, Day 7 and Day 14) showed the highest ELISPOT spot counts of all groups both at takedown and after in vitro expansion, with ~2-fold and ~3.5-fold higher counts than P/B/B co-squeeze pIC (250M $AACs^{G12V1\text{-}16}$ administered on Day 5, Day 7, and Day 14) at takedown and post-expansion, respectively. For prime only group P (250M $ACs^{G12V1\text{-}16}$+poly I:C co-administered on Day 14), significant responses were only observed from the Prime Only group after in vitro expansion, as assayed by ELISPOT spot counts.

Example 14

To determine the efficacy of activating antigen carriers (AACs) comprising both antigen and adjuvant in eliciting an antigen specific responder T cells in vivo and to optimize the dosing schedules, murine RBCs were squeeze-processed with G12V antigen and poly I:C, and administered to HLA-A*11 transgenic mice in various dosing schedules. The activity of specific responder cells harvested from the immunized mice (e.g. IFN-γ expression and/or secretion) after stimulation with G12V antigen was measured via ELISPOT.

Methods

Murine donor RBCs were isolated. The RBCs were squeeze-processed at room temperature through a microfluidic chip (2.2 μm width, 10 μm length, 70 μm depth) at a density of $2\times10^9$ RBCs/mL at 70 psi in the presence of 200 μM synthetic long peptide ($G12V^{1\text{-}16}$ SLP) and Dalton Poly I:C in RPMI. Unprocessed RBCs were also used as control (no contact). Following squeeze-processing, the processed RBCs were rested at room temperature for 1 hour, then centrifuged (at 8000×g) and washed in PBS before resuspension in PBS or CTL medium (supplemented with 1% glutamine). The squeeze-processed RBCs comprising $G12V^{1-16}$ SLP and poly I:C ($AAC^{G12V1-16}$) were enriched (e.g., by physical separation) for the ghost population within the AACs (enriched). Control RBCs (no contact) and the AAC populations (pre-enriched AACs, enriched AACs) were analyzed for cell surface phosphatidylserine (Annexin V staining).

Figure 6A:
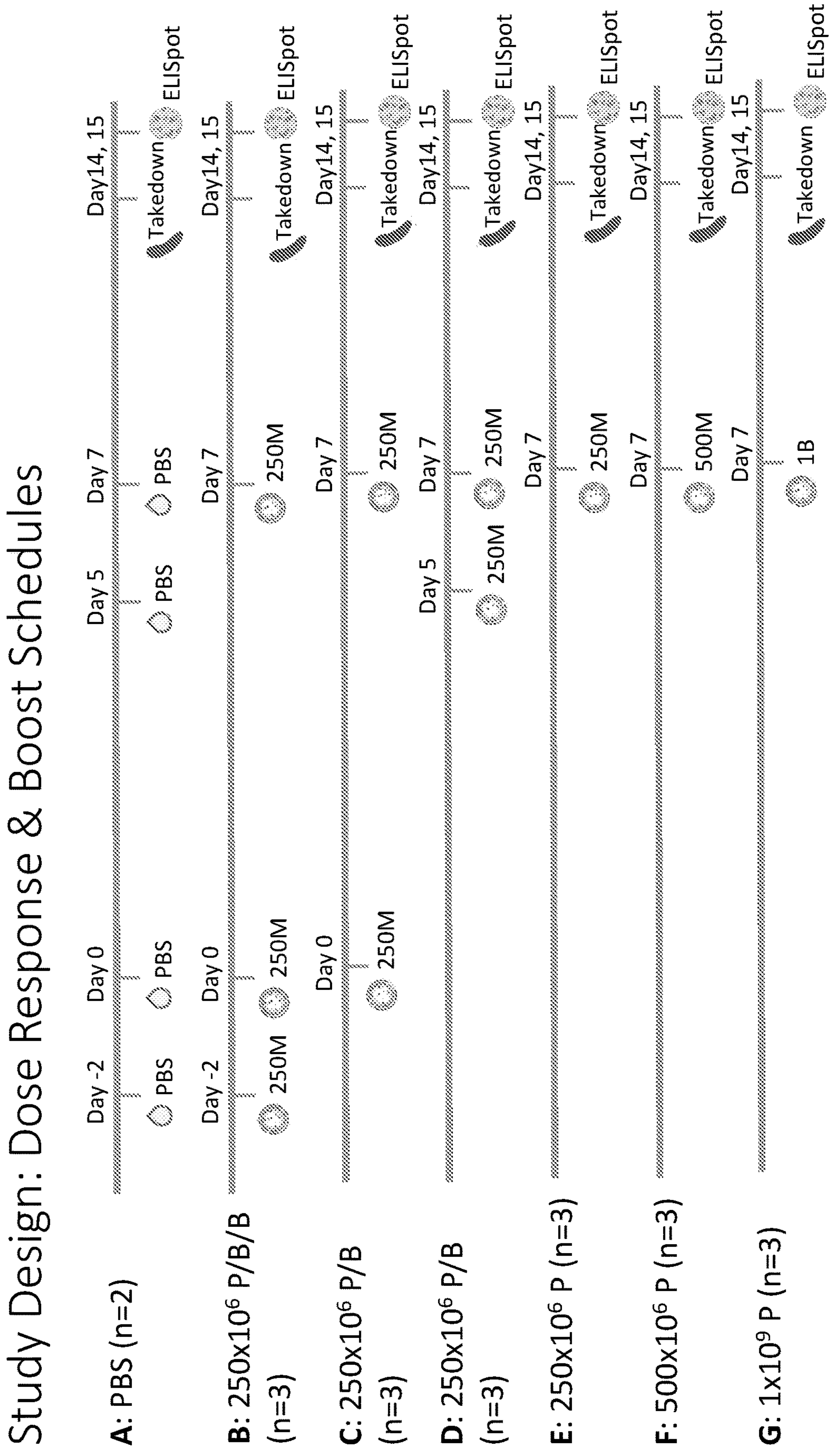
FIG. 6A is a schematic of the dosing groups and schedules showing administrations of $AAC^{G12V1-16}$ (activating antigen carriers comprising KRas-G12$V^{1-16}$+polyI:C within) in a murine model, and the subsequent tissue harvests and assays for immune activity (IFN-γ ELISPOT).

Subsequently, $AAC^{G12V1-16}$ (250 million, 500 million or 1 billion AACs), or PBS (control) were retro-orbitally (RO) administered to HLA-A*11 transgenic mice according to the dosing schedule shown in FIG. 6A:

Group A: PBS (control) on Day −2, Day 0, Day 5 and Day 7.

Group B: 250M $AACs^{G12V1-16}$ administered on Day-2, Day 0 and Day 7 (250M P/B/B)

Group C: 250M $AACs^{G12V1-16}$ administered on Day 0 and Day 7 (250M P/B Day 0,7)

Group D: 250M $AACs^{G12V1-16}$ administered on Day 5, and Day 7 (250M P/B Day 5,7)

Group E: 250M $AACs^{G12V1-16}$ administered on Day 7 (250M P Day 7)

Group F: 500M $AACs^{G12V1-16}$ administered on Day 7 (500M P Day 7)

Group F: 1B $AACs^{G12V1-16}$ administered on Day 7 (1B P Day 7)

At the end of the described dosing schedule (take-down), the spleen and/or draining lymph nodes were harvested from the treated or control mice, wherein the splenocytes or lymph-node derived cells were treated with spiking of 1 μM $G12V^{7-16}$ K-Ras peptide or a non-relevant control protein (MART1), and subjected to IFN-γ ELISPOT assay (take-down).

Results

Figure 6B:
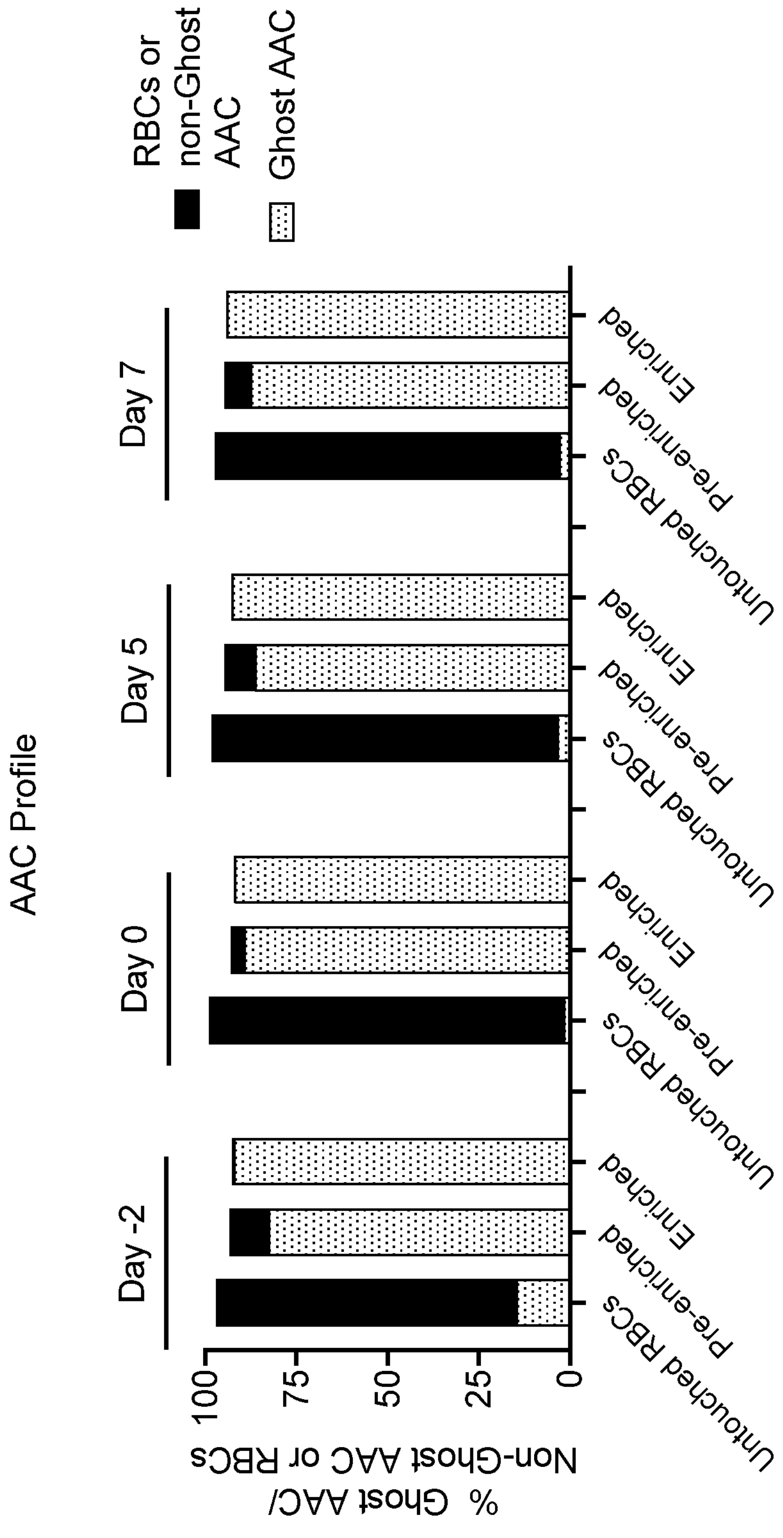
FIG. 6B shows the percentage of ghost populations within the indicated red blood cell-derived carriers (AACs) subsequent to squeeze-processing, or subsequent to squeeze-processing and enrichment.

FIG. 6B showed consistent generation of high proportion of ghost populations after RBCs were squeeze-processed at 70 psi for Day −2, Day 0, Day 5, and Day 7. Also, as shown in FIG. 6C, recovery of AACs generated from squeeze processing were comparable in AACs generated for Day −2, Day 0, Day 5, Day 7, Day 12 administrations (ranging from about 20%-40%).

Figure 6C:
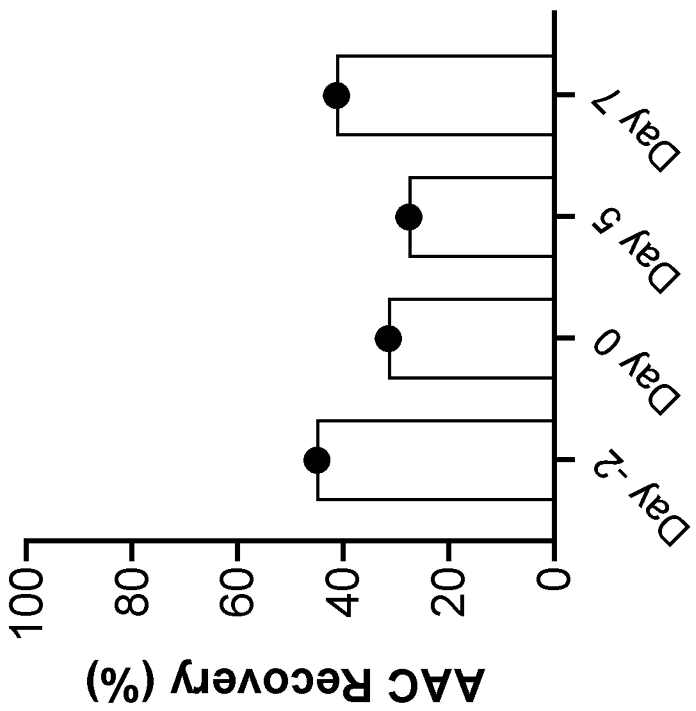
FIG. 6C shows the percentage of recovery of AACs subsequent to squeeze-processing of RBCs.
Figure 6D:
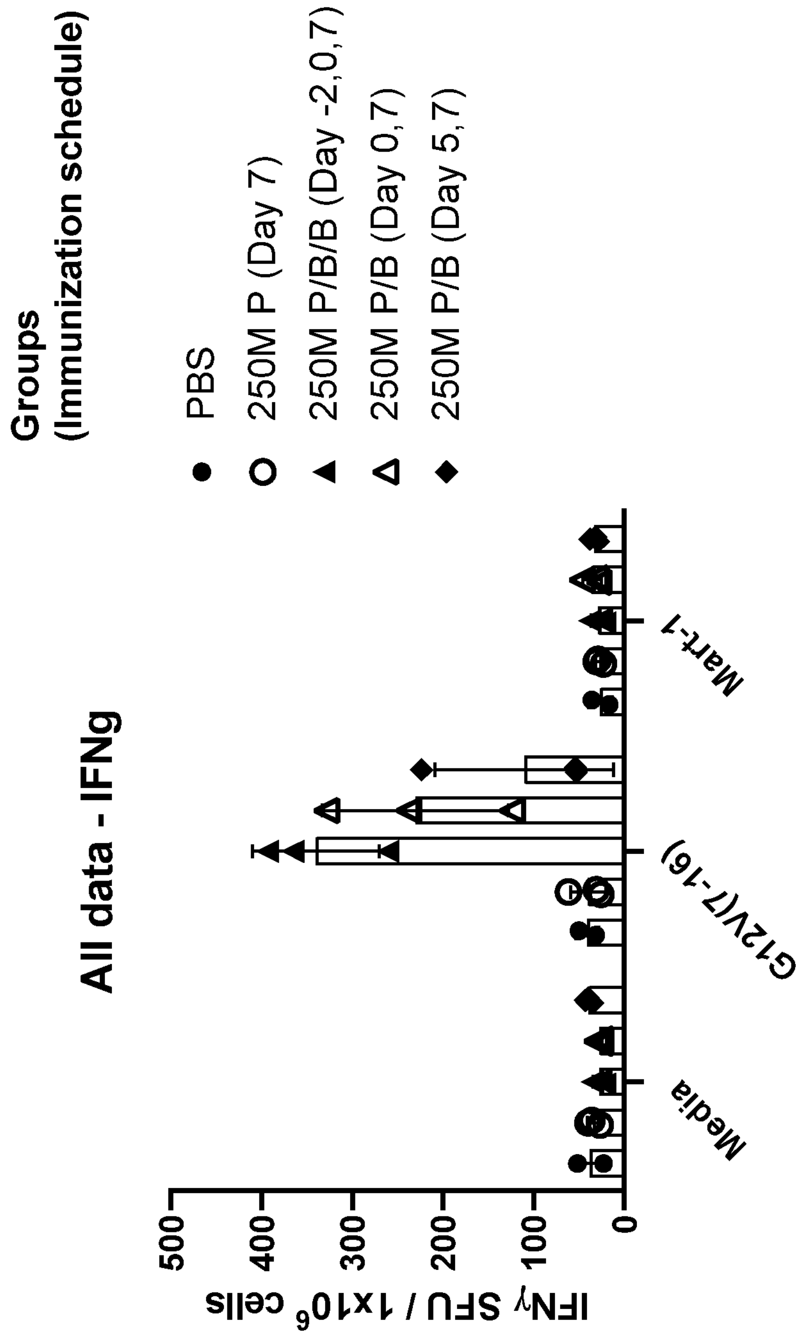
FIG. 6D shows the SFU per 1e6 cells in IFN-γ ELISPOT assays of harvested murine cells at takedown subsequent to spiking with the indicated protein (G12$V^{7-16}$ or MART-1) or control (media).
Figure 6E:
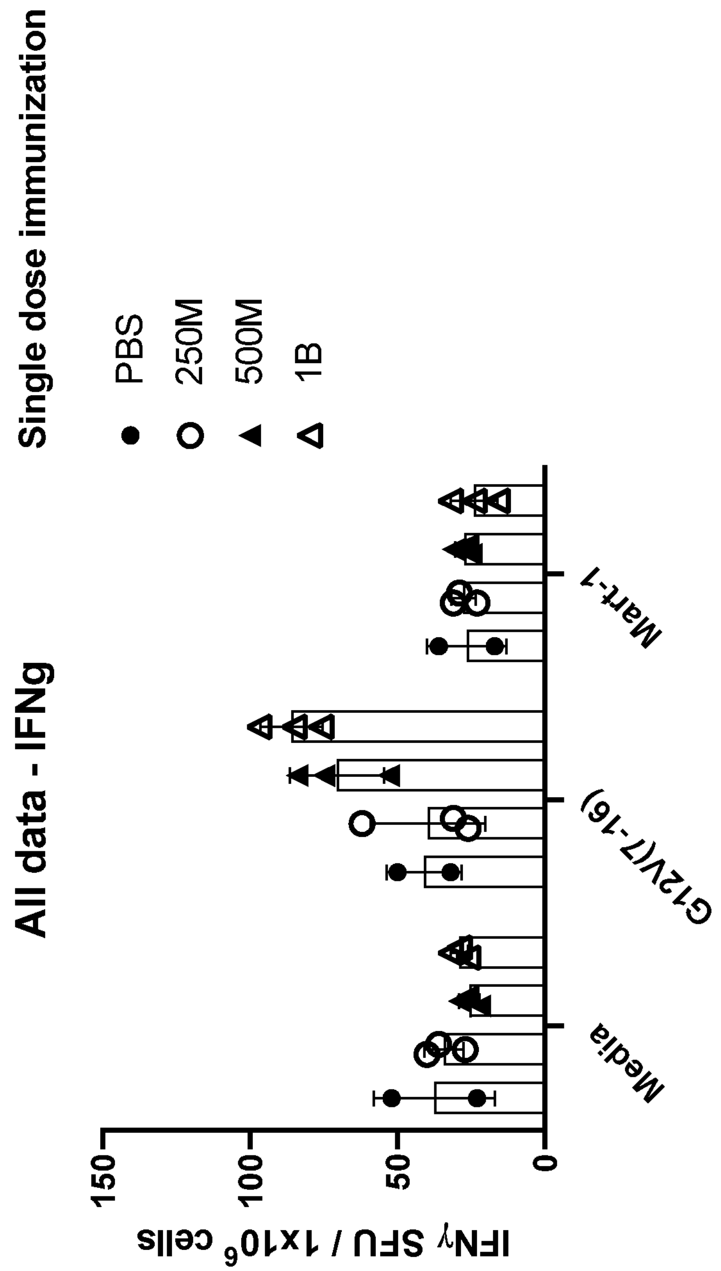
FIG. 6E shows the SFU per 1e6 cells in IFN-γ ELISPOT assays of harvested murine cells at takedown subsequent to spiking with the indicated protein (G12$V^{7-16}$ or MART-1) or control (media).

As shown in FIG. 6C, endogenous antigen-specific responses were observed at takedown when mice were administered with boosting schedules (P/B/B or P/B, having received 2 or 3 immunizations of 250M $AACs^{G12V1-16}$), as assayed by IFN-γ ELISPOT assay. As shown in FIG. 6D, while no response at takedown was observed for prime vaccination alone with 250M $AACs^{G12V1-16}$ (250M P Day 7), higher doses of prime vaccination alone (500M P Day 7 and 1B P Day 7) showed elicitation of small responses as compared to controls.

Sequence Listing

| SEQ ID NO | Sequence | Description |
|---|---|---|
| 1 | MTEYKLVVVGADGVGK | G12D(1-16) |
| 2 | TEYKLVVVGADGVGKSAL | G12D(2-19) |
| 3 | TEYKLVVVGADGVGKSALTIQ | G12D(2-22) |
| 4 | TEYKLVVVGADGVGKSALTIQLIQNHFV | G12D(2-29) |
| 5 | MTEYKLVVVGAVGVGK | G12V(1-16) |
| 6 | TEYKLVVVGAVGVGKSAL | G12V(2-19) |
| 7 | EYKLVVVGAVGVGKS | G12V(3-17) |
| 8 | EYKLVVVGAVGVGKSALTIQLIQNHFVD EYDPTIEDSYRK | G12V(3-42) |
| 9 | VVVGADGVGK | 7-16 G12D |
| 10 | VVVGAVGVGK | 7-16 G12V |
| 11 | VVVGACGVGK | 7-16 G12C |
| 12 | VVGADGVGK | 8-16 G12D |
| 13 | VVGAVGVGK | 8-16 G12V |
| 14 | KLVVVGADGV | 5-14 G12D |
| 15 | GADGVGKSAL | 10-19 G12D |

What is claimed is:

1. A composition comprising red blood cell (RBC) ghosts, wherein the RBC ghosts comprise an exogenous mutated Ras antigen loaded intravesicularly, and wherein the exogenous mutated Ras antigen is a peptide or a polypeptide.

2. The composition of claim 1, wherein the composition further comprises an adjuvant.

3. The composition of claim 2, wherein the adjuvant is a CpG oligodeoxynucleotide (ODN), LPS, IFN-α, IFN-β, IFN-γ, alpha-Galactosyl Ceramide, STING agonist, cyclic dinucleotide (CDN), RIG-I agonist, polyinosinic-polycytidylic acid, R837, R848, a TLR3 agonist, a TLR4 agonist or a TLR9 agonist.

4. A composition comprising red blood cell (RBC) ghosts, wherein: the RBC ghosts comprise a cargo, wherein a) the cargo comprises an exogenous mutated Ras antigen, or an exogenous mutated Ras antigen and an adjuvant, and b) wherein the mutated Ras antigen is a peptide or polypeptide; and the RBC ghosts comprising the cargo are prepared by:

a) passing a cell suspension comprising input RBCs through a cell-deforming constriction, wherein a diameter of the constriction is a function of a diameter of the cells in the suspension, thereby causing perturbations of the cell suspension large enough for the cargo to pass through to form a perturbed cell suspension; and b) incubating the perturbed cell suspension with the cargo for a sufficient time to allow the cargo to enter the perturbed cell suspension; and c) enriching the cell suspension comprising cargo for RBC ghosts comprising cargo.

5. The composition of claim 4, wherein the width of the constriction is about 10% to about 99% of the mean diameter of the input RBCs.

6. The composition of claim 4, wherein the width of the constriction is about 1.6 μm to about 2.4 μm or about 1.8 μm to about 2.2 μm.

7. The composition of claim 4, wherein the cell suspension is passed through multiple constrictions arranged in series and/or in parallel.

8. The composition of claim 4, wherein the exogenous mutated Ras antigen is a mutated K-Ras antigen, a mutated H-Ras antigen, or a mutated N-Ras antigen.

9. The composition of claim 4, wherein the exogenous mutated Ras antigen is:

a) a single polypeptide that elicits a response against the same and or different mutated Ras antigens; and/or b) a pool of multiple polypeptides that elicit a response against the same and or different mutated Ras antigens.

10. The composition of claim 8, wherein the exogenous mutated Ras antigen comprises a G12D mutation, a G12V mutation, a G12C mutation, or a G13D mutation.

11. The composition of claim 4, wherein the adjuvant is a CpG oligodeoxynucleotide (ODN), LPS, IFN-α, IFN-β, IFN-γ, alpha-Galactosyl Ceramide, STING agonist, cyclic dinucleotide (CDN), RIG-I agonist, polyinosinic-polycytidylic acid, R837, R848, a TLR3 agonist, a TLR4 agonist or a TLR9 agonist.

12. A method for producing a composition comprising red blood cell (RBC) ghosts comprising an exogenous mutated Ras antigen, wherein the method comprises:

a) loading exogenous mutated Ras antigen intravesicularly into a sample comprising RBC, and b) enriching the loaded sample comprising RBC for RBC ghosts comprising the exogenous mutated Ras antigen; and wherein the exogenous mutated Ras antigen is a peptide or a polypeptide.

13. The method of claim 12, wherein the RBC ghosts further comprises an adjuvant.

14. The method of claim 13, wherein the adjuvant is a CpG oligodeoxynucleotide (ODN), LPS, IFN-α, IFN-β, IFN-γ, alpha-Galactosyl Ceramide, STING agonist, cyclic dinucleotide (CDN), RIG-I agonist, polyinosinic-polycytidylic acid, R837, R848, a TLR3 agonist, a TLR4 agonist or a TLR9 agonist.

15. The method of claim 13, wherein loading the exogenous mutated Ras antigen, or the exogenous mutated Ras antigen and the adjuvant, into RBC ghosts comprises:

a) passing a cell suspension comprising input RBCs through a cell-deforming constriction, wherein a diameter of the constriction is a function of a diameter of the cells in the suspension, thereby causing perturbations of the cell suspension large enough for the exogenous mutated Ras antigen, or the exogenous mutated Ras antigen and the adjuvant, to pass through to form a perturbed cell suspension; and b) incubating the perturbed cell suspension with the exogenous mutated Ras antigen, or the exogenous mutated Ras antigen and the adjuvant, for a sufficient time to allow the exogenous mutated Ras antigen, or the exogenous mutated Ras antigen and the adjuvant, to enter the perturbed cell suspension; thereby generating a cell suspension comprising RBC ghosts comprising the exogenous mutated Ras antigen, or the exogenous mutated Ras antigen and the adjuvant.

16. The method of claim 15, wherein the width of the constriction is about 10% to about 99% of the mean diameter of the input RBCs.

17. The method of claim 15, wherein the width of the constriction is about 1.6 μm to about 2.4 μm or about 1.8 μm to about 2.2 μm.

18. The method of claim 15, wherein the cell suspension comprising the is passed through multiple constrictions arranged in series and/or in parallel.

19. The method of claim 1, wherein the input red blood cells are from a healthy donor.

20. The method of claim 1, wherein the RBC ghosts exhibit cell surface phosphatidylserine.

* * * * *